United States Patent [19]
Johnson

[11] Patent Number: 5,981,265
[45] Date of Patent: Nov. 9, 1999

[54] METHODS FOR REGULATING MEKK PROTEIN ACTIVITY

[75] Inventor: Gary L. Johnson, Boulder, Colo.

[73] Assignee: National Jewish Center for Immunology and Respiratory Medicine, Denver, Colo.

[21] Appl. No.: 08/461,146

[22] Filed: Jun. 5, 1995

Related U.S. Application Data

[63] Continuation of application No. 08/440,421, May 12, 1995, which is a continuation-in-part of application No. 08/345,516, Nov. 28, 1994, abandoned, which is a division of application No. 08/049,254, Apr. 15, 1993, Pat. No. 5,405,941, and a continuation-in-part of application No. 08/323,460, Oct. 14, 1994, and a continuation-in-part of application No. PCT/US94/11690, Oct. 14, 1994, Pat. No. 5,854,043, and a continuation-in-part of application No. PCT/US94/04178, Apr. 15, 1994, which is a continuation-in-part of application No. 08/049,254, Apr. 15, 1993, Pat. No. 5,405,941.

[51] Int. Cl.⁶ ..................................................... C12N 1/15
[52] U.S. Cl. ........................ 435/254.1; 435/194; 935/68
[58] Field of Search ..................................... 435/7.1, 69.1, 435/240.1, 252.3, 320.1, 254.1, 194; 530/300, 350; 536/23.1, 23.5; 935/68

[56] References Cited

U.S. PATENT DOCUMENTS

| 5,283,173 | 2/1994 | Fields et al. ................................. 435/5 |
| 5,296,353 | 3/1994 | Ochoa et al. .......................... 435/7.23 |
| 5,405,941 | 4/1995 | Johnson et al. ......................... 530/350 |

FOREIGN PATENT DOCUMENTS

WO 94/24159  10/1994  WIPO .
WO 95/28421  10/1995  WIPO .

OTHER PUBLICATIONS

Wang et al. (1991) Mol. Cell. Biol. 11:3554–3563.
Cichowski et al. (1992) J. Biol. Chem. 267:5025–5028.
Stein et al. (1993) Science 261:1004–1012.
Blumer, K., et al., "Mammalian Mitogen–Activated Protein Kinase Kinase Kinase (MEKK) can Function in a Yeast Mitogen–Activated Protein Kinase Pathway Downstream of Protein Kinase C," *Proc. Natl. Acad. Sci. USA*, vol. 91, 4925–4929 (1994).
Büscher, D., et al., "Ras–Dependent and–Independent Pathways Target the Mitogen–Activated Protein Kinase Network in Macrophages," *Mol. Cell. Biol.*, vol. 15, 466–475 (1995).
Chaleff, D. and Tatchell, K., "Molecular Cloning and Characterization of the STE7 and STE11 Genes of *Saccharomyces cerevisiae*," *Molecular and Cellular Biology*, vol. 5, 1878–1886 (1985).
Crews, C., et al., "The Primary Structure of MEK, a Protein Kinase that Phosphorylates the ERK Gene Product," *Science*, vol. 258, 478–480 (1992).
Dent, P., et al., "Activation of Mitogen–Activated Protein Kinase Kinase by v-Raf in NIH 3T3 Cells and in Vitro," *Science*, vol. 257, 1404–1407 (1992).

Dérijard, B., et al., "Independent Human MAP Kinase Signal Transduction Pathways Defined by MEK and MKK Isoforms," *Science*, vol. 267, 682–685 (1995).
Gardner, A., et al., "MEK–1 Phosphorylation by MEK Kinase, Raf, and Mitogen–activated Protein Kinase: Analysis of Phosphopeptides and Regulation of Activity," *Molecular Biology of the Cell*, vol. 5, 193–201 (1994).
Kyriakis, J., et al., "Raf–1 Activates MAP Kinase–kinase," *Nature*, vol. 358, 417–421 (1992).
Lange–Carter, C. and Johnson, G., "Ras–Dependent Growth Factor Regulation of MEK Kinase in PC12 Cells," *Science*, vol. 265, 1458–1461 (1994).
Lange–Carter, C., et al., "A Divergence in the MAP Kinase Regulatory Network Defined by MEK Kinase and Raf," *Science*, vol. 260, 315–319 (1993).
Lin, A., et al., "Identification of a Dual Specificity Kinase that Activates the Jun Kinases and p38–Mpk2," *Science*, vol. 268, 286–290 (1995).
Marshall, C., "MAP Kinase Kinase Kinase, MAP Kinase Kinase and MAP Kinase," *Current Opinion in Genetics and Development*, vol. 4, 82–89 (1994).
Masuda, T., et al., "Protein Kinase Byr2 ia a Target of Ras1 in the Fission Yeast *Schizosaccharomyces pombe*," *The Journal of Biological Chemistry*, vol. 270, No. 5, 1979–1982 (1995).
Minden, A., et al., "Differential Activation of ERK and JNK Mitogen–Activated Protein by Kinases by Raf–1 and MEKK," *Science*, vol. 266, 1719–1723 (1994).
Reuter, C., et al., "Biochemical Anaylsis of MEk Activation in NIH3T3 Fibroblasts," *The Journal of Biological Chemistry*, vol. 270, No. 13, 7644–7655 (1995).
Russell, M., et al., "Direct Interaction Between Ras and the Kinase Domain of Mitogen–activated Protein Kinase Kinase Kinase (MEKK1)," *The Journal of Biological Chemistry*, vol. 20, No. 20, 11757–11760 (1995).
Sánchez, I., et al., "Role of SAPK/ERK Kinase–1 in the Stress–Activated Pathway Regulating Transcription Factor c–Jun," *Nature*, vol. 372, 794–798 (1994).

(List continued on next page.)

*Primary Examiner*—Lorraine Spector
*Attorney, Agent, or Firm*—Lahive & Cockfield, LLP; Giulio A. DeConti, Jr.; Peter C. Lauro

[57] ABSTRACT

The present invention relates to isolated MEKK proteins, nucleic acid molecules having sequences that encode such proteins, and antibodies raised against such proteins. The present invention also includes methods to use such proteins to regulate signal transduction in a cell. The present invention also includes therapeutic compositions comprising such proteins or nucleic acid molecules that encode such proteins and their use to treat animals having medical disorders including cancer, inflammation, neurological disorders, autoimmune diseases, allergic reactions, and hormone-related diseases. When MEKK is expressed, it phosphorylates and activates MEKs including MEK-1, MEK-2 and JEK.

3 Claims, 36 Drawing Sheets

OTHER PUBLICATIONS

Ueki, K. et al., "Feedback Regulation of Mitogen–activated Protein Kinase Kinase Kinase Activity of c–Raf–1 by Insulin and Phorbol Ester Stimulation," *The Journal of Biological Chemistry,* vol. 269, No. 22, 15756–15761 (1994).

Wang, Y., et al., "byr2, a *Schizosaccharomyces pombe* Gene Encoding a Protein Kinase Capable of Partial Suppression of the ras 1 Mutant Phenotype," *Molecular and Cellular Biology,* vol. 11, No. 7, 3554–3563 (1991).

Whitehurst, C., et al., "The MEK Kinase Activity of the Catalytic Domain of Raf–1 is Regulated Independently of Ras Binding in T Cells," *The Journal of Biological Chemistry,* vol. 270, No. 10, 5594–5599 (1995).

Winston, B., et al., "Tumor Necrosis Factor α Rapidly Activates the Mitogen–Activated Protein Kinase (MAPK) Cascade in a MAPK Kinase Kinase–dependent, c–Raf–1–independent Fashion in Mouse Macrophages," *Proc. Natl. Acad. Sci. USA,* vol. 92, 1614–1618 (1995).

Yan, M., and Templeton, D., "Identification of 2 Serine Residues of MEK–1 that are Differentially Phosphorylated During Activation by raf and MEK Kinase," *The Journal of Biological Chemistry,* vol. 269, No. 29, 19067–19073 (1994).

Yan, M., et al., "Activation of Stress–Activated Protein Kinase by MEKK1 Phosphorylation of its Activator SEK1," *Nature,* vol. 372, 798–800 (1994).

Zheng, C. and Guan, K., "Activation of MEK Family Kinases Requires Phosphorylation of Two Conserved Ser–Thr Residues," *The EMBO Journal,* vol. 13, No. 5, 1123–1131 (1994).

Laster, et al. J. Immunol. vol. 141(8): pp. 2629–2634, Oct. 1988.

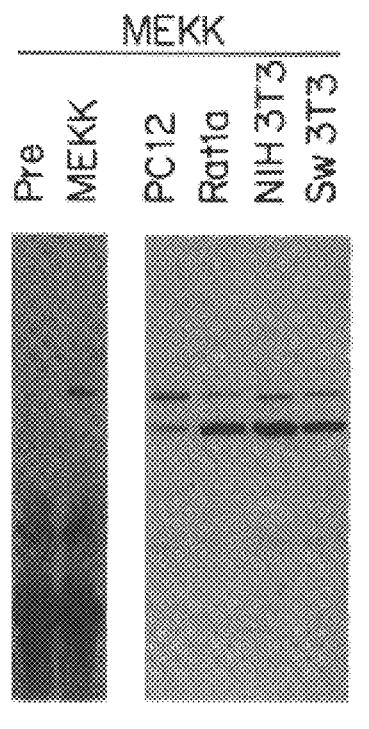
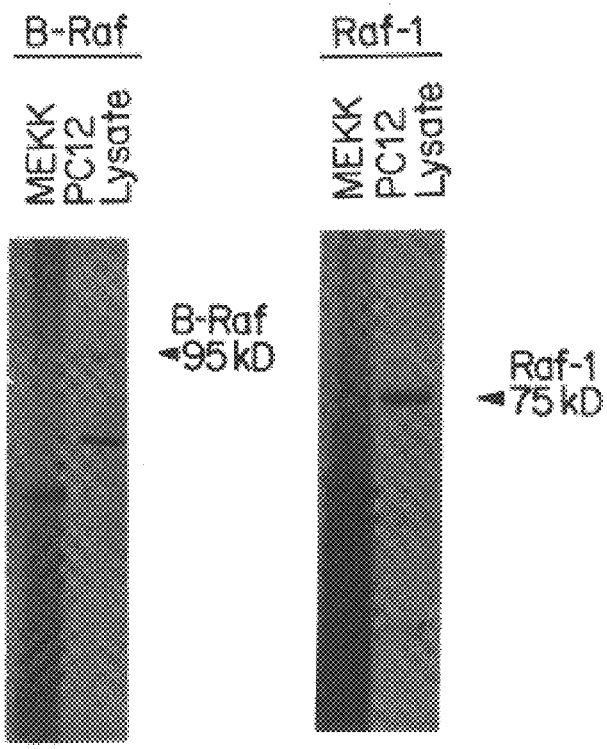

Myc-Gal 4 fusion protein:

pCMV5 Control Vector pCMV5-MEKK1 pCMV5-MEKK3

βgal | Propidium Iodide

Control

MEKK

BXB Raf

FIG.27A
FIG.27B
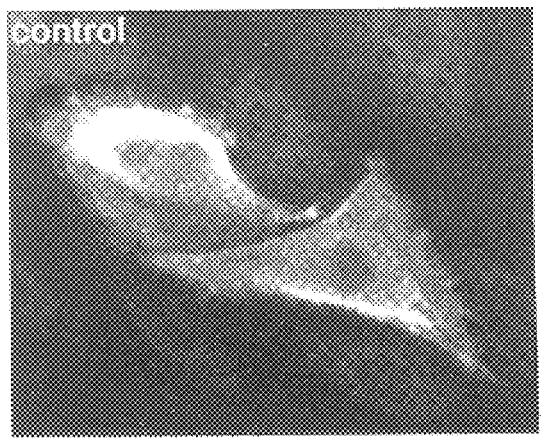
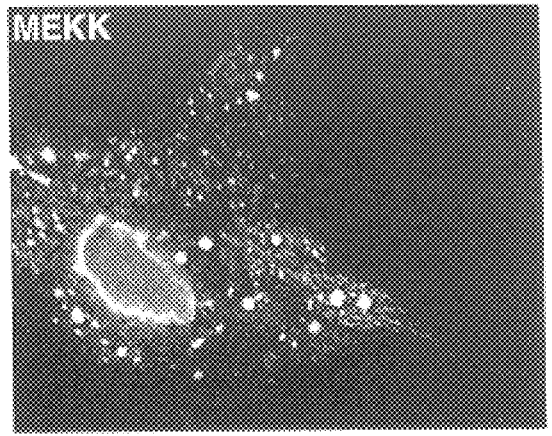
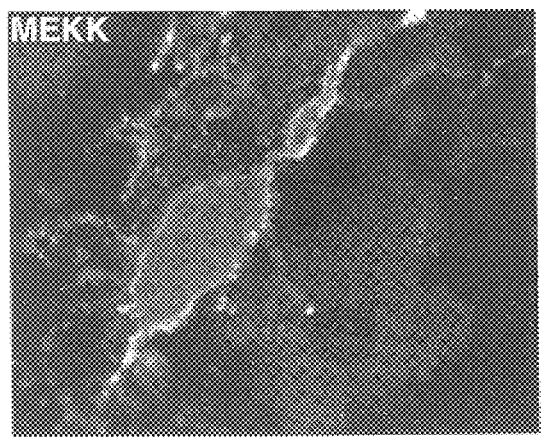
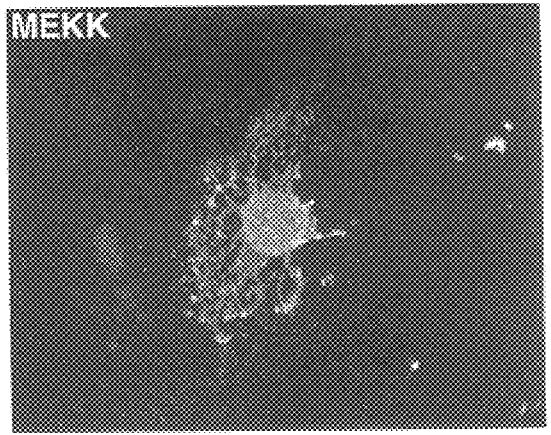
FIG.27C
FIG.27D

FIG.28A
FIG.28B
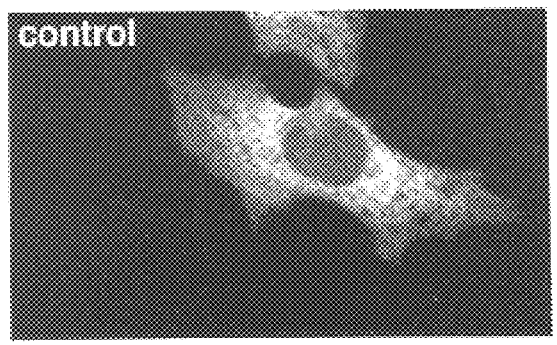
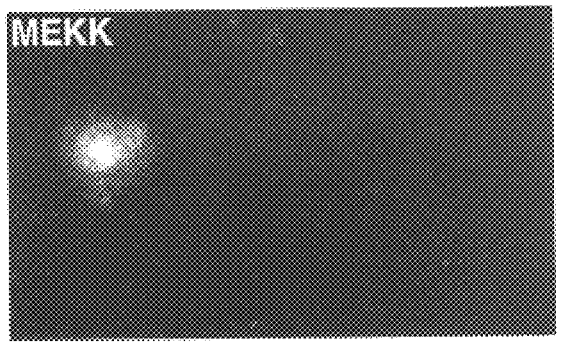
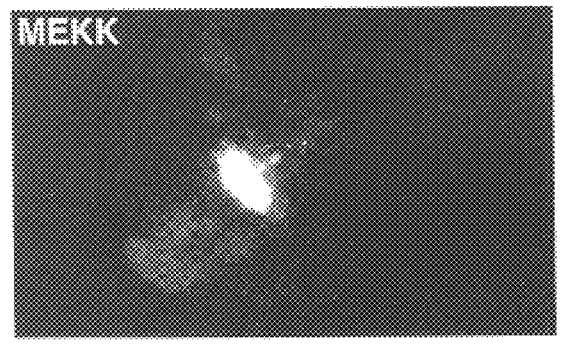
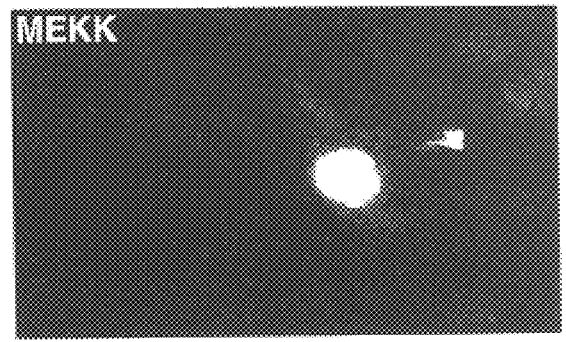
FIG.28C
FIG.28D

FIG. 33
FIG. 34
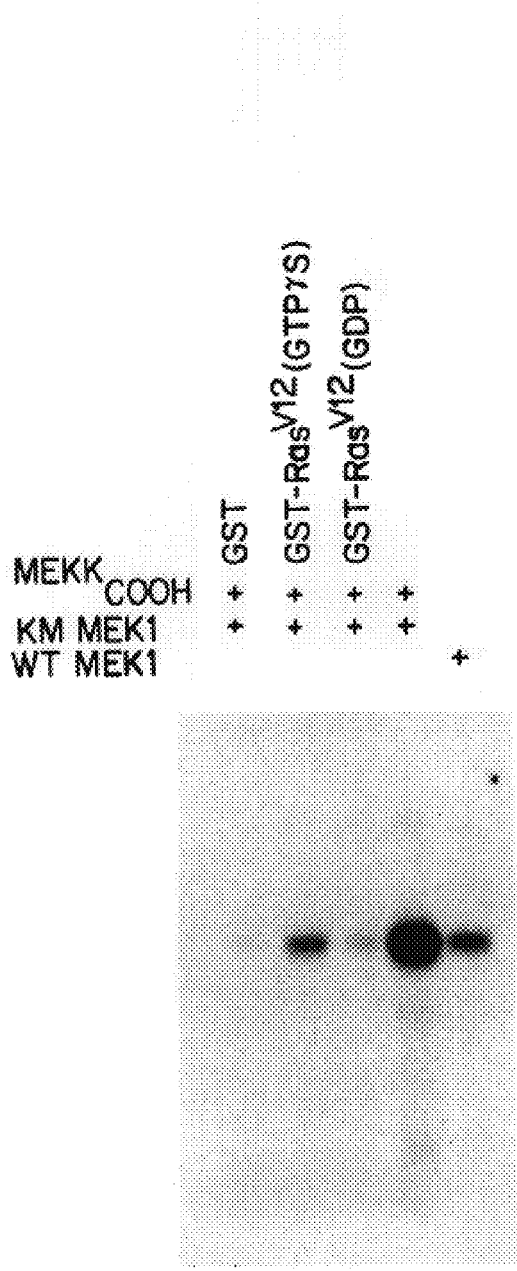
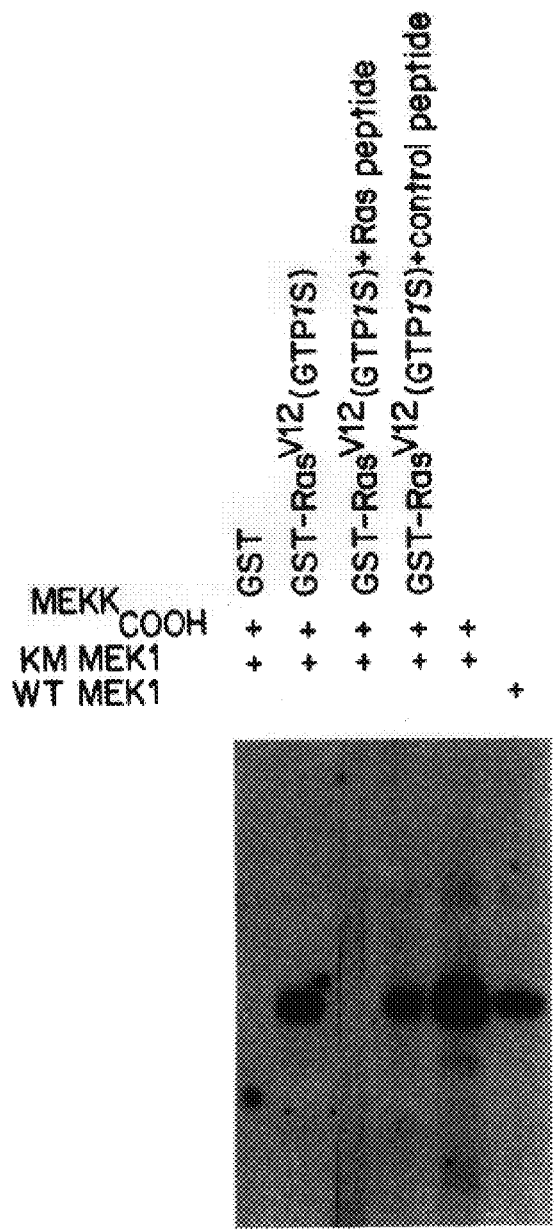

```
                       SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 3260 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: MEKK
         (B) STRAIN: murine (vii) IMMEDIATE SOURCE:
         (A) LIBRARY: mouse liver
```

(B) CLONE: MEKK cDNA (ix) FEATURE:
       (A) NAME/KEY: 5'UTR
       (B) LOCATION: 1..485
       (A) NAME/KEY: CDS
       (B) LOCATION: 486..2501
       (A) NAME/KEY: 3'UTR
       (B) LOCATION: 2502..3260

(xi) SEQUENCE DESCRIPTION: SEQ ID NO:1:

```
TACACTCCTT GCCACAGTCT GGCAGAAAGA ATCAAACTTC AGAGACTCCT CCGGCCAGTT      60

GTAGACACTA TCCTTGTCAA GTGTGCAGAT CCAACAGCCG CACGAGTCAG CTGTCCATAT     120

CTACAGTGCT GGAACTCTGC AAGGGCCAAG CAGGAGAGCT GGCGGTTGGG AGAGAAATAC     180

TTAAAGCTGG GTCCATCGGG GTTGGTGGTG TCGATTACGT CTTAAGTTGT ATCCTTGGAA     240

ACCAAGCTGA ATCAAACAAC TGGCAAGAAC TGCTGGGTCG CCTCTGTCTT ATAGACAGGT     300

TGCTGTTGGA ATTTCCTGCT GAATTCTATC CTCATATTGT CAGTACTGAT GTCTCACAAG     360

CTGAGCCTGT TGAAATCAGG TACAAGAAGC TGCTCTCCCT CTTAACCTTT GCCTTGCAAT     420

CCATTGACAA TTCCCACTCG ATGGTTGGCA AGCTCTCTCG GAGGATATAT CTGAGCTCTG     480

CCAGG ATG GTG ACC GCA GTG CCC GCT GTG TTT TCC AAG CTG GTA ACC         527
      Met Val Thr Ala Val Pro Ala Val Phe Ser Lys Leu Val Thr
        1               5                  10

ATG CTT AAT GCT TCT GGC TCC ACC CAC TTC ACC AGG ATG CGC CGG CGT       575
Met Leu Asn Ala Ser Gly Ser Thr His Phe Thr Arg Met Arg Arg Arg
 15                  20                  25                  30

CTG ATG GCT ATC GCG GAT GAG GTA GAA ATT GCC GAG GTC ATC CAG CTG       623
Leu Met Ala Ile Ala Asp Glu Val Glu Ile Ala Glu Val Ile Gln Leu
                 35                  40                  45

GGT GTG GAG GAC ACT GTG GAT GGG CAT CAG GAC AGC TTA CAG GCC GTG       671
Gly Val Glu Asp Thr Val Asp Gly His Gln Asp Ser Leu Gln Ala Val
             50                  55                  60

GCC CCC ACC AGC TGT CTA GAA AAC AGC TCC CTT GAG CAC ACA GTC CAT       719
Ala Pro Thr Ser Cys Leu Glu Asn Ser Ser Leu Glu His Thr Val His
         65                  70                  75

AGA GAG AAA ACT GGA AAA GGA CTA AGT GCT ACG AGA CTG AGT GCC AGC       767
Arg Glu Lys Thr Gly Lys Gly Leu Ser Ala Thr Arg Leu Ser Ala Ser
     80                  85                  90

TCG GAG GAC ATT TCT GAC AGA CTG GCC GGC GTC TCT GTA GGA CTT CCC       815
Ser Glu Asp Ile Ser Asp Arg Leu Ala Gly Val Ser Val Gly Leu Pro
 95                 100                 105                 110

AGC TCA ACA ACA ACA GAA CAA CCA AAG CCA GCG GTT CAA ACA AAA GGC       863
Ser Ser Thr Thr Thr Glu Gln Pro Lys Pro Ala Val Gln Thr Lys Gly
                115                 120                 125

AGA CCC CAC AGT CAG TGT TTG AAC TCC TCC CCT TTG TCT CAT GCT CAA       911
Arg Pro His Ser Gln Cys Leu Asn Ser Ser Pro Leu Ser His Ala Gln
            130                 135                 140

TTA ATG TTC CCA GCA CCA TCA GCC CCT TGT TCC TCT GCC CCG TCT GTC       959
Leu Met Phe Pro Ala Pro Ser Ala Pro Cys Ser Ser Ala Pro Ser Val
        145                 150                 155

CCA GAT ATT TCT AAG CAC AGA CCC CAG GCA TTT GTT CCC TGC AAA ATA      1007
Pro Asp Ile Ser Lys His Arg Pro Gln Ala Phe Val Pro Cys Lys Ile
    160                 165                 170

CCT TCC GCA TCT CCT CAG ACA CAG CGC AAG TTC TCT CTA CAA TTC CAG      1055
Pro Ser Ala Ser Pro Gln Thr Gln Arg Lys Phe Ser Leu Gln Phe Gln
175                 180                 185                 190

AGG AAC TGC TCT GAA CAC CGA GAC TCA GAC CAG CTC TCC CCA GTC TTC      1103
Arg Asn Cys Ser Glu His Arg Asp Ser Asp Gln Leu Ser Pro Val Phe
                195                 200                 205
```

-continued

| | | |
|---|---|---|
| ACT CAG TCA AGA CCC CCA CCC TCC AGT AAC ATA CAC AGG CCA AAG CCA<br>Thr Gln Ser Arg Pro Pro Pro Ser Ser Asn Ile His Arg Pro Lys Pro<br>              210                        215                    220 | 1151 |
| TCC CGA CCC GTT CCG GGC AGT ACA AGC AAA CTA GGG GAC GCC ACA AAA<br>Ser Arg Pro Val Pro Gly Ser Thr Ser Lys Leu Gly Asp Ala Thr Lys<br>                  225                        230                        235 | 1199 |
| AGT AGC ATG ACA CTT GAT CTG GGC AGT GCT TCC AGG TGT GAC GAC AGC<br>Ser Ser Met Thr Leu Asp Leu Gly Ser Ala Ser Arg Cys Asp Asp Ser<br>240                        245                        250 | 1247 |
| TTT GGC GGC GGC AAC AGT GGC AAC GCC GTC ATA CCC AGC GAC GAG<br>Phe Gly Gly Gly Asn Ser Gly Asn Ala Val Ile Pro Ser Asp Glu<br>255                    260                    265                    270 | 1295 |
| ACA GTG TTC ACG CCG GTG GAG GAC AAG TGC AGG TTA GAT GTG AAC ACC<br>Thr Val Phe Thr Pro Val Glu Asp Lys Cys Arg Leu Asp Val Asn Thr<br>                  275                        280                        285 | 1343 |
| GAG CTC AAC TCC AGC ATC GAG GAC CTT CTT GAA GCA TCC ATG CCT TCA<br>Glu Leu Asn Ser Ser Ile Glu Asp Leu Leu Glu Ala Ser Met Pro Ser<br>              290                        295                        300 | 1391 |
| AGT GAC ACG ACA GTC ACT TTC AAG TCC GAA GTC GCC GTC CTC TCT CCG<br>Ser Asp Thr Thr Val Thr Phe Lys Ser Glu Val Ala Val Leu Ser Pro<br>                  305                        310                    315 | 1439 |
| GAA AAG GCC GAA AAT GAC GAC ACC TAC AAA GAC GAC GTC AAT CAT AAT<br>Glu Lys Ala Glu Asn Asp Asp Thr Tyr Lys Asp Asp Val Asn His Asn<br>320                        325                        330 | 1487 |
| CAA AAG TGC AAA GAA AAG ATG GAA GCT GAA GAG GAG GAG GCT TTA GCG<br>Gln Lys Cys Lys Glu Lys Met Glu Ala Glu Glu Glu Glu Ala Leu Ala<br>335                        340                    345                    350 | 1535 |
| ATC GCC ATG GCG ATG TCA GCG TCT CAG GAT GCC CTC CCC ATC GTC CCT<br>Ile Ala Met Ala Met Ser Ala Ser Gln Asp Ala Leu Pro Ile Val Pro<br>                  355                        360                    365 | 1583 |
| CAG CTG CAG GTG GAA AAT GGA GAA GAT ATT ATC ATC ATT CAG CAG GAC<br>Gln Leu Gln Val Glu Asn Gly Glu Asp Ile Ile Ile Ile Gln Gln Asp<br>                  370                        375                    380 | 1631 |
| ACA CCA GAA ACT CTT CCA GGA CAT ACC AAA GCG AAA CAG CCT TAC AGA<br>Thr Pro Glu Thr Leu Pro Gly His Thr Lys Ala Lys Gln Pro Tyr Arg<br>              385                        390                        395 | 1679 |
| GAA GAC GCT GAG TGG CTG AAA GGC CAG CAG ATA GGC CTC GGA GCA TTT<br>Glu Asp Ala Glu Trp Leu Lys Gly Gln Gln Ile Gly Leu Gly Ala Phe<br>            400                        405                    410 | 1727 |
| TCT TCC TGT TAC CAA GCA CAG GAT GTG GGG ACT GGG ACT TTA ATG GCT<br>Ser Ser Cys Tyr Gln Ala Gln Asp Val Gly Thr Gly Thr Leu Met Ala<br>415                        420                    425                    430 | 1775 |
| GTG AAA CAG GTG ACG TAC GTC AGA AAC ACA TCC TCC GAG CAG GAG GAG<br>Val Lys Gln Val Thr Tyr Val Arg Asn Thr Ser Ser Glu Gln Glu Glu<br>                  435                        440                    445 | 1823 |
| GTG GTG GAA GCG TTG AGG GAA GAG ATC CGG ATG ATG GGT CAC CTC AAC<br>Val Val Glu Ala Leu Arg Glu Glu Ile Arg Met Met Gly His Leu Asn<br>                  450                        455                    460 | 1871 |
| CAT CCA AAC ATC ATC CGG ATG CTG GGG GCC ACG TGC GAG AAG AGC AAC<br>His Pro Asn Ile Ile Arg Met Leu Gly Ala Thr Cys Glu Lys Ser Asn<br>              465                        470                    475 | 1919 |
| TAC AAC CTC TTC ATT GAG TGG ATG GCG GGA GGA TCT GTG GCT CAC CTC<br>Tyr Asn Leu Phe Ile Glu Trp Met Ala Gly Gly Ser Val Ala His Leu<br>480                        485                    490 | 1967 |
| TTG AGT AAA TAC GGA GCT TTC AAG GAG TCA GTC GTC ATT AAC TAC ACT<br>Leu Ser Lys Tyr Gly Ala Phe Lys Glu Ser Val Val Ile Asn Tyr Thr<br>495                        500                    505                    510 | 2015 |
| GAG CAG TTA CTG CGT GGC CTT TCC TAT CTC CAC GAG AAC CAG ATC ATT<br>Glu Gln Leu Leu Arg Gly Leu Ser Tyr Leu His Glu Asn Gln Ile Ile<br>                  515                        520                    525 | 2063 |

```
CAC AGA GAC GTC AAA GGT GCC AAC CTG CTC ATT GAC AGC ACC GGT CAG        2111
His Arg Asp Val Lys Gly Ala Asn Leu Leu Ile Asp Ser Thr Gly Gln
            530                 535                 540

AGG CTG AGA ATT GCA GAC TTT GGA GCT GCT GCC AGG TTG GCA TCA AAA        2159
Arg Leu Arg Ile Ala Asp Phe Gly Ala Ala Ala Arg Leu Ala Ser Lys
            545                 550                 555

GGA ACC GGT GCA GGA GAG TTC CAG GGA CAG TTA CTG GGG ACA ATT GCA        2207
Gly Thr Gly Ala Gly Glu Phe Gln Gly Gln Leu Leu Gly Thr Ile Ala
560                 565                 570

TTC ATG GCG CCT GAG GTC CTA AGA GGT CAG CAG TAT GGT AGG AGC TGT        2255
Phe Met Ala Pro Glu Val Leu Arg Gly Gln Gln Tyr Gly Arg Ser Cys
575                 580                 585                 590

GAT GTA TGG AGT GTT GGC TGC GCC ATT ATA GAA ATG GCT TGT GCA AAA        2303
Asp Val Trp Ser Val Gly Cys Ala Ile Ile Glu Met Ala Cys Ala Lys
            595                 600                 605

CCA CCT TGG AAT GCA GAA AAA CAC TCC AAT CAT CTC GCC TTG ATA TTT        2351
Pro Pro Trp Asn Ala Glu Lys His Ser Asn His Leu Ala Leu Ile Phe
            610                 615                 620

AAG ATT GCT AGC GCA ACT ACT GCA CCG TCC ATC CCG TCA CAC CTG TCC        2399
Lys Ile Ala Ser Ala Thr Thr Ala Pro Ser Ile Pro Ser His Leu Ser
            625                 630                 635

CCG GGT CTG CGC GAC GTG GCC GTG CGC TGC TTA GAA CTT CAG CCT CAG        2447
Pro Gly Leu Arg Asp Val Ala Val Arg Cys Leu Glu Leu Gln Pro Gln
640                 645                 650

GAC CGG CCT CCG TCC AGA GAG CTG CTG AAA CAT CCG GTC TTC CGT ACC        2495
Asp Arg Pro Pro Ser Arg Glu Leu Leu Lys His Pro Val Phe Arg Thr
655                 660                 665                 670

ACG TGG TAGTTAATTG TTCAGATCAG CTCTAATGGA GACAGGATAT CGAACCGGGA         2551
Thr Trp
GAGAGAAAAG AGAACTTGTG GGCGACCATG CCGCTAACCG CAGCCCTCAC GCCACTGAAC      2611

AGCCAGAAAC GGGGCCAGCG GGAACCGTA CCTAAGCATG TGATTGACAA ATCATGACCT       2671

GTACCTAAGC TCGATATGCA GACATCTACA GCTCGTGCAG GAACTGCACA CCGTGCCTTT      2731

CACAGGACTG GCTCTGGGGG ACCAGGAAGG CGATGGAGTT TGCATGACTA AGAACAGAA       2791

GCATAAATTT ATTTTTGGAG CACTTTTTCA GCTAATCAGT ATTACCATGT ACATCAACAT      2851

GCCCGCCACA TTTCAAACTC AGACTGTCCC AGATGTCAAG ATCCACTGTG TTTGAGTTTG      2911

TTTGCAGTTC CCTCAGCTTG CTGGTAATTG TGGTGTTTTG TTTTCGATGC AAATGTGATG      2971

TAATATTCTT ATTTTCTTTG GATCAAAGCT GGACTGAAAA TTGTACTGTG TAATTATTTT      3031

TGTGTTTTTA ATGTTATTTG GTACTCGAAT TGTAAATAAC GTCTACTGCT GTTTATTCCA      3091

GTTTCTACTA CCTCAGGTGT CCTATAGATT TTTCTTCTAC CAAAGTTCAC TCTCAGAATG      3151

AAATTCTACG TGCTGTGTGA CTATGACTCC TAAGACTTCC AGGGCTTAAG GGCTAACTCC      3211

TATTAGCACC TTACTATGTA AGCAAATGCT ACAAAAAAAA AAAAAAAA                   3260

(2) INFORMATION FOR SEQ ID NO:2:

(i) SEQUENCE CHARACTERISTICS:
        (A) LENGTH: 672 amino acids
        (B) TYPE: amino acid
        (D) TOPOLOGY: linear (ii) MOLECULE TYPE: protein (xi) SEQUENCE DESCRIPTION: SEQ ID NO:2:

Met Val Thr Ala Val Pro Ala Val Phe Ser Lys Leu Val Thr Met Leu
  1               5                  10                  15

Asn Ala Ser Gly Ser Thr His Phe Thr Arg Met Arg Arg Arg Leu Met
            20                  25                  30
```

-continued

Ala Ile Ala Asp Glu Val Glu Ile Ala Glu Val Ile Gln Leu Gly Val
         35                  40                  45

Glu Asp Thr Val Asp Gly His Gln Asp Ser Leu Gln Ala Val Ala Pro
 50                  55                  60

Thr Ser Cys Leu Glu Asn Ser Ser Leu Glu His Thr Val His Arg Glu
 65                  70                  75                  80

Lys Thr Gly Lys Gly Leu Ser Ala Thr Arg Leu Ser Ala Ser Ser Glu
                 85                  90                  95

Asp Ile Ser Asp Arg Leu Ala Gly Val Ser Val Gly Leu Pro Ser Ser
            100                 105                 110

Thr Thr Thr Glu Gln Pro Lys Pro Ala Val Gln Thr Lys Gly Arg Pro
        115                 120                 125

His Ser Gln Cys Leu Asn Ser Ser Pro Leu Ser His Ala Gln Leu Met
    130                 135                 140

Phe Pro Ala Pro Ser Ala Pro Cys Ser Ser Ala Pro Ser Val Pro Asp
145                 150                 155                 160

Ile Ser Lys His Arg Pro Gln Ala Phe Val Pro Cys Lys Ile Pro Ser
                165                 170                 175

Ala Ser Pro Gln Thr Gln Arg Lys Phe Ser Leu Gln Phe Gln Arg Asn
            180                 185                 190

Cys Ser Glu His Arg Asp Ser Asp Gln Leu Ser Pro Val Phe Thr Gln
        195                 200                 205

Ser Arg Pro Pro Pro Ser Ser Asn Ile His Arg Pro Lys Pro Ser Arg
    210                 215                 220

Pro Val Pro Gly Ser Thr Ser Lys Leu Gly Asp Ala Thr Lys Ser Ser
225                 230                 235                 240

Met Thr Leu Asp Leu Gly Ser Ala Ser Arg Cys Asp Asp Ser Phe Gly
                245                 250                 255

Gly Gly Gly Asn Ser Gly Asn Ala Val Ile Pro Ser Asp Glu Thr Val
            260                 265                 270

Phe Thr Pro Val Glu Asp Lys Cys Arg Leu Asp Val Asn Thr Glu Leu
        275                 280                 285

Asn Ser Ser Ile Glu Asp Leu Leu Glu Ala Ser Met Pro Ser Ser Asp
    290                 295                 300

Thr Thr Val Thr Phe Lys Ser Glu Val Ala Val Leu Ser Pro Glu Lys
305                 310                 315                 320

Ala Glu Asn Asp Asp Thr Tyr Lys Asp Val Asn His Asn Gln Lys
                325                 330                 335

Cys Lys Glu Lys Met Glu Ala Glu Glu Glu Ala Leu Ala Ile Ala
            340                 345                 350

Met Ala Met Ser Ala Ser Gln Asp Ala Leu Pro Ile Val Pro Gln Leu
        355                 360                 365

Gln Val Glu Asn Gly Glu Asp Ile Ile Ile Gln Gln Asp Thr Pro
    370                 375                 380

Glu Thr Leu Pro Gly His Thr Lys Ala Lys Gln Pro Tyr Arg Glu Asp
385                 390                 395                 400

Ala Glu Trp Leu Lys Gly Gln Gln Ile Gly Leu Gly Ala Phe Ser Ser
                405                 410                 415

Cys Tyr Gln Ala Gln Asp Val Gly Thr Gly Thr Leu Met Ala Val Lys
            420                 425                 430

Gln Val Thr Tyr Val Arg Asn Thr Ser Ser Glu Gln Glu Glu Val Val
        435                 440                 445

Glu Ala Leu Arg Glu Glu Ile Arg Met Met Gly His Leu Asn His Pro
450                 455                 460

-continued

```
Asn Ile Ile Arg Met Leu Gly Ala Thr Cys Glu Lys Ser Asn Tyr Asn
465                 470                 475                 480

Leu Phe Ile Glu Trp Met Ala Gly Gly Ser Val Ala His Leu Ser
                485                 490                 495

Lys Tyr Gly Ala Phe Lys Glu Ser Val Val Ile Asn Tyr Thr Glu Gln
            500                 505                 510

Leu Leu Arg Gly Leu Ser Tyr Leu His Glu Asn Gln Ile Ile His Arg
        515                 520                 525

Asp Val Lys Gly Ala Asn Leu Leu Ile Asp Ser Thr Gly Gln Arg Leu
    530                 535                 540

Arg Ile Ala Asp Phe Gly Ala Ala Arg Leu Ala Ser Lys Gly Thr
545                 550                 555                 560

Gly Ala Gly Glu Phe Gln Gly Gln Leu Leu Gly Thr Ile Ala Phe Met
                565                 570                 575

Ala Pro Glu Val Leu Arg Gly Gln Gln Tyr Gly Arg Ser Cys Asp Val
            580                 585                 590

Trp Ser Val Gly Cys Ala Ile Ile Glu Met Ala Cys Ala Lys Pro Pro
        595                 600                 605

Trp Asn Ala Glu Lys His Ser Asn His Leu Ala Leu Ile Phe Lys Ile
    610                 615                 620

Ala Ser Ala Thr Thr Ala Pro Ser Ile Pro Ser His Leu Ser Pro Gly
625                 630                 635                 640

Leu Arg Asp Val Ala Val Arg Cys Leu Glu Leu Gln Pro Gln Asp Arg
                645                 650                 655

Pro Pro Ser Arg Glu Leu Leu Lys His Pro Val Phe Arg Thr Thr Trp
            660                 665                 670
```

(2) INFORMATION FOR SEQ ID NO:3:

(i) SEQUENCE CHARACTERISTICS:
       (A) LENGTH: 2503 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: CDS
       (B) LOCATION: 466..2325

(xi) SEQUENCE DESCRIPTION: SEQ ID NO:3:

```
GGTGGCGGCC GCTCTAGAAC TAGTGGATCC CCCGGGCTGC AGGAATTCGG CACGAGGGAC    60

GATCCAGCGG CAGAGTCGCC GCTTCCGCTT CGCTGCTTCT CCGGTCGGCG ACGCGGGCCC   120

GGGGCTTCCT TTTCATCGGC CCAGCTTATT CCGCGGGCCC CGGGGCTGCA GCTACCCAGA   180

AGCGGCGAAG AGGCCCTGGG CTGCGCGCCC GCTGTCCCAT GTGAAGCAGG TTGGGCCTGG   240

TCCCCGGCCC GTGCCCGGTT GTCTGCGGCC CTTCAGGCCT CAGGGACCCC CGCGAGGCGC   300

TGCTCCTGGG GGGCGCGGTG ACAGGCCGTG CGGGGGCGGA GGGGCCAGCT CGGTGGCCTC   360

CTCTCGGCCC TCGCGTCCGC GATCCCGCCC AGCGGCCGGG CAATAAAGAA TGTTGATGGG   420

AGAACCATTT TCCTAATTTT CAAATTATTG AGCTGGTCGC GCATA ATG GAT GAT       474
                                                   Met Asp Asp
                                                     1

CAG CAA GCT TTG AAT TCA ATC ATG CAA GAT TTG GCT GTC CTT CAT AAG    522
Gln Gln Ala Leu Asn Ser Ile Met Gln Asp Leu Ala Val Leu His Lys
      5                  10                  15

CCA GTC GGC CAG CAT TAT CTT TAC AAG AAA CCA GGA AAG CAA AAC CTT    570
```

```
Pro Val Gly Gln His Tyr Leu Tyr Lys Lys Pro Gly Lys Gln Asn Leu
 20                  25                  30                  35

CAT CAC CAA AAA AAC AGA ATG ATG TTC GAG TCA AAT TTG AAC ATA GAG          618
His His Gln Lys Asn Arg Met Met Phe Glu Ser Asn Leu Asn Ile Glu
                 40                  45                  50

GAG GAA AAA AGG ATC CTG CAG GTT ACT AGA CCA GTT AAA CTA GAA GAC          666
Glu Glu Lys Arg Ile Leu Gln Val Thr Arg Pro Val Lys Leu Glu Asp
             55                  60                  65

CTG AGA TCT AAG TCT AAG ATC GCC TTT GGG CAG TCT ATG GAT CTA CAC          714
Leu Arg Ser Lys Ser Lys Ile Ala Phe Gly Gln Ser Met Asp Leu His
         70                  75                  80

TAT ACC AAC AAT GAG TTG GTA ATT CCG TTA ACT ACC CAA GAT GAC TTG          762
Tyr Thr Asn Asn Glu Leu Val Ile Pro Leu Thr Thr Gln Asp Asp Leu
     85                  90                  95

GAC AAA GCT GTG GAA CTG CTG GAT CGC AGT ATT CAC ATG AAG AGT CTC          810
Asp Lys Ala Val Glu Leu Leu Asp Arg Ser Ile His Met Lys Ser Leu
100                 105                 110                 115

AAG ATA TTA CTT GTA GTA AAT GGG AGT ACA CAG GCT ACT AAT TTA GAA          858
Lys Ile Leu Leu Val Val Asn Gly Ser Thr Gln Ala Thr Asn Leu Glu
                120                 125                 130

CCA TCA CCG TCA CCA GAA GAT TTG AAT AAT ACA CCA CTT GGT GCA GAG          906
Pro Ser Pro Ser Pro Glu Asp Leu Asn Asn Thr Pro Leu Gly Ala Glu
            135                 140                 145

AGG AAA AAG CGG CTA TCT GTA GTA GGT CCC CCT AAT AGG GAT AGA AGT          954
Arg Lys Lys Arg Leu Ser Val Val Gly Pro Pro Asn Arg Asp Arg Ser
        150                 155                 160

TCC CCT CCT CCA GGA TAC ATT CCA GAC ATA CTA CAC CAG ATT GCC CGG         1002
Ser Pro Pro Pro Gly Tyr Ile Pro Asp Ile Leu His Gln Ile Ala Arg
    165                 170                 175

AAT GGG TCA TTC ACT AGC ATC AAC AGT GAA GGA GAG TTC ATT CCA GAG         1050
Asn Gly Ser Phe Thr Ser Ile Asn Ser Glu Gly Glu Phe Ile Pro Glu
180                 185                 190                 195

AGC ATG GAC CAA ATG CTG GAT CCA TTG TCT TTA AGC AGC CCT GAA AAT         1098
Ser Met Asp Gln Met Leu Asp Pro Leu Ser Leu Ser Ser Pro Glu Asn
                200                 205                 210

TCT GGC TCA GGA AGC TGT CCG TCA CTT GAT AGT CCT TTG GAT GGA GAA         1146
Ser Gly Ser Gly Ser Cys Pro Ser Leu Asp Ser Pro Leu Asp Gly Glu
            215                 220                 225

AGC TAC CCA AAA TCA CGG ATG CCT AGG GCA CAG AGC TAC CCA GAT AAT         1194
Ser Tyr Pro Lys Ser Arg Met Pro Arg Ala Gln Ser Tyr Pro Asp Asn
        230                 235                 240

CAT CAG GAG TTT ACA GAC TAT GAT AAC CCC ATT TTT GAG AAA TTT GGA         1242
His Gln Glu Phe Thr Asp Tyr Asp Asn Pro Ile Phe Glu Lys Phe Gly
    245                 250                 255

AAA GGA GGA ACA TAT CCA AGA AGG TAC CAC GTT TCC TAT CAT CAC CAG         1290
Lys Gly Gly Thr Tyr Pro Arg Arg Tyr His Val Ser Tyr His His Gln
260                 265                 270                 275

GAG TAT AAT GAC GGT CGG AAG ACT TTT CCA AGA GCT AGA AGG ACC CAG         1338
Glu Tyr Asn Asp Gly Arg Lys Thr Phe Pro Arg Ala Arg Arg Thr Gln
                280                 285                 290

GGC ACC AGT TTC CGG TCT CCT GTG AGC TTC AGT CCT ACT GAT CAC TCC         1386
Gly Thr Ser Phe Arg Ser Pro Val Ser Phe Ser Pro Thr Asp His Ser
            295                 300                 305

TTA AGC ACT AGT AGT GGA AGC AGT GTC TTT ACC CCA GAG TAT GAC GAC         1434
Leu Ser Thr Ser Ser Gly Ser Ser Val Phe Thr Pro Glu Tyr Asp Asp
        310                 315                 320

AGT CGA ATA AGA AGA CGG GGG AGT GAC ATA GAC AAT CCT ACT TTG ACT         1482
Ser Arg Ile Arg Arg Arg Gly Ser Asp Ile Asp Asn Pro Thr Leu Thr
    325                 330                 335

GTC ACA GAC ATC AGC CCA CCC AGC CGT TCA CCT CGA GCT CCG ACC AAC         1530
```

```
Val Thr Asp Ile Ser Pro Pro Ser Arg Ser Pro Arg Ala Pro Thr Asn
340                 345                 350                 355

TGG AGA CTG GGC AAG CTG CTT GGC CAA GGA GCT TTT GGT AGG GTC TAC    1578
Trp Arg Leu Gly Lys Leu Leu Gly Gln Gly Ala Phe Gly Arg Val Tyr
            360                 365                 370

CTC TGC TAT GAT GTT GAT ACC GGA AGA GAG CTG GCT GTT AAG CAA GTT    1626
Leu Cys Tyr Asp Val Asp Thr Gly Arg Glu Leu Ala Val Lys Gln Val
                375                 380                 385

CAG TTT AAC CCT GAG AGC CCA GAG ACC AGC AAG GAA GTA AAT GCA CTT    1674
Gln Phe Asn Pro Glu Ser Pro Glu Thr Ser Lys Glu Val Asn Ala Leu
            390                 395                 400

GAG TGT GAA ATT CAG TTG TTA AAA AAC TTG TTG CAT GAG CGA ATT GTT    1722
Glu Cys Glu Ile Gln Leu Leu Lys Asn Leu Leu His Glu Arg Ile Val
        405                 410                 415

CAG TAT TAT GGC TGT TTG AGG GAT CCT CAG GAG AAA ACA CTT TCC ATC    1770
Gln Tyr Tyr Gly Cys Leu Arg Asp Pro Gln Glu Lys Thr Leu Ser Ile
420                 425                 430                 435

TTT ATG GAG CTC TCG CCA GGG GGT TCA ATT AAG GAC CAA CTA AAA GCC    1818
Phe Met Glu Leu Ser Pro Gly Gly Ser Ile Lys Asp Gln Leu Lys Ala
            440                 445                 450

TAC GGA GCT CTT ACT GAG AAC GTG ACG AGG AAG TAC ACC CGT CAG ATT    1866
Tyr Gly Ala Leu Thr Glu Asn Val Thr Arg Lys Tyr Thr Arg Gln Ile
                455                 460                 465

CTG GAG GGG GTC CAT TAT TTG CAT AGT AAT ATG ATT GTC CAT AGA GAT    1914
Leu Glu Gly Val His Tyr Leu His Ser Asn Met Ile Val His Arg Asp
            470                 475                 480

ATC AAA GGA GCA AAT ATC TTA AGG GAT TCC ACA GGC AAT ATC AAG TTA    1962
Ile Lys Gly Ala Asn Ile Leu Arg Asp Ser Thr Gly Asn Ile Lys Leu
        485                 490                 495

GGA GAC TTT GGG GCT AGT AAA CGG CTT CAG ACC ATC TGT CTC TCA GGC    2010
Gly Asp Phe Gly Ala Ser Lys Arg Leu Gln Thr Ile Cys Leu Ser Gly
500                 505                 510                 515

ACA GGA ATG AAG TCT GTC ACA GGC ACG CCA TAC TGG ATG AGT CCT GAG    2058
Thr Gly Met Lys Ser Val Thr Gly Thr Pro Tyr Trp Met Ser Pro Glu
            520                 525                 530

GTC ATC AGT GGA GAA GGC TAT GGA AGA AAA GCA GAC ATC TGG AGT GTA    2106
Val Ile Ser Gly Glu Gly Tyr Gly Arg Lys Ala Asp Ile Trp Ser Val
                535                 540                 545

GCA TGT ACT GTG GTA GAA ATG CTA ACT GAA AAG CCA CCT TGG GCT GAA    2154
Ala Cys Thr Val Val Glu Met Leu Thr Glu Lys Pro Pro Trp Ala Glu
            550                 555                 560

TTT GAA GCA ATG GCT GCC ATC TTT AAG ATC GCC ACT CAG CCA ACG AAC    2202
Phe Glu Ala Met Ala Ala Ile Phe Lys Ile Ala Thr Gln Pro Thr Asn
        565                 570                 575

CCA AAG CTG CCA CCT CAT GTC TCA GAC TAT ACT CGG GAC TTC CTC AAA    2250
Pro Lys Leu Pro Pro His Val Ser Asp Tyr Thr Arg Asp Phe Leu Lys
580                 585                 590                 595

CGG ATT TTT GTA GAG GCC AAA CTT CGA CCT TCA GCG GAG GAG CTC TTG    2298
Arg Ile Phe Val Glu Ala Lys Leu Arg Pro Ser Ala Glu Glu Leu Leu
            600                 605                 610

CGG CAC ATG TTT GTG CAT TAT CAC TAGCAGCGGC GGCTTCGGTC CTCCACCAGC    2352
Arg His Met Phe Val His Tyr His
            615                 620

TCCATCCTCG CGGCCACCTT CTCTCTTACT GCACTTTCCT TTTTTATAAA AAAGAGAGAT    2412

GGGGAGAAAA AGACAAGAGG GAAATATTTT CTCTTGATTC TTGGTTAAAT TTGTTTAATA    2472

ATAATAGTAA ACTAAAAAAA AAAAAAAAAA A                                   2503

(2) INFORMATION FOR SEQ ID NO:4:
```

-continued

```
    (i) SEQUENCE CHARACTERISTICS:
        (A) LENGTH: 619 amino acids
        (B) TYPE: amino acid
        (D) TOPOLOGY: linear (ii) MOLECULE TYPE: protein (xi) SEQUENCE DESCRIPTION: SEQ ID NO:4:

Met Asp Asp Gln Gln Ala Leu Asn Ser Ile Met Gln Asp Leu Ala Val
 1               5                  10                  15

Leu His Lys Pro Val Gly Gln His Tyr Leu Tyr Lys Lys Pro Gly Lys
             20                  25                  30

Gln Asn Leu His His Gln Lys Asn Arg Met Met Phe Glu Ser Asn Leu
         35                  40                  45

Asn Ile Glu Glu Glu Lys Arg Ile Leu Gln Val Thr Arg Pro Val Lys
     50                  55                  60

Leu Glu Asp Leu Arg Ser Lys Ser Lys Ile Ala Phe Gly Gln Ser Met
 65                  70                  75                  80

Asp Leu His Tyr Thr Asn Asn Glu Leu Val Ile Pro Leu Thr Thr Gln
                 85                  90                  95

Asp Asp Leu Asp Lys Ala Val Glu Leu Leu Asp Arg Ser Ile His Met
            100                 105                 110

Lys Ser Leu Lys Ile Leu Leu Val Val Asn Gly Ser Thr Gln Ala Thr
        115                 120                 125

Asn Leu Glu Pro Ser Pro Ser Pro Glu Asp Leu Asn Asn Thr Pro Leu
    130                 135                 140

Gly Ala Glu Arg Lys Lys Arg Leu Ser Val Val Gly Pro Pro Asn Arg
145                 150                 155                 160

Asp Arg Ser Ser Pro Pro Gly Tyr Ile Pro Asp Ile Leu His Gln
                165                 170                 175

Ile Ala Arg Asn Gly Ser Phe Thr Ser Ile Asn Ser Glu Gly Glu Phe
            180                 185                 190

Ile Pro Glu Ser Met Asp Gln Met Leu Asp Pro Leu Ser Leu Ser Ser
        195                 200                 205

Pro Glu Asn Ser Gly Ser Gly Ser Cys Pro Ser Leu Asp Ser Pro Leu
    210                 215                 220

Asp Gly Glu Ser Tyr Pro Lys Ser Arg Met Pro Arg Ala Gln Ser Tyr
225                 230                 235                 240

Pro Asp Asn His Gln Glu Phe Thr Asp Tyr Asp Asn Pro Ile Phe Glu
                245                 250                 255

Lys Phe Gly Lys Gly Gly Thr Tyr Pro Arg Arg Tyr His Val Ser Tyr
            260                 265                 270

His His Gln Glu Tyr Asn Asp Gly Arg Lys Thr Phe Pro Arg Ala Arg
        275                 280                 285

Arg Thr Gln Gly Thr Ser Phe Arg Ser Pro Val Ser Phe Ser Pro Thr
    290                 295                 300

Asp His Ser Leu Ser Thr Ser Ser Gly Ser Ser Val Phe Thr Pro Glu
305                 310                 315                 320

Tyr Asp Asp Ser Arg Ile Arg Arg Arg Gly Ser Asp Ile Asp Asn Pro
                325                 330                 335

Thr Leu Thr Val Thr Asp Ile Ser Pro Pro Ser Arg Ser Pro Arg Ala
            340                 345                 350

Pro Thr Asn Trp Arg Leu Gly Lys Leu Leu Gly Gln Gly Ala Phe Gly
        355                 360                 365

Arg Val Tyr Leu Cys Tyr Asp Val Asp Thr Gly Arg Glu Leu Ala Val
    370                 375                 380
```

```
Lys Gln Val Gln Phe Asn Pro Glu Ser Pro Glu Thr Ser Lys Glu Val
385                 390                 395                 400

Asn Ala Leu Glu Cys Glu Ile Gln Leu Leu Lys Asn Leu Leu His Glu
            405                 410                 415

Arg Ile Val Gln Tyr Tyr Gly Cys Leu Arg Asp Pro Gln Glu Lys Thr
                420                 425                 430

Leu Ser Ile Phe Met Glu Leu Ser Pro Gly Ser Ile Lys Asp Gln
            435                 440                 445

Leu Lys Ala Tyr Gly Ala Leu Thr Glu Asn Val Thr Arg Lys Tyr Thr
450                 455                 460

Arg Gln Ile Leu Glu Gly Val His Tyr Leu His Ser Asn Met Ile Val
465                 470                 475                 480

His Arg Asp Ile Lys Gly Ala Asn Ile Leu Arg Asp Ser Thr Gly Asn
                485                 490                 495

Ile Lys Leu Gly Asp Phe Gly Ala Ser Lys Arg Leu Gln Thr Ile Cys
            500                 505                 510

Leu Ser Gly Thr Gly Met Lys Ser Val Thr Gly Thr Pro Tyr Trp Met
        515                 520                 525

Ser Pro Glu Val Ile Ser Gly Glu Gly Tyr Gly Arg Lys Ala Asp Ile
530                 535                 540

Trp Ser Val Ala Cys Thr Val Val Glu Met Leu Thr Glu Lys Pro Pro
545                 550                 555                 560

Trp Ala Glu Phe Glu Ala Met Ala Ala Ile Phe Lys Ile Ala Thr Gln
                565                 570                 575

Pro Thr Asn Pro Lys Leu Pro Pro His Val Ser Asp Tyr Thr Arg Asp
            580                 585                 590

Phe Leu Lys Arg Ile Phe Val Glu Ala Lys Leu Arg Pro Ser Ala Glu
        595                 600                 605

Glu Leu Leu Arg His Met Phe Val His Tyr His
        610                 615
```

(2) INFORMATION FOR SEQ ID NO:5:

(i) SEQUENCE CHARACTERISTICS:
        (A) LENGTH: 3089 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 400..2280

(xi) SEQUENCE DESCRIPTION: SEQ ID NO:5:

```
AGGGAACAAA AGCTGGAGCT CCACCGCGGT GGCGGCCGCT CTAGAACTAG TGGATCCCCC    60

GGGCTGCAGG AATTCGGCAC GAGGAACAGT GGCCGGTCGG AGCGTCTTCT GGACTTCAGG   120

ACTCGCAGGC GGCCCGGTCG AGTGGCGCCG CCGAGGCCGG GTTGGGCCGA GCCTGGGAGC   180

GCCGGGGATG TAGCGGGCCA ACCTGCTCAT GCCACAGCGC CCGGCCGCGG CCGAGCCGGA   240

GCCTGGGGAG GCGGCGGGGG CCCCGAGCGC AGCCCACGGC CCCCGCGCGG AGCCAGGCCC   300

GCTGCCGTCC CCGCCGCCCG CTCCCCCGGC ATGCAGCCCC GGCTGCGGAG GTGACACTTC   360

TGGGCTGTAG TCGCCACCGC CGCCTCCGCC ATCGCCACC ATG GAT GAA CAA GAG       414
                                            Met Asp Glu Gln Glu
                                              1               5

GCA TTA GAC TCG ATC ATG AAG GAC CTG GTG GCC CTC CAG ATG AGC CGA      462
```

```
Ala Leu Asp Ser Ile Met Lys Asp Leu Val Ala Leu Gln Met Ser Arg
            10                  15                  20

CGA ACC CGG TTG TCT GGA TAT GAG ACC ATG AAG AAT AAG GAC ACA GGT    510
Arg Thr Arg Leu Ser Gly Tyr Glu Thr Met Lys Asn Lys Asp Thr Gly
            25                  30                  35

CAC CCA AAC AGG CAG AGT GAC GTC AGA ATC AAG TTT GAA CAC AAT GGG    558
His Pro Asn Arg Gln Ser Asp Val Arg Ile Lys Phe Glu His Asn Gly
            40                  45                  50

GAG AGA CGA ATT ATA GCA TTC AGC CGG CCT GTG AGA TAC GAA GAT GTG    606
Glu Arg Arg Ile Ile Ala Phe Ser Arg Pro Val Arg Tyr Glu Asp Val
 55                  60                  65

GAG CAC AAG GTG ACA ACA GTC TTT GGG CAG CCT CTT GAT TTG CAT TAT    654
Glu His Lys Val Thr Thr Val Phe Gly Gln Pro Leu Asp Leu His Tyr
 70                  75                  80                  85

ATG AAT AAT GAG CTC TCC ATC CTG TTG AAA AAC CAA GAT GAT CTC GAT    702
Met Asn Asn Glu Leu Ser Ile Leu Leu Lys Asn Gln Asp Asp Leu Asp
            90                  95                 100

AAA GCC ATT GAC ATT TTG GAT AGA AGC TCA AGT ATG AAA AGC CTT AGG    750
Lys Ala Ile Asp Ile Leu Asp Arg Ser Ser Ser Met Lys Ser Leu Arg
           105                 110                 115

ATA CTA CTG TTA TCC CAA GAC AGA AAC CAT ACT AGT TCC TCT CCC CAC    798
Ile Leu Leu Leu Ser Gln Asp Arg Asn His Thr Ser Ser Ser Pro His
           120                 125                 130

TCT GGA GTG TCC AGG CAG GTT CGG ATC AAG CCT TCC CAG TCT GCA GGG    846
Ser Gly Val Ser Arg Gln Val Arg Ile Lys Pro Ser Gln Ser Ala Gly
           135                 140                 145

GAT ATA AAT ACC ATC TAC CAA GCT CCT GAG CCC AGA AGC AGG CAC CTG    894
Asp Ile Asn Thr Ile Tyr Gln Ala Pro Glu Pro Arg Ser Arg His Leu
150                 155                 160                 165

TCT GTC AGC TCC CAG AAC CCT GGC CGA AGC TCT CCT CCC CCG GGA TAT    942
Ser Val Ser Ser Gln Asn Pro Gly Arg Ser Ser Pro Pro Pro Gly Tyr
           170                 175                 180

GTA CCT GAG CGA CAA CAG CAC ATT GCC CGG CAA GGA TCC TAT ACG AGC    990
Val Pro Glu Arg Gln Gln His Ile Ala Arg Gln Gly Ser Tyr Thr Ser
           185                 190                 195

ATC AAC AGC GAA GGT GAA TTC ATC CCA GAG ACC AGC GAA CAG TGT ATG   1038
Ile Asn Ser Glu Gly Glu Phe Ile Pro Glu Thr Ser Glu Gln Cys Met
           200                 205                 210

CTA GAT CCC CTC AGC AGT GCC GAA AAT TCC TTG TCA GGA AGC TGC CAA   1086
Leu Asp Pro Leu Ser Ser Ala Glu Asn Ser Leu Ser Gly Ser Cys Gln
215                 220                 225

TCC TTG GAC AGG TCA GCA GAC AGC CCA TCC TTC AGG AAA TCA CAA ATG   1134
Ser Leu Asp Arg Ser Ala Asp Ser Pro Ser Phe Arg Lys Ser Gln Met
230                 235                 240                 245

TCC CGA GCC CGG AGC TTC CCA GAC AAC AGA AAG GAA TGC TCA GAT CGG   1182
Ser Arg Ala Arg Ser Phe Pro Asp Asn Arg Lys Glu Cys Ser Asp Arg
           250                 255                 260

GAG ACC CAG CTC TAT GAT AAA GGT GTC AAA GGT GGA ACC TAT CCC AGG   1230
Glu Thr Gln Leu Tyr Asp Lys Gly Val Lys Gly Gly Thr Tyr Pro Arg
           265                 270                 275

CGC TAC CAT GTG TCT GTG CAT CAC AAA GAC TAC AAT GAT GGC AGA AGA   1278
Arg Tyr His Val Ser Val His His Lys Asp Tyr Asn Asp Gly Arg Arg
           280                 285                 290

ACA TTT CCC CGA ATA CGA CGG CAT CAA GGC AAC CTA TTC ACT CTG GTG   1326
Thr Phe Pro Arg Ile Arg Arg His Gln Gly Asn Leu Phe Thr Leu Val
           295                 300                 305

CCC TCA AGT CGC TCC TTG AGC ACA AAT GGC GAG AAC ATG GGT GTA GCT   1374
Pro Ser Ser Arg Ser Leu Ser Thr Asn Gly Glu Asn Met Gly Val Ala
310                 315                 320                 325

GTG CAA TAC CTG GAC CCC CGT GGG CGC CTA CGG AGT GCA GAC AGT GAG   1422
```

```
             Val Gln Tyr Leu Asp Pro Arg Gly Arg Leu Arg Ser Ala Asp Ser Glu
                             330                 335                 340

AAT GCC CTC ACT GTG CAG GAA AGG AAT GTG CCA ACC AAA TCT CCT AGT             1470
Asn Ala Leu Thr Val Gln Glu Arg Asn Val Pro Thr Lys Ser Pro Ser
            345                 350                 355

GCT CCC ATC AAT TGG CGT CGG GGG AAG CTC CTG GGT CAA GGT GCC TTC             1518
Ala Pro Ile Asn Trp Arg Arg Gly Lys Leu Leu Gly Gln Gly Ala Phe
        360                 365                 370

GGC AGG GTC TAC TTG TGC TAT GAT GTG GAC ACA GGA CGT GAA CTT GCT             1566
Gly Arg Val Tyr Leu Cys Tyr Asp Val Asp Thr Gly Arg Glu Leu Ala
    375                 380                 385

TCT AAG CAG GTC CAG TTT GAC CCA GAT AGT CCT GAG ACA AGC AAG GAG             1614
Ser Lys Gln Val Gln Phe Asp Pro Asp Ser Pro Glu Thr Ser Lys Glu
390                 395                 400                 405

GTG AGT GCT CTG GAG TGT GAG ATC CAG TTG CTG AAG AAC CTG CAG CAT             1662
Val Ser Ala Leu Glu Cys Glu Ile Gln Leu Leu Lys Asn Leu Gln His
                410                 415                 420

GAG CGC ATT GTG CAG TAC TAC GGC TGC CTG CGG GAC CGT GCT GAG AAG             1710
Glu Arg Ile Val Gln Tyr Tyr Gly Cys Leu Arg Asp Arg Ala Glu Lys
            425                 430                 435

ATC CTC ACC ATC TTT ATG GAG TAT ATG CCA GGG GGC TCT GTA AAA GAC             1758
Ile Leu Thr Ile Phe Met Glu Tyr Met Pro Gly Gly Ser Val Lys Asp
        440                 445                 450

CAG TTG AAG GCC TAC GGA GCT CTG ACA GAG AGT GTG ACC CGC AAG TAC             1806
Gln Leu Lys Ala Tyr Gly Ala Leu Thr Glu Ser Val Thr Arg Lys Tyr
    455                 460                 465

ACC CGG CAG ATT CTG GAG GGC ATG TCA TAC CTG CAC AGC AAC ATG ATT             1854
Thr Arg Gln Ile Leu Glu Gly Met Ser Tyr Leu His Ser Asn Met Ile
470                 475                 480                 485

GTG CAT CGG GAC ATC AAG GGA GCC AAT ATC CTC CGA GAC TCA GCT GGG             1902
Val His Arg Asp Ile Lys Gly Ala Asn Ile Leu Arg Asp Ser Ala Gly
                490                 495                 500

AAT GTG AAG CTT GGG GAT TTT GGG GCC AGC AAA CGC CTA CAG ACC ATC             1950
Asn Val Lys Leu Gly Asp Phe Gly Ala Ser Lys Arg Leu Gln Thr Ile
            505                 510                 515

TGC ATG TCA GGG ACA GGC ATT CGC TCT GTC ACT GGC ACA CCC TAC TGG             1998
Cys Met Ser Gly Thr Gly Ile Arg Ser Val Thr Gly Thr Pro Tyr Trp
        520                 525                 530

ATG AGT CCT GAA GTC ATC AGT GGC GAG GGC TAT GGA AGA AAG GCA GAC             2046
Met Ser Pro Glu Val Ile Ser Gly Glu Gly Tyr Gly Arg Lys Ala Asp
    535                 540                 545

GTG TGG AGC CTG GGC TGT ACT GTG GTG GAA ATG CTG ACA GAG AAA CCA             2094
Val Trp Ser Leu Gly Cys Thr Val Val Glu Met Leu Thr Glu Lys Pro
550                 555                 560                 565

CCT TGG GCA GAG TAT GAA GCT ATG GCT GCC ATT TTC AAG ATT GCC ACC             2142
Pro Trp Ala Glu Tyr Glu Ala Met Ala Ala Ile Phe Lys Ile Ala Thr
                570                 575                 580

CAG CCT ACC AAT CCT CAG CTG CCC TCT CAC ATC TCA GAA CAC GGC AGG             2190
Gln Pro Thr Asn Pro Gln Leu Pro Ser His Ile Ser Glu His Gly Arg
            585                 590                 595

GAC TTC CTG AGG CGC ATA TTT GTG GAA GCT CGT CAG AGA CCC TCA GCT             2238
Asp Phe Leu Arg Arg Ile Phe Val Glu Ala Arg Gln Arg Pro Ser Ala
        600                 605                 610

GAG GAG CTG CTC ACA CAC CAC TTT GCA CAG CTA GTG TAC TGAGCTCTCA              2287
Glu Glu Leu Leu Thr His His Phe Ala Gln Leu Val Tyr
    615                 620                 625

AGGCTATCAG GCTGCCAGCT GCCACCTGCT GAGCAGGCAA GGGGCTGCTG TCAGGCTCAG           2347

TGAAGTTGCT GCTTCTTCCA GGCAAGGCTA TGACCAGTGG AGCATCGGTC CAGCCATTGT           2407

TTGTCTGTGC CCCATCTGCC ACTGGGACTC AAAGCCAGGA TGGGATAGCT CTGGCATCAA           2467
```

```
GACTGGGAGC TCCAGCCTGT AAGACCCAAG AGCTTTAGCA CCTTAAGCTC AGTATGGCGG     2527

GAAGGGCTGG AAACAGTATG CAAGACTGCC ATGGGTCCTG CCTACCCTCA GATGTGTCCT     2587

AACACTGCAG ACAGCACTGA AGTCAAGAGG GACTGGGGCA CAGGAGGTCC TCAAGGGTAT     2647

GAATAGTGTT ACTTCATTCA GAGTGTTACT TTGTTTCTCT CCCAATGTTT GGAGACCACC     2707

AGCCTGTCTC TGGGCTGCAA GCCTGAGGTA AAGCCCAGCA TCCCCCAGCC AACAGAAGGT     2767

AGAGGTTTGG GCTACCCCAC TATAGCTTCC AGGTATTCGG TGTCAGTCCT GTCTTACCAA     2827

AGATGAATGA AGCAAATGTT ACACTGCCTT ATTCTGGGAA GGAGGAGCTA CTCGGATAAG     2887

CAGGGCCTGA GAGATGGAGC TGCCTCCAGA AACTGGGGAG ACCCAGTCTT GTCAATGCAA     2947

TTGTCTCTGT TTTACAAGTT GGAGTCACTC TTATGCTGTT CCCAGTTTTA AAACTGGAGA     3007

CTTTGCCCTC TGAGCTCTGG AGACCCATGT GGGCTTAGGC TTGGACTGGA TGGAAGAGCT     3067

GATGGCCTCT GCCCCTGGCC TG                                             3089
```

(2) INFORMATION FOR SEQ ID NO:6:

(i) SEQUENCE CHARACTERISTICS:
        (A) LENGTH: 626 amino acids
        (B) TYPE: amino acid
        (D) TOPOLOGY: linear (ii) MOLECULE TYPE: protein (xi) SEQUENCE DESCRIPTION: SEQ ID NO:6:

```
Met Asp Glu Gln Glu Ala Leu Asp Ser Ile Met Lys Asp Leu Val Ala
 1               5                  10                  15

Leu Gln Met Ser Arg Arg Thr Arg Leu Ser Gly Tyr Glu Thr Met Lys
                20                  25                  30

Asn Lys Asp Thr Gly His Pro Asn Arg Gln Ser Asp Val Arg Ile Lys
            35                  40                  45

Phe Glu His Asn Gly Glu Arg Arg Ile Ile Ala Phe Ser Arg Pro Val
        50                  55                  60

Arg Tyr Glu Asp Val Glu His Lys Val Thr Thr Val Phe Gly Gln Pro
    65                  70                  75                  80

Leu Asp Leu His Tyr Met Asn Asn Glu Leu Ser Ile Leu Lys Asn
                85                  90                  95

Gln Asp Asp Leu Asp Lys Ala Ile Asp Ile Leu Asp Arg Ser Ser Ser
               100                 105                 110

Met Lys Ser Leu Arg Ile Leu Leu Ser Gln Asp Arg Asn His Thr
               115                 120                 125

Ser Ser Ser Pro His Ser Gly Val Ser Arg Gln Val Arg Ile Lys Pro
130                 135                 140

Ser Gln Ser Ala Gly Asp Ile Asn Thr Ile Tyr Gln Ala Pro Glu Pro
145                 150                 155                 160

Arg Ser Arg His Leu Ser Val Ser Ser Gln Asn Pro Gly Arg Ser Ser
               165                 170                 175

Pro Pro Pro Gly Tyr Val Pro Glu Arg Gln Gln His Ile Ala Arg Gln
               180                 185                 190

Gly Ser Tyr Thr Ser Ile Asn Ser Glu Gly Glu Phe Ile Pro Glu Thr
               195                 200                 205

Ser Glu Gln Cys Met Leu Asp Pro Leu Ser Ser Ala Glu Asn Ser Leu
    210                 215                 220

Ser Gly Ser Cys Gln Ser Leu Asp Arg Ser Ala Asp Ser Pro Ser Phe
225                 230                 235                 240
```

```
Arg Lys Ser Gln Met Ser Arg Ala Arg Ser Phe Pro Asp Asn Arg Lys
            245                 250                 255

Glu Cys Ser Asp Arg Glu Thr Gln Leu Tyr Asp Lys Gly Val Lys Gly
        260                 265                 270

Gly Thr Tyr Pro Arg Arg Tyr His Val Ser Val His His Lys Asp Tyr
                275                 280                 285

Asn Asp Gly Arg Arg Thr Phe Pro Arg Ile Arg Arg His Gln Gly Asn
            290                 295                 300

Leu Phe Thr Leu Val Pro Ser Ser Arg Ser Leu Ser Thr Asn Gly Glu
305                 310                 315                 320

Asn Met Gly Val Ala Val Gln Tyr Leu Asp Pro Arg Gly Arg Leu Arg
                325                 330                 335

Ser Ala Asp Ser Glu Asn Ala Leu Thr Val Gln Glu Arg Asn Val Pro
            340                 345                 350

Thr Lys Ser Pro Ser Ala Pro Ile Asn Trp Arg Arg Gly Lys Leu Leu
        355                 360                 365

Gly Gln Gly Ala Phe Gly Arg Val Tyr Leu Cys Tyr Asp Val Asp Thr
    370                 375                 380

Gly Arg Glu Leu Ala Ser Lys Gln Val Gln Phe Asp Pro Asp Ser Pro
385                 390                 395                 400

Glu Thr Ser Lys Glu Val Ser Ala Leu Glu Cys Glu Ile Gln Leu Leu
                405                 410                 415

Lys Asn Leu Gln His Glu Arg Ile Val Gln Tyr Tyr Gly Cys Leu Arg
            420                 425                 430

Asp Arg Ala Glu Lys Ile Leu Thr Ile Phe Met Glu Tyr Met Pro Gly
        435                 440                 445

Gly Ser Val Lys Asp Gln Leu Lys Ala Tyr Gly Ala Leu Thr Glu Ser
    450                 455                 460

Val Thr Arg Lys Tyr Thr Arg Gln Ile Leu Glu Gly Met Ser Tyr Leu
465                 470                 475                 480

His Ser Asn Met Ile Val His Arg Asp Ile Lys Gly Ala Asn Ile Leu
                485                 490                 495

Arg Asp Ser Ala Gly Asn Val Lys Leu Gly Asp Phe Gly Ala Ser Lys
            500                 505                 510

Arg Leu Gln Thr Ile Cys Met Ser Gly Thr Gly Ile Arg Ser Val Thr
        515                 520                 525

Gly Thr Pro Tyr Trp Met Ser Pro Glu Val Ile Ser Gly Glu Gly Tyr
    530                 535                 540

Gly Arg Lys Ala Asp Val Trp Ser Leu Gly Cys Thr Val Val Glu Met
545                 550                 555                 560

Leu Thr Glu Lys Pro Pro Trp Ala Glu Tyr Glu Ala Met Ala Ala Ile
                565                 570                 575

Phe Lys Ile Ala Thr Gln Pro Thr Asn Pro Gln Leu Pro Ser His Ile
            580                 585                 590

Ser Glu His Gly Arg Asp Phe Leu Arg Arg Ile Phe Val Glu Ala Arg
        595                 600                 605

Gln Arg Pro Ser Ala Glu Glu Leu Leu Thr His His Phe Ala Gln Leu
    610                 615                 620

Val Tyr
625
```

(2) INFORMATION FOR SEQ ID NO:7:

(i) SEQUENCE CHARACTERISTICS:
        (A) LENGTH: 3913 base pairs (B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 747..3417
(A) NAME/KEY: N = G,A,C or T
(B) LOCATION: 1094
(A) NAME/KEY: Xaa = Any amino acid
(B) LOCATION: 116

(xi) SEQUENCE DESCRIPTION: SEQ ID NO:7:

```
AATTCGGCAC GAGAACCTAT CAGACATTGG CTGGCCAGTG TTTGAAATCC CCTCCCCTCG      60

GCCGTCCAAG GGCTACGAGC CAGAGGACGA GGTCGAGGAC ACGGAGGTTG AGCTGAGGGA     120

GCTGGAGAGC GGGACGGAGG AGAGTGACGA GGAGCCAACC CCCAGTCCGA GGGTGCCAGA     180

GCTCAGGCTG TCCACAGACA CCATCTTGGA CAGTCGCTCC CAGGGCTGCG TCTCCAGGAA     240

GCTGGAGAGG CTCGAGTCAG AGGAAGATTC CATAGGCTGG GGGACAGCGG ACTGTGGCCC     300

TGAAGCCAGC AGGCATTGTT TGACTTCTAT CTATAGACCA TTCGTGGACA AAGCACTGAA     360

GCAAATGGGG CTAAGAAAGT TAATTTTACG ACTTCATAAG CTTATGAATG GGTCCTTGCA     420

AAGAGCTCGT GTAGCTCTGG TGAAGGACGA CCGTCAGTGT AGTTCTCTGA CTTTCCAGGT     480

CCCATGTGGG GCTCGGATTA TGTGCAGTTG TCGGGAACAC CTCCTTCCTC AGAGCAGAAG     540

TGTAGCGCTG TGTCCTGGGA AGAACTGAGA GCCATGGACC TGCCTTCCTT TGAGCCCGCC     600

TTCCTGGTGC TCTGTCGGGT CCTGCTGAAC GTGATCCACG AGTGCCTGAA GCTGCGGCTG     660

GAACAGAGGC TGCCGGGGAG CCTTCCCTCT TGAGTATCAA ACAGCTAGTG CGAGAGTGTA     720

AAGAGGTCCT AAAGGGCGGG CTCCTG ATG AAG CAG TAT TAC CAG TTC ATG CTG     773
                              Met Lys Gln Tyr Tyr Gln Phe Met Leu
                                1               5

CAG GAG GTC CTG GGC GGA CTG GAG AAG ACC GAC TGC AAC ATG GAT GCC     821
Gln Glu Val Leu Gly Gly Leu Glu Lys Thr Asp Cys Asn Met Asp Ala
 10              15                  20                  25

TTT GAG GAG GAC CTG CAG AAG ATG CTG ATG GTG TAT TTT GAT TAC ATG     869
Phe Glu Glu Asp Leu Gln Lys Met Leu Met Val Tyr Phe Asp Tyr Met
                 30                  35                  40

AGA AGC TGG ATC CAA ATG CTA CAG CAG TTA CCT CAG GCT TCC CAT AGC     917
Arg Ser Trp Ile Gln Met Leu Gln Gln Leu Pro Gln Ala Ser His Ser
                 45                  50                  55

TTA AAA AAC CTG CTA GAA GAG GAA TGG AAT TTC ACC AAA GAA ATA ACC     965
Leu Lys Asn Leu Leu Glu Glu Glu Trp Asn Phe Thr Lys Glu Ile Thr
                 60                  65                  70

CAT TAT ATC CGT GGC GGA GAA GCG CAG GCT GGA AAG CTT TTC TGT GAC    1013
His Tyr Ile Arg Gly Gly Glu Ala Gln Ala Gly Lys Leu Phe Cys Asp
         75                  80                  85

ATC GCA GGG ATG CTG CTA AAA TCC ACA GGG AGC TTT CTG GAA TCC GGC    1061
Ile Ala Gly Met Leu Leu Lys Ser Thr Gly Ser Phe Leu Glu Ser Gly
 90                  95                 100                 105

CTG CAG GAG AGC TGT GCT GAG CTG TGG ACC AGN GCC GAC GAC AAC GGT    1109
Leu Gln Glu Ser Cys Ala Glu Leu Trp Thr Xaa Ala Asp Asp Asn Gly
                110                 115                 120

GCT GCC GAC GAG CTA AGG AGA TCT GTC ATC GAG ATC AGC CGA GCA CTC    1157
Ala Ala Asp Glu Leu Arg Arg Ser Val Ile Glu Ile Ser Arg Ala Leu
                125                 130                 135

AAG GAG CTC TTC CAC GAA GCC AGG GAA AGA GCC TCC AAG GCC CTG GGC    1205
Lys Glu Leu Phe His Glu Ala Arg Glu Arg Ala Ser Lys Ala Leu Gly
                140                 145                 150
```

```
TTT GCT AAA ATG CTG AGG AAG GAC CTA GAA ATA GCA GCA GAG TTC GTG        1253
Phe Ala Lys Met Leu Arg Lys Asp Leu Glu Ile Ala Ala Glu Phe Val
    155                 160                 165

CTA TCT GCA TCA GCC CGA GAG CTC CTG GAC GCT CTG AAA GCA AAG CAG        1301
Leu Ser Ala Ser Ala Arg Glu Leu Leu Asp Ala Leu Lys Ala Lys Gln
170                 175                 180                 185

TAT GTT AAG GTA CAG ATT CCC GGG TTA GAG AAT TTG CAC GTG TTT GTC        1349
Tyr Val Lys Val Gln Ile Pro Gly Leu Glu Asn Leu His Val Phe Val
                190                 195                 200

CCC GAC AGC CTC GCT GAG GAG AAG AAA ATT ATT TTG CAG CTA CTC AAT        1397
Pro Asp Ser Leu Ala Glu Glu Lys Lys Ile Ile Leu Gln Leu Leu Asn
            205                 210                 215

GCT GCC ACA GGA AAG GAC TGC TCA AAG GAT CCA GAC GAC GTC TTC ATG        1445
Ala Ala Thr Gly Lys Asp Cys Ser Lys Asp Pro Asp Asp Val Phe Met
        220                 225                 230

GAT GCC TTC CTG CTC CTG ACC AAG CAT GGG GAC CGA GCC CGT GAC TCA        1493
Asp Ala Phe Leu Leu Leu Thr Lys His Gly Asp Arg Ala Arg Asp Ser
    235                 240                 245

GAA GAT GGC TGG GGC ACA TGG GAA GCT CGG GCT GTC AAA ATT GTG CCT        1541
Glu Asp Gly Trp Gly Thr Trp Glu Ala Arg Ala Val Lys Ile Val Pro
250                 255                 260                 265

CAG GTG GAG ACT GTG GAC ACC CTG AGA AGC ATG CAG GTG GAC AAC CTT        1589
Gln Val Glu Thr Val Asp Thr Leu Arg Ser Met Gln Val Asp Asn Leu
                270                 275                 280

CTG CTG GTT GTC ATG GAG TCT GCT CAC CTC GTA CTT CAG AGA AAA GCC        1637
Leu Leu Val Val Met Glu Ser Ala His Leu Val Leu Gln Arg Lys Ala
            285                 290                 295

TTC CAG CAG TCC ATT GAG GGG CTG ATG ACT GTA CGC CAT GAG CAG ACA        1685
Phe Gln Gln Ser Ile Glu Gly Leu Met Thr Val Arg His Glu Gln Thr
        300                 305                 310

TCT AGC CAG CCC ATC ATC GCC AAA GGT TTG CAG CAG CTC AAG AAC GAT        1733
Ser Ser Gln Pro Ile Ile Ala Lys Gly Leu Gln Gln Leu Lys Asn Asp
    315                 320                 325

GCA CTT GAG CTA TGC AAC AGA ATC AGC GAT GCC ATC GAC CGT GTG GAC        1781
Ala Leu Glu Leu Cys Asn Arg Ile Ser Asp Ala Ile Asp Arg Val Asp
330                 335                 340                 345

CAC ATG TTC ACC CTG GAG TTC GAT GCT GAG GTC GAG GAG TCT GAG TCG        1829
His Met Phe Thr Leu Glu Phe Asp Ala Glu Val Glu Glu Ser Glu Ser
                350                 355                 360

GCC ACG CTG CAG CAG TAC TAC CGA GAA GCC ATG ATT CAG GGC TAC AAC        1877
Ala Thr Leu Gln Gln Tyr Tyr Arg Glu Ala Met Ile Gln Gly Tyr Asn
            365                 370                 375

TTT GGG TTT GAG TAT CAT AAA GAA GTT GTT CGT TTG ATG TCT GGG GAA        1925
Phe Gly Phe Glu Tyr His Lys Glu Val Val Arg Leu Met Ser Gly Glu
        380                 385                 390

TTC AGG CAG AAG ATA GGA GAC AAA TAT ATA ACG TTC GCC CAG AAG TGG        1973
Phe Arg Gln Lys Ile Gly Asp Lys Tyr Ile Thr Phe Ala Gln Lys Trp
    395                 400                 405

ATG AAT TAC GTG CTG ACC AAA TGC GAG AGC GGC AGA GGC ACA AGA CCC        2021
Met Asn Tyr Val Leu Thr Lys Cys Glu Ser Gly Arg Gly Thr Arg Pro
410                 415                 420                 425

AGA TGG GCC ACC CAA GGA TTT GAT TTC CTA CAA GCC ATT GAA CCT GCC        2069
Arg Trp Ala Thr Gln Gly Phe Asp Phe Leu Gln Ala Ile Glu Pro Ala
                430                 435                 440

TTT ATT TCA GCT TTA CCA GAA GAT GAC TTC TTG AGT TTG CAA GCC CTG        2117
Phe Ile Ser Ala Leu Pro Glu Asp Asp Phe Leu Ser Leu Gln Ala Leu
            445                 450                 455

ATG AAT GAG TGC ATC GGG CAC GTC ATA GGA AAG CCA CAC AGC CCT GTC        2165
Met Asn Glu Cys Ile Gly His Val Ile Gly Lys Pro His Ser Pro Val
        460                 465                 470
```

```
ACA GCT ATC CAT CGG AAC AGC CCC CGC CCT GTG AAG GTG CCC CGA TGC          2213
Thr Ala Ile His Arg Asn Ser Pro Arg Pro Val Lys Val Pro Arg Cys
        475                 480                 485

CAC AGT GAC CCT CCT AAC CCT CAC CTC ATC ATC CCG ACT CCA GAG GGA          2261
His Ser Asp Pro Pro Asn Pro His Leu Ile Ile Pro Thr Pro Glu Gly
490                 495                 500                 505

TTC AGG GGT TCC AGT GTC CCT GAA AAC GAC CGC TTG GCC TCC ATA GCT          2309
Phe Arg Gly Ser Ser Val Pro Glu Asn Asp Arg Leu Ala Ser Ile Ala
                510                 515                 520

GCA GAA CTG CAG TTC AGG TCT CTG AGT CGG CAC TCA AGC CCC ACG GAA          2357
Ala Glu Leu Gln Phe Arg Ser Leu Ser Arg His Ser Ser Pro Thr Glu
            525                 530                 535

GAG CGA GAC GAG CCA GCG TAT CCT CGG AGT GAC TCA AGT GGA TCA ACT          2405
Glu Arg Asp Glu Pro Ala Tyr Pro Arg Ser Asp Ser Ser Gly Ser Thr
        540                 545                 550

CGG AGA AGC TGG GAA CTT CGA ACA CTC ATC AGC CAG ACC AAA GAC TCG          2453
Arg Arg Ser Trp Glu Leu Arg Thr Leu Ile Ser Gln Thr Lys Asp Ser
555                 560                 565

GCC TCT AAG CAG GGG CCC ATA GAA GCT ATC CAG AAG TCA GTC CGA CTG          2501
Ala Ser Lys Gln Gly Pro Ile Glu Ala Ile Gln Lys Ser Val Arg Leu
570                 575                 580                 585

TTT GAA GAG AGG AGG TAT CGA GAG ATG AGG AGA AAG AAT ATC ATC GGC          2549
Phe Glu Glu Arg Arg Tyr Arg Glu Met Arg Arg Lys Asn Ile Ile Gly
                590                 595                 600

CAA GTG TGC GAT ACC CCT AAG TCC TAT GAT AAC GTC ATG CAT GTT GGA          2597
Gln Val Cys Asp Thr Pro Lys Ser Tyr Asp Asn Val Met His Val Gly
            605                 610                 615

CTG AGG AAG GTG ACA TTT AAG TGG CAA AGA GGA AAC AAA ATT GGA GAA          2645
Leu Arg Lys Val Thr Phe Lys Trp Gln Arg Gly Asn Lys Ile Gly Glu
        620                 625                 630

GGA CAG TAT GGA AAA GTA TAC ACC TGC ATC AGT GTT GAC ACA GGG GAG          2693
Gly Gln Tyr Gly Lys Val Tyr Thr Cys Ile Ser Val Asp Thr Gly Glu
635                 640                 645

CTG ATG GCC ATG AAG GAG ATT CGA TTT CAG CCT AAC GAC CAC AAG ACT          2741
Leu Met Ala Met Lys Glu Ile Arg Phe Gln Pro Asn Asp His Lys Thr
650                 655                 660                 665

ATC AAG GAG ACT GCA GAC GAG TTG AAA ATA TTT GAA GGC ATC AAG CAC          2789
Ile Lys Glu Thr Ala Asp Glu Leu Lys Ile Phe Glu Gly Ile Lys His
                670                 675                 680

CCC AAC CTG GTC CGG TAT TTT GGC GTG GAG CTT CAC AGG GAA GAG ATG          2837
Pro Asn Leu Val Arg Tyr Phe Gly Val Glu Leu His Arg Glu Glu Met
            685                 690                 695

TAC ATC TTC ATG GAG TAC TGT GAT GAG GGT ACA CTA GAG GAG GTG TCA          2885
Tyr Ile Phe Met Glu Tyr Cys Asp Glu Gly Thr Leu Glu Glu Val Ser
        700                 705                 710

CGA CTG GGC CTG CAG GAG CAC GTC ATC AGG TTA TAT ACC AAG CAG ATC          2933
Arg Leu Gly Leu Gln Glu His Val Ile Arg Leu Tyr Thr Lys Gln Ile
715                 720                 725

ACT GTC GCC ATC AAC GTC CTC CAT GAG CAC GGC ATC GTT CAC CGA GAC          2981
Thr Val Ala Ile Asn Val Leu His Glu His Gly Ile Val His Arg Asp
730                 735                 740                 745

ATC AAA GGT GCC AAT ATC TTC CTT ACG TCA TCT GGA CTA ATC AAG CTG          3029
Ile Lys Gly Ala Asn Ile Phe Leu Thr Ser Ser Gly Leu Ile Lys Leu
                750                 755                 760

GGA GAT TTT GGA TGC TCT GTA AAA CTT AAA AAC AAC GCC CAG ACC ATG          3077
Gly Asp Phe Gly Cys Ser Val Lys Leu Lys Asn Asn Ala Gln Thr Met
            765                 770                 775

CCC GGA GAG GTG AAC AGC ACC CTA GGG ACA GCA GCT TAC ATG GCC CCT          3125
Pro Gly Glu Val Asn Ser Thr Leu Gly Thr Ala Ala Tyr Met Ala Pro
        780                 785                 790
```

```
GAA GTT ATT ACC CGA GCC AAA GGA GAA GGC CAC GGA CGT GCG GCA GAT       3173
Glu Val Ile Thr Arg Ala Lys Gly Glu Gly His Gly Arg Ala Ala Asp
    795                 800                 805

ATC TGG AGT CTG GGG TGC GTC GTC ATA GAG ATG GTG ACT GGC AAG CGG       3221
Ile Trp Ser Leu Gly Cys Val Val Ile Glu Met Val Thr Gly Lys Arg
810                 815                 820                 825

CCT TGG CAT GAG TAT GAA CAC AAC TTT CAG ATT ATG TAC AAG GTG GGG       3269
Pro Trp His Glu Tyr Glu His Asn Phe Gln Ile Met Tyr Lys Val Gly
                830                 835                 840

ATG GGA CAC AAG CCA CCA ATC CCG GAA AGG CTA AGC CCT GAA GGA AAG       3317
Met Gly His Lys Pro Pro Ile Pro Glu Arg Leu Ser Pro Glu Gly Lys
            845                 850                 855

GCC TTT CTC TCG CAC TGC CTG GAA AGT GAC CCG AAG ATA CGG TGG ACA       3365
Ala Phe Leu Ser His Cys Leu Glu Ser Asp Pro Lys Ile Arg Trp Thr
                860                 865                 870

GCC AGC CAG CTC CTC GAC CAC GCT TTT GTC AAG GTT TGC ACA GAT GAA       3413
Ala Ser Gln Leu Leu Asp His Ala Phe Val Lys Val Cys Thr Asp Glu
        875                 880                 885

GAG T GAAGTGAACC AGTCCGTGGC CTAGTAGTGT GTGGACAGAA TCCCGTGATC          3467
Glu
890

ACTACTGTAT GTAATATTTA CATAAAGACT GCAGCGCAGG CGGCCTTCCT AACCTCCCAG     3527

GACTGAAGAC TACAGGGGTG ACAAGCCTCA CTTCTGCTGC TCCTGTCGCC TGCTGAGTGA     3587

CAGTGCTGAG GTTAAAGGAG CCGCACGTTA AGTGCCATTA CTACTGTACA CGGCCACCGC     3647

CTCTGTCCCC TCCGACCCTC TCGTGACTGA GAACCAACCG TGTCATCAGC ACAGTGTTTT     3707

TGAGCTCCTG GGGTTCAGAA GAACATGTAG TGTTCCGGGG TGTCCGGGAC GTTTATTTCA     3767

ACCTCCTGGT CGTTGGCTCT GACTGTGGAG CCTCCTTGTT CGAAAGCTGC AGGTTTGTTA     3827

TGCAAAGGCT CGTAAGTGAA GCTGAAGAAA AGGTTCTTTT TCAATAAATG GTTTATTTTA     3887

GGAAAGCGAA AAAAAAAAAA AAAAAA                                          3913

(2) INFORMATION FOR SEQ ID NO:8:

(i) SEQUENCE CHARACTERISTICS:
        (A) LENGTH: 890 amino acids
        (B) TYPE: amino acid
        (D) TOPOLOGY: linear (ii) MOLECULE TYPE: protein (ix) FEATURE:
        (A) NAME/KEY: Xaa = Any amino acid
        (B) LOCATION: 116

(xi) SEQUENCE DESCRIPTION: SEQ ID NO:8:

Met Lys Gln Tyr Tyr Gln Phe Met Leu Gln Glu Val Leu Gly Gly Leu
1               5                   10                  15

Glu Lys Thr Asp Cys Asn Met Asp Ala Phe Glu Glu Asp Leu Gln Lys
            20                  25                  30

Met Leu Met Val Tyr Phe Asp Tyr Met Arg Ser Trp Ile Gln Met Leu
        35                  40                  45

Gln Gln Leu Pro Gln Ala Ser His Ser Leu Lys Asn Leu Leu Glu Glu
    50                  55                  60

Glu Trp Asn Phe Thr Lys Glu Ile Thr His Tyr Ile Arg Gly Gly Glu
65                  70                  75                  80

Ala Gln Ala Gly Lys Leu Phe Cys Asp Ile Ala Gly Met Leu Leu Lys
                85                  90                  95

Ser Thr Gly Ser Phe Leu Glu Ser Gly Leu Gln Glu Ser Cys Ala Glu
            100                 105                 110
```

```
Leu Trp Thr Xaa Ala Asp Asp Asn Gly Ala Ala Asp Glu Leu Arg Arg
            115                 120                 125

Ser Val Ile Glu Ile Ser Arg Ala Leu Lys Glu Leu Phe His Glu Ala
        130                 135                 140

Arg Glu Arg Ala Ser Lys Ala Leu Gly Phe Ala Lys Met Leu Arg Lys
145                 150                 155                 160

Asp Leu Glu Ile Ala Ala Glu Phe Val Leu Ser Ala Ser Ala Arg Glu
                165                 170                 175

Leu Leu Asp Ala Leu Lys Ala Lys Gln Tyr Val Lys Val Gln Ile Pro
            180                 185                 190

Gly Leu Glu Asn Leu His Val Phe Val Pro Asp Ser Leu Ala Glu Glu
        195                 200                 205

Lys Lys Ile Ile Leu Gln Leu Leu Asn Ala Ala Thr Gly Lys Asp Cys
210                 215                 220

Ser Lys Asp Pro Asp Asp Val Phe Met Asp Ala Phe Leu Leu Leu Thr
225                 230                 235                 240

Lys His Gly Asp Arg Ala Arg Asp Ser Glu Asp Gly Trp Gly Thr Trp
                245                 250                 255

Glu Ala Arg Ala Val Lys Ile Val Pro Gln Val Glu Thr Val Asp Thr
            260                 265                 270

Leu Arg Ser Met Gln Val Asp Asn Leu Leu Leu Val Val Met Glu Ser
        275                 280                 285

Ala His Leu Val Leu Gln Arg Lys Ala Phe Gln Gln Ser Ile Glu Gly
        290                 295                 300

Leu Met Thr Val Arg His Glu Gln Thr Ser Ser Gln Pro Ile Ile Ala
305                 310                 315                 320

Lys Gly Leu Gln Gln Leu Lys Asn Asp Ala Leu Glu Leu Cys Asn Arg
                325                 330                 335

Ile Ser Asp Ala Ile Asp Arg Val Asp His Met Phe Thr Leu Glu Phe
            340                 345                 350

Asp Ala Glu Val Glu Glu Ser Glu Ser Ala Thr Leu Gln Gln Tyr Tyr
        355                 360                 365

Arg Glu Ala Met Ile Gln Gly Tyr Asn Phe Gly Phe Glu Tyr His Lys
        370                 375                 380

Glu Val Val Arg Leu Met Ser Gly Glu Phe Arg Gln Lys Ile Gly Asp
385                 390                 395                 400

Lys Tyr Ile Thr Phe Ala Gln Lys Trp Met Asn Tyr Val Leu Thr Lys
                405                 410                 415

Cys Glu Ser Gly Arg Gly Thr Arg Pro Arg Trp Ala Thr Gln Gly Phe
            420                 425                 430

Asp Phe Leu Gln Ala Ile Glu Pro Ala Phe Ile Ser Ala Leu Pro Glu
        435                 440                 445

Asp Asp Phe Leu Ser Leu Gln Ala Leu Met Asn Glu Cys Ile Gly His
        450                 455                 460

Val Ile Gly Lys Pro His Ser Pro Val Thr Ala Ile His Arg Asn Ser
465                 470                 475                 480

Pro Arg Pro Val Lys Val Pro Arg Cys His Ser Asp Pro Asn Pro
                485                 490                 495

His Leu Ile Ile Pro Thr Pro Glu Gly Phe Arg Gly Ser Ser Val Pro
            500                 505                 510

Glu Asn Asp Arg Leu Ala Ser Ile Ala Ala Glu Leu Gln Phe Arg Ser
        515                 520                 525

Leu Ser Arg His Ser Ser Pro Thr Glu Glu Arg Asp Glu Pro Ala Tyr
```

```
            530                 535                 540
Pro Arg Ser Asp Ser Ser Gly Ser Thr Arg Arg Ser Trp Glu Leu Arg
545                 550                 555                 560

Thr Leu Ile Ser Gln Thr Lys Asp Ser Ala Ser Lys Gln Gly Pro Ile
                565                 570                 575

Glu Ala Ile Gln Lys Ser Val Arg Leu Phe Glu Glu Arg Arg Tyr Arg
            580                 585                 590

Glu Met Arg Arg Lys Asn Ile Ile Gly Gln Val Cys Asp Thr Pro Lys
        595                 600                 605

Ser Tyr Asp Asn Val Met His Val Gly Leu Arg Lys Val Thr Phe Lys
610                 615                 620

Trp Gln Arg Gly Asn Lys Ile Gly Glu Gly Gln Tyr Gly Lys Val Tyr
625                 630                 635                 640

Thr Cys Ile Ser Val Asp Thr Gly Glu Leu Met Ala Met Lys Glu Ile
                645                 650                 655

Arg Phe Gln Pro Asn Asp His Lys Thr Ile Lys Glu Thr Ala Asp Glu
                    660                 665                 670

Leu Lys Ile Phe Glu Gly Ile Lys His Pro Asn Leu Val Arg Tyr Phe
            675                 680                 685

Gly Val Glu Leu His Arg Glu Glu Met Tyr Ile Phe Met Glu Tyr Cys
690                 695                 700

Asp Glu Gly Thr Leu Glu Glu Val Ser Arg Leu Gly Leu Gln Glu His
705                 710                 715                 720

Val Ile Arg Leu Tyr Thr Lys Gln Ile Thr Val Ala Ile Asn Val Leu
                725                 730                 735

His Glu His Gly Ile Val His Arg Asp Ile Lys Gly Ala Asn Ile Phe
                    740                 745                 750

Leu Thr Ser Ser Gly Leu Ile Lys Leu Gly Asp Phe Gly Cys Ser Val
            755                 760                 765

Lys Leu Lys Asn Asn Ala Gln Thr Met Pro Gly Glu Val Asn Ser Thr
770                 775                 780

Leu Gly Thr Ala Ala Tyr Met Ala Pro Glu Val Ile Thr Arg Ala Lys
785                 790                 795                 800

Gly Glu Gly His Gly Arg Ala Ala Asp Ile Trp Ser Leu Gly Cys Val
                805                 810                 815

Val Ile Glu Met Val Thr Gly Lys Arg Pro Trp His Glu Tyr Glu His
                    820                 825                 830

Asn Phe Gln Ile Met Tyr Lys Val Gly Met Gly His Lys Pro Pro Ile
            835                 840                 845

Pro Glu Arg Leu Ser Pro Glu Gly Lys Ala Phe Leu Ser His Cys Leu
850                 855                 860

Glu Ser Asp Pro Lys Ile Arg Trp Thr Ala Ser Gln Leu Leu Asp His
865                 870                 875                 880

Ala Phe Val Lys Val Cys Thr Asp Glu Glu
                885                 890

(2) INFORMATION FOR SEQ ID NO:9:

(i) SEQUENCE CHARACTERISTICS:
        (A) LENGTH: 4592 base pairs
        (B) TYPE: nucleic acid
        (C) STRANDEDNESS: double
        (D) TOPOLOGY: linear (ii) MOLECULE TYPE: cDNA (ix) FEATURE:
```

(A) NAME/KEY: CDS
(B) LOCATION: 355..4095

(xi) SEQUENCE DESCRIPTION: SEQ ID NO:9:

```
AAGAAGAAGG ACAGGGAGCA GAGGGACAA GAAAACACGG CTGCTTTCTG GTTCAACCGA        60

TCGAACGAAC TGATCTGGTT AGAACTGCAG GCCTGGCACG CGGGCCGCAC CATCAATGAC       120

CAGGACCTCT TTCTCTACAC AGCCCGCCAG GCCATCCCAG ACATCATCAA TGAGATCCTC       180

ACCTTCAAAG TTAACTACGG GAGCATTGCC TTCTCCAGCA ATGGAGCCGG TTTCAACGGG       240

CCCTTGGTAG AAGGCCAGTG CAGAACCCCT CAGGAGACAA ACCGTGTGGG CTGCTCATCG       300

TACCACGAGC ACCTCCAGCG CCAGAGGGTC TCGTTTGAGC AGGTGAAGCG GATA ATG        357
                                                              Met
                                                                1
```

| | | | | | | | | | | | | | | | | |
|---|---|---|---|---|---|---|---|---|---|---|---|---|---|---|---|---|
| GAG | CTG | CTG | GAG | TAC | ATG | GAG | GCA | CTT | TAC | CCA | TCC | TTG | CAG | GCT | CTG | 405 |
| Glu | Leu | Leu | Glu | Tyr | Met | Glu | Ala | Leu | Tyr | Pro | Ser | Leu | Gln | Ala | Leu | |
| | | | 5 | | | | 10 | | | | | 15 | | | | |
| CAG | AAG | GAC | TAT | GAA | CGG | TAC | GCC | GCC | AAG | GAC | TTT | GAG | GAC | AGA | GTG | 453 |
| Gln | Lys | Asp | Tyr | Glu | Arg | Tyr | Ala | Ala | Lys | Asp | Phe | Glu | Asp | Arg | Val | |
| | | 20 | | | | 25 | | | | 30 | | | | | | |
| CAG | GCG | CTC | TGC | CTG | TGG | CTC | AAC | ATC | ACG | AAA | GAT | CTA | AAT | CAG | AAG | 501 |
| Gln | Ala | Leu | Cys | Leu | Trp | Leu | Asn | Ile | Thr | Lys | Asp | Leu | Asn | Gln | Lys | |
| | 35 | | | | 40 | | | | 45 | | | | | | | |
| CTG | CGG | ATC | ATG | GGC | ACC | GTG | CTG | GGC | ATC | AAG | TTC | CTA | TCA | GAC | ATT | 549 |
| Leu | Arg | Ile | Met | Gly | Thr | Val | Leu | Gly | Ile | Lys | Phe | Leu | Ser | Asp | Ile | |
| 50 | | | | 55 | | | | 60 | | | | | 65 | | | |
| GGC | TGG | CCA | GTG | AAA | GAA | ATC | CCC | TCC | CCT | CGG | CCG | TCC | AAG | GGC | TAC | 597 |
| Gly | Trp | Pro | Val | Lys | Glu | Ile | Pro | Ser | Pro | Arg | Pro | Ser | Lys | Gly | Tyr | |
| | | | 70 | | | | 75 | | | | 80 | | | | | |
| GAG | CCA | GAG | GAC | GAG | GTC | GAG | GAC | ACG | GAG | GTT | GAG | CTG | AGG | GAG | CTG | 645 |
| Glu | Pro | Glu | Asp | Glu | Val | Glu | Asp | Thr | Glu | Val | Glu | Leu | Arg | Glu | Leu | |
| | | | | 85 | | | | 90 | | | | 95 | | | | |
| GAG | AGC | GGG | ACG | GAG | GAG | AGT | GAC | GAG | GAG | CCA | ACC | CCC | AGT | CCG | AGG | 693 |
| Glu | Ser | Gly | Thr | Glu | Glu | Ser | Asp | Glu | Glu | Pro | Thr | Pro | Ser | Pro | Arg | |
| | | 100 | | | | 105 | | | | 110 | | | | | | |
| GTG | CCA | GAG | CTC | AGG | CTG | TCC | ACA | GAC | ACC | ATC | TTG | GAC | AGT | CGC | TCC | 741 |
| Val | Pro | Glu | Leu | Arg | Leu | Ser | Thr | Asp | Thr | Ile | Leu | Asp | Ser | Arg | Ser | |
| | 115 | | | | 120 | | | | 125 | | | | | | | |
| CAG | GGC | TGC | GTC | TCC | AGG | AAG | CTG | GAG | AGG | CTC | GAG | TCA | GAG | GAA | GAT | 789 |
| Gln | Gly | Cys | Val | Ser | Arg | Lys | Leu | Glu | Arg | Leu | Glu | Ser | Glu | Glu | Asp | |
| 130 | | | | 135 | | | | 140 | | | | 145 | | | | |
| TCC | ATA | GGC | TGG | GGG | ACA | GCG | GAC | TGT | GGC | CCT | GAA | GCC | AGC | AGG | CAT | 837 |
| Ser | Ile | Gly | Trp | Gly | Thr | Ala | Asp | Cys | Gly | Pro | Glu | Ala | Ser | Arg | His | |
| | | | 150 | | | | 155 | | | | 160 | | | | | |
| TGT | TTG | ACT | TCT | ATG | TAT | AGA | CCA | TTC | GTG | GAC | AAA | GCA | CTG | AAG | CAA | 885 |
| Cys | Leu | Thr | Ser | Met | Tyr | Arg | Pro | Phe | Val | Asp | Lys | Ala | Leu | Lys | Gln | |
| | | | 165 | | | | 170 | | | | 175 | | | | | |
| ATG | GGG | CTA | AGA | AAG | TTA | ATT | TTA | CGA | CTT | CAT | AAG | CTT | ATG | AAT | GGG | 933 |
| Met | Gly | Leu | Arg | Lys | Leu | Ile | Leu | Arg | Leu | His | Lys | Leu | Met | Asn | Gly | |
| | | 180 | | | | 185 | | | | 190 | | | | | | |
| TCC | TTG | CAA | AGA | GCT | CGT | GTA | GCT | CTG | GTG | AAG | GAC | GAC | CGT | CCA | GTG | 981 |
| Ser | Leu | Gln | Arg | Ala | Arg | Val | Ala | Leu | Val | Lys | Asp | Asp | Arg | Pro | Val | |
| | 195 | | | | 200 | | | | 205 | | | | | | | |
| GAG | TTC | TCT | GAC | TTT | CCA | GGT | CCC | ATG | TGG | GGC | TCG | GAT | TAT | GTG | CAG | 1029 |
| Glu | Phe | Ser | Asp | Phe | Pro | Gly | Pro | Met | Trp | Gly | Ser | Asp | Tyr | Val | Gln | |
| 210 | | | | 215 | | | | 220 | | | | 225 | | | | |
| TTG | TCG | GGA | ACA | CCT | CCT | TCC | TCA | GAG | CAG | AAG | TGT | AGC | GCT | GTG | TCC | 1077 |
| Leu | Ser | Gly | Thr | Pro | Pro | Ser | Ser | Glu | Gln | Lys | Cys | Ser | Ala | Val | Ser | |
| | | | 230 | | | | 235 | | | | 240 | | | | | |
| TGG | GAA | GAA | CTG | AGA | GCC | ATG | GAC | CTG | CCT | TCC | TTT | GAG | CCC | GCC | TTC | 1125 |

```
                                                          -continued

Trp Glu Glu Leu Arg Ala Met Asp Leu Pro Ser Phe Glu Pro Ala Phe
                    245                 250                 255

CTG GTG CTC TGT CGG GTC CTG CTG AAC GTG ATC CAC GAG TGC CTG AAG      1173
Leu Val Leu Cys Arg Val Leu Leu Asn Val Ile His Glu Cys Leu Lys
            260                 265                 270

CTG CGG CTG GAA CAG AGG CCT GCC GGG GAG CCT TCC CTC TTG AGT ATC      1221
Leu Arg Leu Glu Gln Arg Pro Ala Gly Glu Pro Ser Leu Leu Ser Ile
275                 280                 285

AAA CAG CTA GTG CGA GAG TGT AAA GAG GTC CTA AAG GGC GGG CTC CTG      1269
Lys Gln Leu Val Arg Glu Cys Lys Glu Val Leu Lys Gly Gly Leu Leu
290                 295                 300                 305

ATG AAG CAG TAT TAC CAG TTC ATG CTG CAG GAG GTC CTG GGC GGA CTG      1317
Met Lys Gln Tyr Tyr Gln Phe Met Leu Gln Glu Val Leu Gly Gly Leu
                310                 315                 320

GAG AAG ACC GAC TGC AAC ATG GAT GCC TTT GAG GAG GAC CTG CAG AAG      1365
Glu Lys Thr Asp Cys Asn Met Asp Ala Phe Glu Glu Asp Leu Gln Lys
            325                 330                 335

ATG CTG ATG GTG TAT TTT GAT TAC ATG AGA AGC TGG ATC CAA ATG CTA      1413
Met Leu Met Val Tyr Phe Asp Tyr Met Arg Ser Trp Ile Gln Met Leu
        340                 345                 350

CAG CAG TTA CCT CAG GCT TCC CAT AGC TTA AAA AAC CTG CTA GAA GAG      1461
Gln Gln Leu Pro Gln Ala Ser His Ser Leu Lys Asn Leu Leu Glu Glu
355                 360                 365

GAA TGG AAT TTC ACC AAA GAA ATA ACC CAT TAT ATC CGT GGC GGA GAA      1509
Glu Trp Asn Phe Thr Lys Glu Ile Thr His Tyr Ile Arg Gly Gly Glu
370                 375                 380                 385

GCG CAG GCT GGA AAG CTT TTC TGT GAC ATC GCA GGG ATG CTG CTG AAA      1557
Ala Gln Ala Gly Lys Leu Phe Cys Asp Ile Ala Gly Met Leu Leu Lys
                390                 395                 400

TCC ACA GGG AGC TTT CTG GAA TCC GGC CTG CAG GAG AGC TGT GCT GAG      1605
Ser Thr Gly Ser Phe Leu Glu Ser Gly Leu Gln Glu Ser Cys Ala Glu
            405                 410                 415

CTG TGG ACC AGC GCC GAC GAC AAC GGT GCT GCC GAC GAG CTA AGG AGA      1653
Leu Trp Thr Ser Ala Asp Asp Asn Gly Ala Ala Asp Glu Leu Arg Arg
        420                 425                 430

TCT GTC ATC GAG ATC AGC CGA GCA CTC AAG GAG CTC TTC CAC GAA GCC      1701
Ser Val Ile Glu Ile Ser Arg Ala Leu Lys Glu Leu Phe His Glu Ala
435                 440                 445

AGG GAA AGA GCC TCC AAG GCC CTG GGC TTT GCT AAA ATG CTG AGG AAG      1749
Arg Glu Arg Ala Ser Lys Ala Leu Gly Phe Ala Lys Met Leu Arg Lys
450                 455                 460                 465

GAC CTA GAA ATA GCA GCA GAG TTC GTG CTA TCT GCA TCA GCC CGA GAG      1797
Asp Leu Glu Ile Ala Ala Glu Phe Val Leu Ser Ala Ser Ala Arg Glu
                470                 475                 480

CTC CTG GAC GCT CTG AAA GCA AAG CAG TAT GTT AAG GTA CAG ATT CCC      1845
Leu Leu Asp Ala Leu Lys Ala Lys Gln Tyr Val Lys Val Gln Ile Pro
            485                 490                 495

GGG TTA GAG AAT TTG CAC GTG TTT GTC CCC GAC AGC CTC GCT GAG GAG      1893
Gly Leu Glu Asn Leu His Val Phe Val Pro Asp Ser Leu Ala Glu Glu
        500                 505                 510

AAG AAA ATT ATT TTG CAG CTA CTC AAT GCT GCC ACA GGA AAG GAC TGC      1941
Lys Lys Ile Ile Leu Gln Leu Leu Asn Ala Ala Thr Gly Lys Asp Cys
515                 520                 525

TCA AAG GAT CCA GAC GAC GTC TTC ATG GAT GCC TTC CTG CTC CTG ACC      1989
Ser Lys Asp Pro Asp Asp Val Phe Met Asp Ala Phe Leu Leu Leu Thr
530                 535                 540                 545

AAG CAT GGG GAC CGA GCC CGT GAC TCA GAA GAT GGC TGG GGC ACA TGG      2037
Lys His Gly Asp Arg Ala Arg Asp Ser Glu Asp Gly Trp Gly Thr Trp
                550                 555                 560

GAA GCT CGG GCT GTC AAA ATT GTG CCT CAG GTG GAG ACT GTG GAC ACC      2085
```

-continued

| | | | | | | | | | | | | |
|---|---|---|---|---|---|---|---|---|---|---|---|---|
|Glu|Ala|Arg|Ala|Val|Lys|Ile|Val|Pro|Gln|Val|Glu|Thr|Val|Asp|Thr|
| | | |565| | | |570| | | |575| | | | |

```
CTG AGA AGC ATG CAG GTG GAC AAC CTT CTG CTG GTT GTC ATG GAG TCT     2133
Leu Arg Ser Met Gln Val Asp Asn Leu Leu Leu Val Val Met Glu Ser
        580                 585                 590

GCT CAC CTC GTA CTT CAG AGA AAA GCC TTC CAG CAG TCC ATT GAG GGG     2181
Ala His Leu Val Leu Gln Arg Lys Ala Phe Gln Gln Ser Ile Glu Gly
595                 600                 605

CTG ATG ACT GTA CGC CAT GAG CAG ACA TCT AGC CAG CCC ATC ATC GCC     2229
Leu Met Thr Val Arg His Glu Gln Thr Ser Ser Gln Pro Ile Ile Ala
610                 615                 620                 625

AAA GGT TTG CAG CAG CTC AAG AAC GAT GCA CTT GAG CTA TGC AAC AGA     2277
Lys Gly Leu Gln Gln Leu Lys Asn Asp Ala Leu Glu Leu Cys Asn Arg
            630                 635                 640

ATC AGC GAT GCC ATC GAC CGT GTG GAC CAC ATG TTC ACC CTG GAG TTC     2325
Ile Ser Asp Ala Ile Asp Arg Val Asp His Met Phe Thr Leu Glu Phe
                645                 650                 655

GAT GCT GAG GTC GAG GAG TCT GAG TCG GCC ACG CTG CAG CAG TAC TAC     2373
Asp Ala Glu Val Glu Glu Ser Glu Ser Ala Thr Leu Gln Gln Tyr Tyr
            660                 665                 670

CGA GAA GCC ATG ATT CAG GGC TAC AAC TTT GGG TTT GAG TAT CAT AAA     2421
Arg Glu Ala Met Ile Gln Gly Tyr Asn Phe Gly Phe Glu Tyr His Lys
        675                 680                 685

GAA GTT GTT CGT TTG ATG TCT GGG GAA TTC AGG CAG AAG ATA GGA GAC     2469
Glu Val Val Arg Leu Met Ser Gly Glu Phe Arg Gln Lys Ile Gly Asp
690                 695                 700                 705

AAA TAT ATA AGC TTC GCC CAG AAG TGG ATG AAT TAC GTG CTG ACC AAA     2517
Lys Tyr Ile Ser Phe Ala Gln Lys Trp Met Asn Tyr Val Leu Thr Lys
            710                 715                 720

TGC GAG AGC GGC AGA GGC ACA AGA CCC AGA TGG GCC ACC CAA GGA TTT     2565
Cys Glu Ser Gly Arg Gly Thr Arg Pro Arg Trp Ala Thr Gln Gly Phe
                725                 730                 735

GAT TTC CTA CAA GCC ATT GAA CCT GCC TTT ATT TCA GCT TTA CCA GAA     2613
Asp Phe Leu Gln Ala Ile Glu Pro Ala Phe Ile Ser Ala Leu Pro Glu
            740                 745                 750

GAT GAC TTC TTG AGT TTG CAA GCC CTG ATG AAT GAG TGC ATC GGG CAC     2661
Asp Asp Phe Leu Ser Leu Gln Ala Leu Met Asn Glu Cys Ile Gly His
755                 760                 765

GTC ATA GGA AAG CCA CAC AGC CCT GTC ACA GCT ATC CAT CGG AAC AGC     2709
Val Ile Gly Lys Pro His Ser Pro Val Thr Ala Ile His Arg Asn Ser
770                 775                 780                 785

CCC CGC CCT GTG AAG GTG CCC CGA TGC CAC AGT GAC CCT CCT AAC CCT     2757
Pro Arg Pro Val Lys Val Pro Arg Cys His Ser Asp Pro Pro Asn Pro
                790                 795                 800

CAC CTC ATC ATC CCG ACT CCA GAG GGA TTC AGC ACC CGG AGC GTG CCT     2805
His Leu Ile Ile Pro Thr Pro Glu Gly Phe Ser Thr Arg Ser Val Pro
            805                 810                 815

TCC GAC GCT CGG ACC CAT GGC AAC TCT GTT GCT GCT GCT GCT GCT GTT     2853
Ser Asp Ala Arg Thr His Gly Asn Ser Val Ala Ala Ala Ala Ala Val
                820                 825                 830

CGT GCC GCC GCC ACC ACT GCT GCT GGC CGC CCT GGC CCA GGT GGT GGT     2901
Arg Ala Ala Ala Thr Thr Ala Ala Gly Arg Pro Gly Pro Gly Gly Gly
        835                 840                 845

GAC TCT GTG CCA GCC AAA CCT GTC AAC ACT GCC CCT GAT ACC AGG GGT     2949
Asp Ser Val Pro Ala Lys Pro Val Asn Thr Ala Pro Asp Thr Arg Gly
850                 855                 860                 865

TCC AGT GTC CCT GAA AAC GAC CGC TTG GCC TCC ATA GCT GCA GAA CTG     2997
Ser Ser Val Pro Glu Asn Asp Arg Leu Ala Ser Ile Ala Ala Glu Leu
            870                 875                 880

CAG TTC AGG TCT CTG AGT CGG CAC TCA AGC CCC ACG GAA GAG CGA GAC     3045
```

```
                Gln Phe Arg Ser Leu Ser Arg His Ser Ser Pro Thr Glu Glu Arg Asp
                                885                 890                 895

GAG CCA GCG TAT CCT CGG AGT GAC TCA AGT GGA TCA ACT CGG AGA AGC            3093
Glu Pro Ala Tyr Pro Arg Ser Asp Ser Ser Gly Ser Thr Arg Arg Ser
        900                 905                 910

TGG GAA CTT CGA ACA CTC ATC AGC CAG ACC AAA GAC TCG GCC TCT AAG            3141
Trp Glu Leu Arg Thr Leu Ile Ser Gln Thr Lys Asp Ser Ala Ser Lys
    915                 920                 925

CAG GGG CCC ATA GAA GCT ATC CAG AAG TCA GTC CGA CTG TTT GAA GAG            3189
Gln Gly Pro Ile Glu Ala Ile Gln Lys Ser Val Arg Leu Phe Glu Glu
930                 935                 940                 945

AGG AGG TAT CGA GAG ATG AGG AGA AAG AAT ATC ATC GGC CAA GTG TGC            3237
Arg Arg Tyr Arg Glu Met Arg Arg Lys Asn Ile Ile Gly Gln Val Cys
                950                 955                 960

GAT ACC CCT AAG TCC TAT GAT AAC GTC ATG CAT GTT GGA CTG AGG AAG            3285
Asp Thr Pro Lys Ser Tyr Asp Asn Val Met His Val Gly Leu Arg Lys
            965                 970                 975

GTG ACA TTT AAG TGG CAA AGA GGA AAC AAA ATT GGA GAA GGA CAG TAT            3333
Val Thr Phe Lys Trp Gln Arg Gly Asn Lys Ile Gly Glu Gly Gln Tyr
        980                 985                 990

GGA AAA GTA TAC ACC TGC ATC AGT GTT GAC ACA GGG GAG CTG ATG GCC            3381
Gly Lys Val Tyr Thr Cys Ile Ser Val Asp Thr Gly Glu Leu Met Ala
995                 1000                1005

ATG AAG GAG ATT CGA TTT CAG CCT AAC GAC CAC AAG ACT ATC AAG GAG            3429
Met Lys Glu Ile Arg Phe Gln Pro Asn Asp His Lys Thr Ile Lys Glu
1010                1015                1020                1025

ACT GCA GAC GAG TTG AAA ATA TTT GAA GGC ATC AAG CAC CCC AAC CTG            3477
Thr Ala Asp Glu Leu Lys Ile Phe Glu Gly Ile Lys His Pro Asn Leu
                1030                1035                1040

GTC CGG TAT TTT GGC GTG GAG CTT CAC AGG GAA GAG ATG TAC ATC TTC            3525
Val Arg Tyr Phe Gly Val Glu Leu His Arg Glu Glu Met Tyr Ile Phe
            1045                1050                1055

ATG GAG TAC TGT GAT GAG GGT ACA CTA GAG GAG GTG TCA CGA CTG GGC            3573
Met Glu Tyr Cys Asp Glu Gly Thr Leu Glu Glu Val Ser Arg Leu Gly
        1060                1065                1070

CTG CAG GAG CAC GTC ATC AGG TTA TAT ACC AAG CAG ATC ACT GTC GCC            3621
Leu Gln Glu His Val Ile Arg Leu Tyr Thr Lys Gln Ile Thr Val Ala
1075                1080                1085

ATC AAC GTC CTC CAT GAG CAC GGC ATC GTT CAC CGA GAC ATC AAA GGT            3669
Ile Asn Val Leu His Glu His Gly Ile Val His Arg Asp Ile Lys Gly
1090                1095                1100                1105

GCC AAT ATC TTC CTT ACG TCA TCT GGA CTA ATC AAG CTG GGA GAT TTT            3717
Ala Asn Ile Phe Leu Thr Ser Ser Gly Leu Ile Lys Leu Gly Asp Phe
                1110                1115                1120

GGA TGC TCT GTA AAA CTT AAA AAC AAC GCC CAG ACC ATG CCC GGA GAG            3765
Gly Cys Ser Val Lys Leu Lys Asn Asn Ala Gln Thr Met Pro Gly Glu
            1125                1130                1135

GTG AAC AGC ACC CTA GGG ACA GCA GCT TAC ATG GCC CCT GAA GTT ATT            3813
Val Asn Ser Thr Leu Gly Thr Ala Ala Tyr Met Ala Pro Glu Val Ile
        1140                1145                1150

ACC CGA GCC AAA GGA GAA GGC CAC GGA CGT GCG GCA GAT ATC TGG AGT            3861
Thr Arg Ala Lys Gly Glu Gly His Gly Arg Ala Ala Asp Ile Trp Ser
    1155                1160                1165

CTG GGG TGC GTC GTC ATA GAG ATG GTG ACT GGC AAG CGG CCT TGG CAT            3909
Leu Gly Cys Val Val Ile Glu Met Val Thr Gly Lys Arg Pro Trp His
1170                1175                1180                1185

GAG TAT GAA CAC AAC TTT CAG ATT ATG TAC AAG GTG GGG ATG GGA CAC            3957
Glu Tyr Glu His Asn Phe Gln Ile Met Tyr Lys Val Gly Met Gly His
                1190                1195                1200

AAG CCA CCA ATC CCG GAA AGG CTA AGC CCT GAA GGA AAG GCC TTT CTC            4005
```

```
Lys Pro Pro Ile Pro Glu Arg Leu Ser Pro Glu Gly Lys Ala Phe Leu
            1205                1210                1215

TCG CAC TGC CTG GAA AGT GAC CCG AAG ATA CGG TGG ACA GCC AGC CAG    4053
Ser His Cys Leu Glu Ser Asp Pro Lys Ile Arg Trp Thr Ala Ser Gln
            1220                1225                1230

CTC CTC GAC CAC GCT TTT GTC AAG GTT TGC ACA GAT GAA GAG            4095
Leu Leu Asp His Ala Phe Val Lys Val Cys Thr Asp Glu Glu
            1235                1240            1245

TGAAGTGAAC CAGTCCGTGG CCTAGTAGTG TGTGGACAGA ATCCCGTGAT CACTACTGTA    4155

TGTAATATTT ACATAAAGAC TGCAGCGCAG GCGGCCTTCC TAACCTCCCA GGACTGAAGA    4215

CTACAGGGGT GACAAGCCTC ACTTCTGCTG CTCCTGTCGC CTGCTGAGTG ACAGTGCTGA    4275

GGTTAAAGGA GCCGCACGTT AAGTGCCATT ACTACTGTAC ACGGCCACCG CCTCTGTCCC    4335

CTCCGACCCT CTCGTGACTG AGAACCAACC GTGTCATCAG CACAGTGTTT TTGAGCTCCT    4395

GGGGTTCAGA AGAACATGTA GTGTTCCCGG GTGTCCGGGA CGTTTATTTC AACCTCCTGG    4455

TCGTTGGCTC TGACTGTGGA GCCTCCTTGT TCGAAAGCTG CAGGTTTGTT ATGCAAAGGC    4515

TCGTAAGTGA AGCTGAAGAA AAGGTTCTTT TTCAATAAAT GGTTTATTTT AGGAAAGCGA    4575

AAAAAAAAAA AAAAAA                                                   4592

(2) INFORMATION FOR SEQ ID NO:10:

(i) SEQUENCE CHARACTERISTICS:
        (A) LENGTH: 1247 amino acids
        (B) TYPE: amino acid
        (D) TOPOLOGY: linear (ii) MOLECULE TYPE: protein (xi) SEQUENCE DESCRIPTION: SEQ ID NO:10:

Met Glu Leu Leu Glu Tyr Met Glu Ala Leu Tyr Pro Ser Leu Gln Ala
  1               5                  10                  15

Leu Gln Lys Asp Tyr Glu Arg Tyr Ala Ala Lys Asp Phe Glu Asp Arg
             20                  25                  30

Val Gln Ala Leu Cys Leu Trp Leu Asn Ile Thr Lys Asp Leu Asn Gln
         35                  40                  45

Lys Leu Arg Ile Met Gly Thr Val Leu Gly Ile Lys Phe Leu Ser Asp
     50                  55                  60

Ile Gly Trp Pro Val Lys Glu Ile Pro Ser Arg Pro Ser Lys Gly
 65                  70                  75                  80

Tyr Glu Pro Glu Asp Glu Val Glu Asp Thr Val Glu Leu Arg Glu
                 85                  90                  95

Leu Glu Ser Gly Thr Glu Glu Ser Asp Glu Glu Pro Thr Pro Ser Pro
            100                 105                 110

Arg Val Pro Glu Leu Arg Leu Ser Thr Asp Thr Ile Leu Asp Ser Arg
        115                 120                 125

Ser Gln Gly Cys Val Ser Arg Lys Leu Glu Arg Leu Glu Ser Glu Glu
    130                 135                 140

Asp Ser Ile Gly Trp Gly Thr Ala Asp Cys Gly Pro Glu Ala Ser Arg
145                 150                 155                 160

His Cys Leu Thr Ser Met Tyr Arg Pro Phe Val Asp Lys Ala Leu Lys
                165                 170                 175

Gln Met Gly Leu Arg Lys Leu Ile Leu Arg Leu His Lys Leu Met Asn
            180                 185                 190

Gly Ser Leu Gln Arg Ala Arg Val Ala Leu Val Lys Asp Asp Arg Pro
        195                 200                 205
```

```
Val Glu Phe Ser Asp Phe Pro Gly Pro Met Trp Gly Ser Asp Tyr Val
210                 215                 220

Gln Leu Ser Gly Thr Pro Pro Ser Ser Glu Gln Lys Cys Ser Ala Val
225                 230                 235                 240

Ser Trp Glu Glu Leu Arg Ala Met Asp Leu Pro Ser Phe Glu Pro Ala
            245                 250                 255

Phe Leu Val Leu Cys Arg Val Leu Leu Asn Val Ile His Glu Cys Leu
            260                 265                 270

Lys Leu Arg Leu Glu Gln Arg Pro Ala Gly Glu Pro Ser Leu Leu Ser
            275                 280                 285

Ile Lys Gln Leu Val Arg Glu Cys Lys Glu Val Leu Lys Gly Gly Leu
290                 295                 300

Leu Met Lys Gln Tyr Tyr Gln Phe Met Leu Gln Glu Val Leu Gly Gly
305                 310                 315                 320

Leu Glu Lys Thr Asp Cys Asn Met Asp Ala Phe Glu Glu Asp Leu Gln
            325                 330                 335

Lys Met Leu Met Val Tyr Phe Asp Tyr Met Arg Ser Trp Ile Gln Met
            340                 345                 350

Leu Gln Gln Leu Pro Gln Ala Ser His Ser Leu Lys Asn Leu Leu Glu
            355                 360                 365

Glu Glu Trp Asn Phe Thr Lys Glu Ile Thr His Tyr Ile Arg Gly Gly
370                 375                 380

Glu Ala Gln Ala Gly Lys Leu Phe Cys Asp Ile Ala Gly Met Leu Leu
385                 390                 395                 400

Lys Ser Thr Gly Ser Phe Leu Glu Ser Gly Leu Gln Glu Ser Cys Ala
            405                 410                 415

Glu Leu Trp Thr Ser Ala Asp Asp Asn Gly Ala Ala Asp Glu Leu Arg
            420                 425                 430

Arg Ser Val Ile Glu Ile Ser Arg Ala Leu Lys Glu Leu Phe His Glu
            435                 440                 445

Ala Arg Glu Arg Ala Ser Lys Ala Leu Gly Phe Ala Lys Met Leu Arg
450                 455                 460

Lys Asp Leu Glu Ile Ala Ala Glu Phe Val Leu Ser Ala Ser Ala Arg
465                 470                 475                 480

Glu Leu Leu Asp Ala Leu Lys Ala Lys Gln Tyr Val Lys Val Gln Ile
            485                 490                 495

Pro Gly Leu Glu Asn Leu His Val Phe Val Pro Asp Ser Leu Ala Glu
            500                 505                 510

Glu Lys Lys Ile Ile Leu Gln Leu Leu Asn Ala Ala Thr Gly Lys Asp
            515                 520                 525

Cys Ser Lys Asp Pro Asp Val Phe Met Asp Ala Phe Leu Leu Leu
530                 535                 540

Thr Lys His Gly Asp Arg Ala Arg Asp Ser Glu Asp Gly Trp Gly Thr
545                 550                 555                 560

Trp Glu Ala Arg Ala Val Lys Ile Val Pro Gln Val Glu Thr Val Asp
            565                 570                 575

Thr Leu Arg Ser Met Gln Val Asp Asn Leu Leu Leu Val Val Met Glu
            580                 585                 590

Ser Ala His Leu Val Leu Gln Arg Lys Ala Phe Gln Gln Ser Ile Glu
            595                 600                 605

Gly Leu Met Thr Val Arg His Glu Gln Thr Ser Ser Gln Pro Ile Ile
610                 615                 620

Ala Lys Gly Leu Gln Gln Leu Lys Asn Asp Ala Leu Glu Leu Cys Asn
625                 630                 635                 640
```

```
Arg Ile Ser Asp Ala Ile Asp Arg Val Asp His Met Phe Thr Leu Glu
            645                 650                 655

Phe Asp Ala Glu Val Glu Glu Ser Ser Ala Thr Leu Gln Gln Tyr
            660                 665                 670

Tyr Arg Glu Ala Met Ile Gln Gly Tyr Asn Phe Gly Phe Glu Tyr His
            675                 680                 685

Lys Glu Val Val Arg Leu Met Ser Gly Glu Phe Arg Gln Lys Ile Gly
            690                 695                 700

Asp Lys Tyr Ile Ser Phe Ala Gln Lys Trp Met Asn Tyr Val Leu Thr
705                 710                 715                 720

Lys Cys Glu Ser Gly Arg Gly Thr Arg Pro Arg Trp Ala Thr Gln Gly
            725                 730                 735

Phe Asp Phe Leu Gln Ala Ile Glu Pro Ala Phe Ile Ser Ala Leu Pro
            740                 745                 750

Glu Asp Asp Phe Leu Ser Leu Gln Ala Leu Met Asn Glu Cys Ile Gly
            755                 760                 765

His Val Ile Gly Lys Pro His Ser Pro Val Thr Ala Ile His Arg Asn
            770                 775                 780

Ser Pro Arg Pro Val Lys Val Pro Arg Cys His Ser Asp Pro Pro Asn
785                 790                 795                 800

Pro His Leu Ile Ile Pro Thr Pro Glu Gly Phe Ser Thr Arg Ser Val
            805                 810                 815

Pro Ser Asp Ala Arg Thr His Gly Asn Ser Val Ala Ala Ala Ala
            820                 825                 830

Val Arg Ala Ala Ala Thr Thr Ala Ala Gly Arg Pro Gly Pro Gly Gly
            835                 840                 845

Gly Asp Ser Val Pro Ala Lys Pro Val Asn Thr Ala Pro Asp Thr Arg
850                 855                 860

Gly Ser Ser Val Pro Glu Asn Asp Arg Leu Ala Ser Ile Ala Ala Glu
865                 870                 875                 880

Leu Gln Phe Arg Ser Leu Ser Arg His Ser Ser Pro Thr Glu Glu Arg
            885                 890                 895

Asp Glu Pro Ala Tyr Pro Arg Ser Asp Ser Ser Gly Ser Thr Arg Arg
            900                 905                 910

Ser Trp Glu Leu Arg Thr Leu Ile Ser Gln Thr Lys Asp Ser Ala Ser
            915                 920                 925

Lys Gln Gly Pro Ile Glu Ala Ile Gln Lys Ser Val Arg Leu Phe Glu
            930                 935                 940

Glu Arg Arg Tyr Arg Glu Met Arg Arg Lys Asn Ile Ile Gly Gln Val
945                 950                 955                 960

Cys Asp Thr Pro Lys Ser Tyr Asp Asn Val Met His Val Gly Leu Arg
            965                 970                 975

Lys Val Thr Phe Lys Trp Gln Arg Gly Asn Lys Ile Gly Glu Gly Gln
            980                 985                 990

Tyr Gly Lys Val Tyr Thr Cys Ile Ser Val Asp Thr Gly Glu Leu Met
            995                 1000                1005

Ala Met Lys Glu Ile Arg Phe Gln Pro Asn Asp His Lys Thr Ile Lys
            1010                1015                1020

Glu Thr Ala Asp Glu Leu Lys Ile Phe Glu Gly Ile Lys His Pro Asn
1025                1030                1035                1040

Leu Val Arg Tyr Phe Gly Val Glu Leu His Arg Glu Glu Met Tyr Ile
            1045                1050                1055

Phe Met Glu Tyr Cys Asp Glu Gly Thr Leu Glu Glu Val Ser Arg Leu
```

-continued

```
                    1060                1065                1070
Gly Leu Gln Glu His Val Ile Arg Leu Tyr Thr Lys Gln Ile Thr Val
                1075                1080                1085

Ala Ile Asn Val Leu His Glu His Gly Ile Val His Arg Asp Ile Lys
            1090                1095                1100

Gly Ala Asn Ile Phe Leu Thr Ser Ser Gly Leu Ile Lys Leu Gly Asp
1105                1110                1115                1120

Phe Gly Cys Ser Val Lys Leu Lys Asn Asn Ala Gln Thr Met Pro Gly
                1125                1130                1135

Glu Val Asn Ser Thr Leu Gly Thr Ala Ala Tyr Met Ala Pro Glu Val
            1140                1145                1150

Ile Thr Arg Ala Lys Gly Glu Gly His Gly Arg Ala Ala Asp Ile Trp
        1155                1160                1165

Ser Leu Gly Cys Val Val Ile Glu Met Val Thr Gly Lys Arg Pro Trp
    1170                1175                1180

His Glu Tyr Glu His Asn Phe Gln Ile Met Tyr Lys Val Gly Met Gly
1185                1190                1195                1200

His Lys Pro Pro Ile Pro Glu Arg Leu Ser Pro Glu Gly Lys Ala Phe
                1205                1210                1215

Leu Ser His Cys Leu Glu Ser Asp Pro Lys Ile Arg Trp Thr Ala Ser
            1220                1225                1230

Gln Leu Leu Asp His Ala Phe Val Lys Val Cys Thr Asp Glu Glu
        1235                1240                1245
```

(2) INFORMATION FOR SEQ ID NO:11:

(i) SEQUENCE CHARACTERISTICS:
        (A) LENGTH: 2503 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 466..2325

(xi) SEQUENCE DESCRIPTION: SEQ ID NO:11:

```
GGTGGCGGCC GCTCTAGAAC TAGTGGATCC CCCGGGCTGC AGGAATTCGG CACGAGGGAC    60

GATCCAGCGG CAGAGTCGCC GCTTCCGCTT CGCTGCTTCT CCGGTCGGCG ACGCGGGCCC   120

GGGGCTTCCT TTTCATCGGC CCAGCTTATT CCGCGGGCCC CGGGGCTGCA GCTACCCAGA   180

AGCGGCGAAG AGGCCCTGGG CTGCGCGCCC GCTGTCCCAT GTGAAGCAGG TTGGGCCTGG   240

TCCCCGGCCC GTGCCCGGTT GTCTGCGGCC CTTCAGGCCT CAGGGACCCC CGCGAGGCGC   300

TGCTCCTGGG GGGCGCGGTG ACAGGCCGTG CGGGGGCGGA GGGGCCAGCT CGGTGGCCTC   360

CTCTCGGCCC TCGCGTCCGC GATCCCGCCC AGCGGCCGGG CAATAAAGAA TGTTGATGGG   420

AGAACCATTT TCCTAATTTT CAAATTATTG AGCTGGTCGC GCATA ATG GAT GAT        474
                                                 Met Asp Asp
                                                   1

CAG CAA GCT TTG AAT TCA ATC ATG CAA GAT TTG GCT GTC CTT CAT AAG      522
Gln Gln Ala Leu Asn Ser Ile Met Gln Asp Leu Ala Val Leu His Lys
   5                  10                  15

GCC AGT CGG CCA GCA TTA TCT TTA CAA GAA ACC AGG AAA GCA AAA CCT      570
Ala Ser Arg Pro Ala Leu Ser Leu Gln Glu Thr Arg Lys Ala Lys Pro
 20                  25                  30                  35

TCA TCA CCA AAA AAA CAG AAT GAT GTT CGA GTC AAA TTT GAA CAT AGA      618
Ser Ser Pro Lys Lys Gln Asn Asp Val Arg Val Lys Phe Glu His Arg
```

-continued

```
                         40                   45                       50
GGA GAA AAA AGG ATC CTG CAG GTT ACT AGA CCA GTT AAA CTA GAA GAC                666
Gly Glu Lys Arg Ile Leu Gln Val Thr Arg Pro Val Lys Leu Glu Asp
                 55                   60                   65

CTG AGA TCT AAG TCT AAG ATC GCC TTT GGG CAG TCT ATG GAT CTA CAC                714
Leu Arg Ser Lys Ser Lys Ile Ala Phe Gly Gln Ser Met Asp Leu His
             70                   75                   80

TAT ACC AAC AAT GAG TTG GTA ATT CCG TTA ACT ACC CAA GAT GAC TTG                762
Tyr Thr Asn Asn Glu Leu Val Ile Pro Leu Thr Thr Gln Asp Asp Leu
         85                   90                   95

GAC AAA GCT GTG GAA CTG CTG GAT CGC AGT ATT CAC ATG AAG AGT CTC                810
Asp Lys Ala Val Glu Leu Leu Asp Arg Ser Ile His Met Lys Ser Leu
100                 105                  110                  115

AAG ATA TTA CTT GTA GTA AAT GGG AGT ACA CAG GCT ACT AAT TTA GAA                858
Lys Ile Leu Leu Val Val Asn Gly Ser Thr Gln Ala Thr Asn Leu Glu
                120                  125                  130

CCA TCA CCG TCA CCA GAA GAT TTG AAT AAT ACA CCA CTT GGT GCA GAG                906
Pro Ser Pro Ser Pro Glu Asp Leu Asn Asn Thr Pro Leu Gly Ala Glu
            135                  140                  145

AGG AAA AAG CGG CTA TCT GTA GTA GGT CCC CCT AAT AGG GAT AGA AGT                954
Arg Lys Lys Arg Leu Ser Val Val Gly Pro Pro Asn Arg Asp Arg Ser
        150                  155                  160

TCC CCT CCT CCA GGA TAC ATT CCA GAC ATA CTA CAC CAG ATT GCC CGG               1002
Ser Pro Pro Pro Gly Tyr Ile Pro Asp Ile Leu His Gln Ile Ala Arg
165                  170                  175

AAT GGG TCA TTC ACT AGC ATC AAC AGT GAA GGA GAG TTC ATT CCA GAG               1050
Asn Gly Ser Phe Thr Ser Ile Asn Ser Glu Gly Glu Phe Ile Pro Glu
180                  185                  190                  195

AGC ATG GAC CAA ATG CTG GAT CCA TTG TCT TTA AGC AGC CCT GAA AAT               1098
Ser Met Asp Gln Met Leu Asp Pro Leu Ser Leu Ser Ser Pro Glu Asn
                200                  205                  210

TCT GGC TCA GGA AGC TGT CCG TCA CTT GAT AGT CCT TTG GAT GGA GAA               1146
Ser Gly Ser Gly Ser Cys Pro Ser Leu Asp Ser Pro Leu Asp Gly Glu
            215                  220                  225

AGC TAC CCA AAA TCA CGG ATG CCT AGG GCA CAG AGC TAC CCA GAT AAT               1194
Ser Tyr Pro Lys Ser Arg Met Pro Arg Ala Gln Ser Tyr Pro Asp Asn
        230                  235                  240

CAT CAG GAG TTT ACA GAC TAT GAT AAC CCC ATT TTT GAG AAA TTT GGA               1242
His Gln Glu Phe Thr Asp Tyr Asp Asn Pro Ile Phe Glu Lys Phe Gly
245                  250                  255

AAA GGA GGA ACA TAT CCA AGA AGG TAC CAC GTT TCC TAT CAT CAC CAG               1290
Lys Gly Gly Thr Tyr Pro Arg Arg Tyr His Val Ser Tyr His His Gln
260                  265                  270                  275

GAG TAT AAT GAC GGT CGG AAG ACT TTT CCA AGA GCT AGA AGG ACC CAG               1338
Glu Tyr Asn Asp Gly Arg Lys Thr Phe Pro Arg Ala Arg Arg Thr Gln
                280                  285                  290

GGC ACC AGT TTC CGG TCT CCT GTG AGC TTC AGT CCT ACT GAT CAC TCC               1386
Gly Thr Ser Phe Arg Ser Pro Val Ser Phe Ser Pro Thr Asp His Ser
            295                  300                  305

TTA AGC ACT AGT AGT GGA AGC AGT GTC TTT ACC CCA GAG TAT GAC GAC               1434
Leu Ser Thr Ser Ser Gly Ser Ser Val Phe Thr Pro Glu Tyr Asp Asp
        310                  315                  320

AGT CGA ATA AGA AGA CGG GGG AGT GAC ATA GAC AAT CCT ACT TTG ACT               1482
Ser Arg Ile Arg Arg Arg Gly Ser Asp Ile Asp Asn Pro Thr Leu Thr
325                  330                  335

GTC ACA GAC ATC AGC CCA CCC AGC CGT TCA CCT CGA GCT CCG ACC AAC               1530
Val Thr Asp Ile Ser Pro Pro Ser Arg Ser Pro Arg Ala Pro Thr Asn
340                  345                  350                  355

TGG AGA CTG GGC AAG CTG CTT GGC CAA GGA GCT TTT GGT AGG GTC TAC               1578
Trp Arg Leu Gly Lys Leu Leu Gly Gln Gly Ala Phe Gly Arg Val Tyr
```

-continued

```
                     360                 365                 370
CTC TGC TAT GAT GTT GAT ACC GGA AGA GAG CTG GCT GTT AAG CAA GTT    1626
Leu Cys Tyr Asp Val Asp Thr Gly Arg Glu Leu Ala Val Lys Gln Val
            375                 380                 385

CAG TTT AAC CCT GAG AGC CCA GAG ACC AGC AAG GAA GTA AAT GCA CTT    1674
Gln Phe Asn Pro Glu Ser Pro Glu Thr Ser Lys Glu Val Asn Ala Leu
            390                 395                 400

GAG TGT GAA ATT CAG TTG TTG AAA AAC TTG TTG CAT GAG CGA ATT GTT    1722
Glu Cys Glu Ile Gln Leu Leu Lys Asn Leu Leu His Glu Arg Ile Val
            405                 410                 415

CAG TAT TAT GGC TGT TTG AGG GAT CCT CAG GAG AAA ACA CTT TCC ATC    1770
Gln Tyr Tyr Gly Cys Leu Arg Asp Pro Gln Glu Lys Thr Leu Ser Ile
420                 425                 430                 435

TTT ATG GAG TAT ATG CCA GGG GGT TCA ATT AAG GAC CAA CTA AAA GCC    1818
Phe Met Glu Tyr Met Pro Gly Gly Ser Ile Lys Asp Gln Leu Lys Ala
                440                 445                 450

TAC GGA GCT CTT ACT GAG AAC GTG ACG AGG AAG TAC ACC CGT CAG ATT    1866
Tyr Gly Ala Leu Thr Glu Asn Val Thr Arg Lys Tyr Thr Arg Gln Ile
                455                 460                 465

CTG GAG GGG GTC CAT TAT TTG CAT AGT AAT ATG ATT GTC CAT AGA GAT    1914
Leu Glu Gly Val His Tyr Leu His Ser Asn Met Ile Val His Arg Asp
            470                 475                 480

ATC AAA GGA GCA AAT ATC TTA AGG GAT TCC ACA GGC AAT ATC AAG TTA    1962
Ile Lys Gly Ala Asn Ile Leu Arg Asp Ser Thr Gly Asn Ile Lys Leu
485                 490                 495

GGA GAC TTT GGG GCT AGT AAA CGG CTT CAG ACC ATC TGT CTC TCA GGC    2010
Gly Asp Phe Gly Ala Ser Lys Arg Leu Gln Thr Ile Cys Leu Ser Gly
500                 505                 510                 515

ACA GGA ATG AAG TCT GTC ACA GGC ACG CCA TAC TGG ATG AGT CCT GAG    2058
Thr Gly Met Lys Ser Val Thr Gly Thr Pro Tyr Trp Met Ser Pro Glu
                520                 525                 530

GTC ATC AGT GGA GAA GGC TAT GGA AGA AAA GCA GAC ATC TGG AGT GTA    2106
Val Ile Ser Gly Glu Gly Tyr Gly Arg Lys Ala Asp Ile Trp Ser Val
                535                 540                 545

GCA TGT ACT GTG GTA GAA ATG CTA ACT GAA AAG CCA CCT TGG GCT GAA    2154
Ala Cys Thr Val Val Glu Met Leu Thr Glu Lys Pro Pro Trp Ala Glu
            550                 555                 560

TTT GAA GCA ATG GCT GCC ATC TTT AAG ATC GCC ACT CAG CCA ACG AAC    2202
Phe Glu Ala Met Ala Ala Ile Phe Lys Ile Ala Thr Gln Pro Thr Asn
565                 570                 575

CCA AAG CTG CCA CCT CAT GTC TCA GAC TAT ACT CGG GAC TTC CTC AAA    2250
Pro Lys Leu Pro Pro His Val Ser Asp Tyr Thr Arg Asp Phe Leu Lys
580                 585                 590                 595

CGG ATT TTT GTA GAG GCC AAA CTT CGA CCT TCA GCG GAG GAG CTC TTG    2298
Arg Ile Phe Val Glu Ala Lys Leu Arg Pro Ser Ala Glu Glu Leu Leu
                600                 605                 610

CGG CAC ATG TTT GTG CAT TAT CAC TAGCAGCGGC GGCTTCGGTC CTCCACCAGC   2352
Arg His Met Phe Val His Tyr His
                615                 620

TCCATCCTCG CGGCCACCTT CTCTCTTACT GCACTTTCCT TTTTTATAAA AAAGAGAGAT   2412

GGGGAGAAAA AGACAAGAGG GAAAATATTT CTCTTGATTC TTGGTTAAAT TTGTTTAATA   2472

ATAATAGTAA ACTAAAAAAA AAAAAAAAAA A                                 2503
```

(2) INFORMATION FOR SEQ ID NO:12:

(i) SEQUENCE CHARACTERISTICS:
        (A) LENGTH: 619 amino acids
        (B) TYPE: amino acid
        (D) TOPOLOGY: linear (ii) MOLECULE TYPE: protein (xi) SEQUENCE DESCRIPTION: SEQ ID NO:12:

Met Asp Asp Gln Gln Ala Leu Asn Ser Ile Met Gln Asp Leu Ala Val
 1               5                  10                  15

Leu His Lys Ala Ser Arg Pro Ala Leu Ser Leu Gln Glu Thr Arg Lys
                20                  25                  30

Ala Lys Pro Ser Ser Pro Lys Lys Gln Asn Asp Val Arg Val Lys Phe
            35                  40                  45

Glu His Arg Gly Glu Lys Arg Ile Leu Gln Val Thr Arg Pro Val Lys
        50                  55                  60

Leu Glu Asp Leu Arg Ser Lys Ser Lys Ile Ala Phe Gly Gln Ser Met
65                  70                  75                  80

Asp Leu His Tyr Thr Asn Asn Glu Leu Val Ile Pro Leu Thr Thr Gln
                85                  90                  95

Asp Asp Leu Asp Lys Ala Val Glu Leu Leu Asp Arg Ser Ile His Met
            100                 105                 110

Lys Ser Leu Lys Ile Leu Leu Val Val Asn Gly Ser Thr Gln Ala Thr
        115                 120                 125

Asn Leu Glu Pro Ser Pro Ser Pro Glu Asp Leu Asn Asn Thr Pro Leu
130                 135                 140

Gly Ala Glu Arg Lys Lys Arg Leu Ser Val Val Gly Pro Pro Asn Arg
145                 150                 155                 160

Asp Arg Ser Ser Pro Pro Pro Gly Tyr Ile Pro Asp Ile Leu His Gln
                165                 170                 175

Ile Ala Arg Asn Gly Ser Phe Thr Ser Ile Asn Ser Glu Gly Glu Phe
            180                 185                 190

Ile Pro Glu Ser Met Asp Gln Met Leu Asp Pro Leu Ser Leu Ser Ser
        195                 200                 205

Pro Glu Asn Ser Gly Ser Gly Ser Cys Pro Ser Leu Asp Ser Pro Leu
210                 215                 220

Asp Gly Glu Ser Tyr Pro Lys Ser Arg Met Pro Arg Ala Gln Ser Tyr
225                 230                 235                 240

Pro Asp Asn His Gln Glu Phe Thr Asp Tyr Asp Asn Pro Ile Phe Glu
                245                 250                 255

Lys Phe Gly Lys Gly Gly Thr Tyr Pro Arg Arg Tyr His Val Ser Tyr
            260                 265                 270

His His Gln Glu Tyr Asn Asp Gly Arg Lys Thr Phe Pro Arg Ala Arg
        275                 280                 285

Arg Thr Gln Gly Thr Ser Phe Arg Ser Pro Val Ser Phe Ser Pro Thr
290                 295                 300

Asp His Ser Leu Ser Thr Ser Ser Gly Ser Ser Val Phe Thr Pro Glu
305                 310                 315                 320

Tyr Asp Asp Ser Arg Ile Arg Arg Gly Ser Asp Ile Asp Asn Pro
                325                 330                 335

Thr Leu Thr Val Thr Asp Ile Ser Pro Pro Ser Arg Ser Pro Arg Ala
            340                 345                 350

Pro Thr Asn Trp Arg Leu Gly Lys Leu Leu Gly Gln Gly Ala Phe Gly
        355                 360                 365

Arg Val Tyr Leu Cys Tyr Asp Val Asp Thr Gly Arg Glu Leu Ala Val
370                 375                 380

Lys Gln Val Gln Phe Asn Pro Gly Ser Pro Glu Thr Ser Lys Glu Val
385                 390                 395                 400

Asn Ala Leu Glu Cys Glu Ile Gln Leu Leu Lys Asn Leu Leu His Glu

```
                    405                 410                 415
Arg Ile Val Gln Tyr Tyr Gly Cys Leu Arg Asp Pro Gln Glu Lys Thr
                420                 425                 430

Leu Ser Ile Phe Met Glu Tyr Met Pro Gly Gly Ser Ile Lys Asp Gln
                435                 440                 445

Leu Lys Ala Tyr Gly Ala Leu Thr Glu Asn Val Thr Arg Lys Tyr Thr
                450                 455                 460

Arg Gln Ile Leu Glu Gly Val His Tyr Leu His Ser Asn Met Ile Val
465                 470                 475                 480

His Arg Asp Ile Lys Gly Ala Asn Ile Leu Arg Asp Ser Thr Gly Asn
                485                 490                 495

Ile Lys Leu Gly Asp Phe Gly Ala Ser Lys Arg Leu Gln Thr Ile Cys
                500                 505                 510

Leu Ser Gly Thr Gly Met Lys Ser Val Thr Gly Thr Pro Tyr Trp Met
                515                 520                 525

Ser Pro Glu Val Ile Ser Gly Glu Gly Tyr Gly Arg Lys Ala Asp Ile
                530                 535                 540

Trp Ser Val Ala Cys Thr Val Val Glu Met Leu Thr Glu Lys Pro Pro
545                 550                 555                 560

Trp Ala Glu Phe Glu Ala Met Ala Ala Ile Phe Lys Ile Ala Thr Gln
                565                 570                 575

Pro Thr Asn Pro Lys Leu Pro Pro His Val Ser Asp Tyr Thr Arg Asp
                580                 585                 590

Phe Leu Lys Arg Ile Phe Val Glu Ala Lys Leu Arg Pro Ser Ala Glu
                595                 600                 605

Glu Leu Leu Arg His Met Phe Val His Tyr His
610                 615
```

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:13:

```
Asp Arg Pro Pro Ser Arg Glu Leu Leu Lys His Pro Val Glu Arg
1               5                   10                  15
```

(2) INFORMATION FOR SEQ ID NO:14:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:14:

```
Thr Thr Tyr Ala Asp Phe Ile Ala Ser Gly Arg Thr Gly Arg Arg Asn
1               5                   10                  15

Ala Ile His Asp
                20
```

METHODS FOR REGULATING MEKK PROTEIN ACTIVITY

CROSS-REFERENCE TO RELATED APPLICATIONS

The present application is a continuation application of U.S. patent application Ser. No. 08/440,421, filed May 12, 1995, now abandoned entitled "METHOD AND PRODUCT FOR REGULATING CELL RESPONSIVENESS TO EXTERNAL SIGNALS", which is a continuation-in-part of U.S. patent application Ser. No. 08/345,516 entitled "Method and Product for Regulating Cell Responsiveness to External Signals", filed Nov. 28, 1994, now abandoned, which is a divisional application of U.S. Pat. No. 5,405,941 entitled "MEKK Protein, Capable of Phosphorylating MEK", filed Apr. 15, 1993 as application Ser. No. 08/049,254 and issued Apr. 11, 1995. The present application is also a continuation-in-part of U.S. patent application Ser. No. 08/323,460 entitled "Method and Product for Regulating Cell Responsiveness to External Signals", filed Oct. 14, 1994 and issued as U.S. Pat. No. 5,854,043; PCT Application No. PCT/US94/11690 entitled "Method and Product for Regulating Cell Responsiveness to External Signals", filed Oct. 14, 1994; and PCT Application No. PCT/US94/04178 for "Method and Product for Regulating Cell Responsiveness to External Signals", filed Apr. 15, 1994, all of which are continuation-in-part applications of U.S. Pat. No. 5,405,941. The above-referenced patents and patent applications are incorporated herein by this reference in their entirety.

This invention was made in part with government support under USPHS Grant DK37871 and USPHS Grant GM30324, both awarded by the National Institutes of Health. The government has certain rights to this invention.

FIELD OF THE INVENTION

This invention relates to isolated nucleic acid molecules encoding MEKK proteins, substantially pure MEKK proteins, and products and methods for regulating signal transduction in a cell.

SUMMARY OF THE INVENTION

The present invention relates to a substantially pure MEKK protein capable of phosphorylating mammalian MEK protein, in which the MEKK protein comprises a catalytic domain. The present invention includes a substantially pure MEKK protein capable of regulating signals initiated from a growth factor receptor on the surface of a cell by regulating the activity of MAPK protein, the ability to regulate being divergent from Raf protein signal regulation. In particular, the substantially pure MEKK protein comprises at least a portion of an amino acid sequence encoded by a nucleic acid sequence that is capable of hybridizing under stringent conditions with a nucleic acid molecule encoding the amino acid sequence shown in SEQ ID NO:1 and SEQ ID NO:2. The nucleic acid and protein sequences disclosed in related U.S. and PCT patent applications are incorporated herein by this reference in their entirety, namely U.S. patent application Ser. No. 08/345,516 entitled "Method and Product for Regulating Cell Responsiveness to External Signals", filed Dec. 13, 1994; U.S. Pat. No. 5,405,941 entitled "MEKK Protein, Capable of Phosphorylating MEK", issued Apr. 11, 1995; U.S. patent application Ser. No. 08/323,460 entitled "Method and Product for Regulating Cell Responsiveness to External Signals", filed Oct. 14, 1994; PCT Application No. PCT/US94/11690 entitled "Method and Product for Regulating Cell Responsiveness to External Signals", filed Oct. 14, 1994; and PCT Application No. PCT/US94/04178 for "Method and Product for Regulating Cell Responsiveness to External Signals", filed Apr. 15, 1994. U.S. patent application Ser. No. 08/323,460, filed Oct. 14, 1994 discloses nucleic acid and protein sequences for MEKK1, MEKK2, MEKK3, MEKK4 and MEKK5. In the application, MEKK 1 nucleic acid and protein sequences are represented by SEQ ID NO:1 and SEQ ID NO:2, respectively; MEKK 2 nucleic acid and protein sequences by SEQ ID NO:3 and SEQ ID NO:4, respectively; MEKK 3 nucleic acid and protein sequences by SEQ ID NO:5 and SEQ ID NO:6, respectively; MEKK 4 nucleic acid and protein sequences by SEQ ID NO:7 and SEQ ID NO:8, respectively; and MEKK 5 nucleic acid and protein sequences by SEQ ID NO:9 and SEQ ID NO:10, respectively). U.S. patent application Ser. No. 08/440,421, filed May 15, 1995, discloses MEKK6 nucleic acid and protein sequences which are represented by SEQ ID NO:1 and SEQ ID NO:2, respectively. As used herein, SEQ ID NO:1 and SEQ ID NO:2 refer to MEKK1 nucleic acid and protein sequences, respectively; SEQ ID NO:3 and SEQ ID NO:4 refer to MEKK2 nucleic acid and protein sequences, respectively; SEQ ID NO:5 and SEQ ID NO:6 refer to MEKK3 nucleic acid and protein sequences, respectively; SEQ ID NO:7 and SEQ ID NO:8 refer to MEKK4 nucleic acid and protein sequences, respectively; SEQ ID NO:9 and SEQ ID NO:10 refer to MEKK5 nucleic acid and protein sequences, respectively; and SEQ ID NO:11 and SEQ ID NO:12 refer to MEKK6 nucleic acid and protein sequences, respectively. The substantially pure MEKK protein capable of regulating the activity of MEKK protein, said protein having an amino acid sequence distinct from Raf protein.

The present invention also includes a formulation comprising at least one isolated protein having at least a portion of an amino acid sequence encoded by a nucleic acid sequence that is capable of hybridizing under stringent conditions with a nucleic acid molecule encoding the amino acid sequence shown in SEQ ID NO:1 and SEQ ID NO:2.

One aspect of the present invention includes an isolated nucleic acid molecule having a sequence encoding a protein capable of phosphorylating mammalian MEK independent of Raf protein and capable of regulating the activity of MAPK protein. In particular, the present invention includes an isolated nucleic acid molecule capable of hybridizing under stringent conditions with the nucleic acid sequence shown in SEQ ID NO:1 and SEQ ID NO:2.

Another aspect of the present invention includes a recombinant molecule, comprising a nucleic acid molecule capable of hybridizing under stringent conditions with the nucleic acid sequence shown in SEQ ID NO:1 and SEQ ID NO:2.

Yet another aspect of the present invention is a recombinant cell transformed with a recombinant molecule, comprising a nucleic acid molecule operatively linked to an expression vector, the nucleic acid molecule comprising a nucleic acid sequence capable of hybridizing under stringent conditions with the nucleic acid sequence shown in SEQ ID NO:1 and SEQ ID NO:2.

The present invention also includes a method for regulating the homeostasis of a cell comprising regulating the activity of an MEKK-dependent pathway relative to the activity of a Raf-dependent pathway in the cell. In particular, the method comprises regulating the apoptosis of the cell. Such a method is useful for the treatment of a medical disorder. In particular, the method is useful for inhibiting tumorigenesis and autoimmunity.

According to the present invention, the method for treatment of a disease, comprises administering to a patient an effective amount of a therapeutic compound comprising at least one regulatory molecule including a molecule capable of decreasing the activity of a Raf-dependent pathway, a molecule capable of increasing the activity of an MEKK-dependent pathway, and combinations thereof, in which the effective amount comprises an amount which results in the depletion of harmful cells involved in the disease.

Also included in the present invention is a therapeutic compound capable of regulating the activity of an MEKK-dependent pathway in a cell identified by a process, comprising: (a) contacting a cell with a putative regulatory molecule; and (b) determining the ability of the putative regulatory compound to regulate the activity of an MEKK-dependent pathway in the cell by measuring the activation of at least one member of said MEKK-dependent pathway.

One embodiment of the present invention includes a substantially pure protein, in which the protein is isolated using an antibody capable of selectively binding to an MEKK protein capable of phosphorylating mammalian MEK protein and capable of regulating the activity of MAPK protein independent of Raf protein, the antibody capable of being produced by a method comprising: (a) administering to an animal an effective amount of a substantially pure MEKK protein of the present invention; and (b) recovering an antibody capable of selectively binding to the MEKK protein.

Another embodiment of the present invention includes an isolated antibody capable of selectively binding to an MEKK protein, the antibody capable of being produced by a method comprising administering to an animal an effective amount of a substantially pure protein of the present invention, and recovering an antibody capable of selectively binding to the MEKK protein.

This invention further relates to biological responses modulated by the MAPK pathway, which is regulated by signalling through interactions of Ras protein and MEK kinase protein. These biological responses include activation of immune responses, especially in B cells and in T cells; other biological responses regulated by the Ras protein; MEK kinase interaction include activation, proliferation and immunoglobulin class switching. Methods herein disclosed may be used to specifically modulate the interaction of Ras protein and MEK kinase protein, or to identify compounds which specifically act to alter the interaction of Ras protein and MEK kinase protein. Alternatively, such biological responses regulated by the interaction of Ras protein and MEK kinase protein may be manipulated to achieve therapeutic results in vivo by methods of the present invention.

BACKGROUND OF THE INVENTION

Mitogen-activated protein kinase (MAPKs) (also called extracellular signal-regulated kinases or ERKs) are rapidly activated in response to ligand binding by both growth factor receptors that are tyrosine k-nases (such as the epidermal growth factor (EGF) receptor) and receptors that are coupled to heterotrimeric guanine nucleotide binding proteins (G proteins) such as the thrombin receptor. The MAPKs appear to integrate multiple intracellular signals transmitted by various second messengers. MAPKs phosphorylate and regulate the activity of enzymes and transcription factors including the EGF receptor, Rsk 90, phospholipase $A_2$, c-Myc, c-Jun and Elk-1/TCF. Although the rapid activation of MAPKs by receptors that are tyrosine kinases is dependent on Ras, G protein-mediated activation of MAPK appears to occur through pathways dependent and independent of Ras.

Complementation analysis of the pheromone-induced signaling pathway in yeast has defined a protein kinase system that controls the activity of Spk1 and Fus3-Kss1, the *Schizosaccharomyces pombe* and *Saccharomyces cerevisiae* homologs of MAPK (see for example, B. R. Cairns et al., *Genes and Dev.* 6, 1305 (1992); B. J. Stevenson et al., *Genes and Dev.* 6, 1293 (1992); S. A. Nadin-Davis et al., *EMBO J.* 7, 985 (1988); Y. Wang et al., *Mol. Cell. Biol.* 11, 3554 (1991). In *S. cerevisiae*, the protein kinase Ste7 is the upstream regulator of Fus3-Kss1 activity; the protein kinase Ste[11] regulates Ste7. The *S. pombe* gene products Byr1 and Byr2 are homologous to Ste7 and Ste11, respectively. The MEK (MAPK Kinase or ERK Kinase) or MKK (MAP Kinase kinase) enzymes are similar in sequence to Ste7 and Byr1. The MEKs phosphorylate MAPKs on both tyrosine and threonine residues which results in activation of MAPK. The mammalian serine-threonine protein kinase Raf phosphorylates and activates MEK, which leads to activation of MAPK. Raf is activated in response to growth factor receptor tyrosine kinase activity and therefore Raf may activate MAPK in response to stimulation of membrane-associated tyrosine kinases. Raf is unrelated in sequence to Ste11 and Byr2. Thus, Raf may represent a divergence in mammalian cells from the pheromone-responsive protein kinase system defined in yeast. Cell and receptor specific differences in the regulation of MAPKs suggest that other Raf independent regulators of mammalian MEKs exist.

Certain biological functions, such as growth and differentiation, are tightly regulated by signal transduction pathways within cells. Signal transduction pathways maintain the balanced steady state functioning of a cell. Disease states can arise when signal transduction in a cell breaks down, thereby removing the tight control that typically exists over cellular functions. For example, tumors develop when regulation of cell growth is disrupted enabling a clone of cells to expand indefinitely. Because signal transduction networks regulate a multitude of cellular functions depending upon the cell type, a wide variety of diseases can result from abnormalities in such networks. Devastating diseases such as cancer, autoimmune diseases, allergic reactions, inflammation, neurological disorders and hormone-related diseases can result from abnormal signal transduction.

Despite a long-felt need to understand and discover methods for regulating cells involved in various disease states, the complexity of signal transduction pathways has precluded the development of products and processes for regulating cellular function by manipulating signal transduction pathways in a cell. As such, there remains a need for products and processes that permit the implementation of predictable controls of signal transduction in cells, thus enabling the treatment of various diseases that are caused by abnormal cellular function.

BRIEF DESCRIPTION OF THE FIGURES

FIG. 5 shows immunoblotting of MEKK protein in immunoprecipitates and cell lysates.

FIG. 27 shows 3 representative microscopic views of apoptotic REF52 cells expressing MEKK protein.

FIG. 28 shows 3 representative microscopic views of apoptotic Swiss 3T3 cells expressing MEKK protein.

FIG. 33 shows the binding of recombinant $MEKK_{COOH}$-His protein to GST-$Ras^{V12}$(GTPγS) agarose.

FIG. 34 shows the inhibition of binding of recombinant $MEKK_{COOH}$-His protein to GST-$Ras^{V12}$(GTPγS) agarose by Ras effector domain peptide.

DETAILED DESCRIPTION OF THE INVENTION

Figure 1:
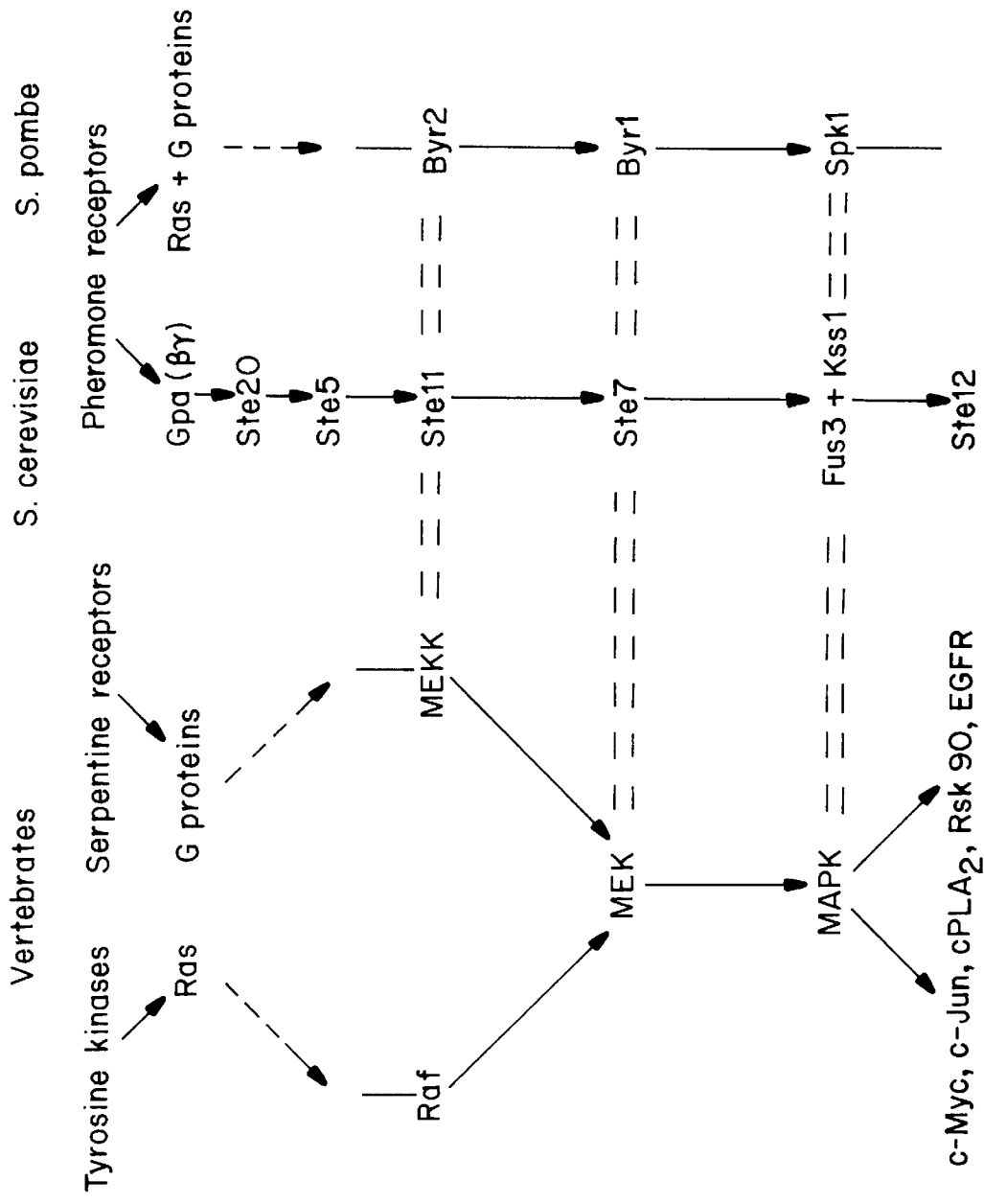
FIG. 1 is a schematic representation of the signal pathways of vertebrates and yeast.

The present invention relates to a novel mitogen ERK kinase kinase protein (MEKK) capable of regulating signal transduction in cells. The present invention includes a novel method for treating disease by regulating the activity of cells involved in such disease. The present invention is particularly advantageous in that the novel product and method of the present invention is capable of regulating a signal transduction pathway that can lead to cellular apoptosis.

One embodiment of the present invention is an isolated MEKK protein. According to the present invention, an isolated protein is a protein that has been removed from its natural milieu. An isolated MEKK protein can, for example, be obtained from its natural source, be produced using recombinant DNA technology, or be synthesized chemically. As used herein, an isolated MEKK protein can be a full-length MEKK protein or any homologue of such a protein, such as an MEKK protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycosylphosphatidyl inositol), wherein the modified protein is capable of phosphorylating mitogen ERK kinase (MEK) and/or Jun ERK kinase (JEK). A homologue of an MEKK protein is a protein having an amino acid sequence that is sufficiently similar to a natural MEKK protein amino acid sequence that a nucleic acid sequence encoding the homologue is capable of hybridizing under stringent conditions to (i.e., with) a nucleic acid sequence encoding the natural MEKK protein amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual,* Cold Spring Harbor Labs Press, 1989. A homologue of an MEKK protein also includes a protein having an amino acid sequence that is sufficiently cross-reactive such that the homologue has the ability to elicit an immune response against at least one epitope of a naturally-occurring MEKK protein.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition, percent homology between the nucleic acid molecule and complementary sequence, as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an MEKK protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an MEKK protein homologue of the present invention is from about 4 to about 6 amino acids in length, with preferred sizes depending on whether a full-length, multivalent protein (i.e., fusion protein having more than one domain each of which has a function), or a functional portion of such a protein is desired.

MEKK protein homologues can be the result of allelic variation of a natural gene encoding an MEKK protein. A natural gene refers to the form of the gene found most often in nature. MEKK protein homologues can be produced using techniques known in the art including, but not limited to, direct modifications to a gene encoding a protein using, for example, classic or recombinant DNA techniques to effect random or targeted mutagenesis. The ability of an MEKK protein homologue to phosphorylate MEK and/or JEK protein can be tested using techniques known to those skilled in the art. Such techniques include phosphorylation assays described in detail in the Examples section.

In one embodiment, an MEKK protein of the present invention is capable of regulating an MEKK-dependent pathway. According to the present invention, an MEKK-dependent pathway refers generally to a pathway in which MEKK protein regulates a pathway substantially independent of Raf, and a pathway in which MEKK protein regulation converges with common members of a pathway involving Raf protein, in particular, MEK protein (see FIG. 2). A suitable MEKK-dependent pathway includes a pathway involving MEKK protein and JEK protein, but not Raf protein. One of skill in the art can determine that regulation of a pathway by an MEKK protein is substantially independent of Raf by comparing the ability of an MEKK protein and a Raf protein to regulate the phosphorylation of a downstream member of such pathway using, for example, the general method described in Example 16. An MEKK protein regulates a pathway substantially independently of Raf protein if the MEKK protein induces phosphorylation of a member of the pathway downstream of MEKK (e.g., proteins including JEK, Jun kinase, Jun and/or ATF-2) by an amount significantly greater than that seen when Raf protein is utilized. For example, MEKK induction of phosphorylation of JNK is preferably at least about 10-fold, more preferably at least about 20-fold and even more preferably at least about 30-fold, greater phosphorylation of JNK protein than the phosphorylation induced when using Raf protein. If MEKK induction of phosphorylation is similar to Raf protein induction of phosphorylation, then one of skill in the art can conclude that regulation of a pathway by an MEKK protein includes members of a signal transduction pathway that could also include Raf protein. For example, MEKK induction of phosphorylation of MAPK is of a similar magnitude as induction of phosphorylation with Raf protein.

A "Raf-dependent pathway" can refer to a signal transduction pathway in which Raf protein regulates a signal transduction pathway substantially independently of MEKK protein, and a pathway in which Raf protein regulation converges with common members of a pathway involving MEKK protein. The independence of regulation of a pathway by a Raf protein from regulation of a pathway by an MEKK protein can be determined using methods similar to those used to determine MEKK independence.

In another embodiment, an MEKK protein is capable of regulating the activity of signal transduction proteins including, but not limited to, mitogen ERK kinase (MEK), mitogen activated protein kinase (MAPK), transcription control factor (TCF), Ets-like-1 transcription factor (Elk-1), Jun ERK kinase (JEK), Jun kinase (JNK; which is equivalent to SAPK), stress activated MAPK proteins, Jun, activating transcription factor-2 (ATF-2) and/or Myc protein. As used herein, the "activity" of a protein can be directly correlated with the phosphorylation state of the protein and/or the ability of the protein to perform a particular function (e.g., phosphorylate another protein or regulate transcription). Preferred MEK proteins regulated by an MEKK protein of the present invention include MEK-1 and/or MEK-2. Preferred MAPK proteins regulated by an MEKK protein of the present invention include p38 MAPK, p42 MAPK (which is equivalent to ERK2) and/or p44 (which is equivalent to ERK1) MAPK. Preferred stress activated MAPK proteins regulated by an MEKK protein of the present invention include Jun kinase (JNK), stress activated MAPK-A and/or stress activated MAPK-β.

An MEKK protein of the present invention is capable of increasing the activity of an MEK protein over basal levels of MEK (i.e., levels found in nature when not stimulated). For example, an MEKK protein is preferably capable of increasing the phosphorylation of an MEK protein by at least about 2-fold, more preferably at least about 3-fold, and even more preferably at least about 4-fold over basal levels when measured under conditions described in Example 9.

A preferred MEKK protein of the present invention is also capable of increasing the activity of an MAPK protein over basal levels of MAPK (i.e., levels found in nature when not stimulated). For example, an MEKK protein of the present invention is preferably capable of increasing MAPK activity at least about 2-fold, more preferably at least about 3-fold, and even more preferably at least about 4-fold over basal activity when measured under the conditions described in Example 3.

Moreover, an MEKK protein of the present invention is capable of increasing the activity of a JNK protein. JNK regulates the activity of the transcription factor JUN which is involved in controlling the growth and differentiation of different cell types, such as T cells, neural cells or fibroblasts. JNK shows structural and regulatory homologies with MAPK. For example, an MEKK protein of the present invention is preferably capable of inducing the phosphorylation of JNK protein at least about 30 times more than Raf, more preferably at least about 40 times more than Raf, and even more preferably at least about 50 times more than Raf, when measured under conditions described in Example 16.

In addition, an MEKK protein of the present invention is capable of binding to Ras protein. In particular, an MEKK protein is capable of binding to a Ras protein that is associated with GTP. According to the present invention, an MEKK protein binds to Ras via the COOH terminal region of the MEKK protein.

In a preferred embodiment, an MEKK protein of the present invention is capable of phosphorylating MEK, MKK, Jun kinase kinase (JNKK) and stress activated ERK kinase (SEK), in particular MEK1, MEK2, MKK1, MKK2, MKK3, MKK4, JNKK1, JNKK2, SEK1 and SEK2 protein. As described herein, MEK1 and MEK2 are equivalent to MKK1 and MKK2, respectively and are referred to as MEK1 and MEK2. In addition, JNKK1 and JNKK2 are equivalent to MKK3 and MKK4, which are equivalent to SEK1 and SEK2, respectively, and are referred to herein as JNKK1 and JNKK2.

A preferred MEKK protein of the present invention is additionally capable of inducing the phosphorylation of a c-Myc transcriptional transactivation domain protein in such a manner that the phosphorylated transcriptional transactivation domain of c-Myc is capable of regulating gene transcription. The ability of an MEKK protein to regulate phosphorylation of a c-Myc transcriptional transactivation domain protein exceeds the ability of Raf protein or cyclic AMP-dependent protein kinase to regulate a c-Myc protein. For example, an MEKK protein of the present invention is preferably capable of inducing luciferase gene transcription by phosphorylated c-Myc transcriptional transctivation domain protein at least about 25-fold, more preferably at least about 35-fold, and even more preferably at least about 45-fold, over Raf induction when measured under the conditions described in Example 17.

Another aspect of the present invention relates to the ability of MEKK activity to be stimulated by growth factors including, but not limited to, epidermal growth factor (EGF), neuronal growth factor (NGF), tumor necrosis factor (TNF), C5A, interleukin-8 (IL-8), monocyte chemotactic protein 1 (MIP1α), monocyte chemoattractant protein 1 (MCP-1), platelet activating factor (PAF), N-Formyl-methionyl-leucyl-phenylalanine (FMLP), leukotriene $B_4$ ($LTB_4R$), gastrin releasing peptide (GRP), IgE, major histocompatibility protein (MHC), peptide, superantigen, antigen, vasopressin, thrombin, bradykinin and acetylcholine. In addition, the activity of an MEKK protein of the present invention is capable of being stimulated by compounds including phorbol esters such as TPA. A preferred MEKK protein is also capable of being stimulated by EGF, NGF and TNF (especially TNFα).

Preferably, the activity of an MEKK protein of the present invention is capable of being stimulated at least 2-fold over basal levels (i.e., levels found in nature when not stimulated), more preferably at least about 4-fold over basal levels and even more preferably at least about 6-fold over basal levels, when a cell producing the MEKK protein is contacted with EGF under the conditions described in Example 3.

Similarly, the activity of an MEKK protein of the present invention is capable of being stimulated at least 1-fold over basal levels, more preferably at least about 2-fold over basal levels and even more preferably at least about 3-fold over basal levels by NGF stimulation, when a cell producing the MEKK protein is contacted with NGF under the conditions described in Example 9.

Preferably, an MEKK protein of the present invention is capable of being stimulated at least 0.5-fold over basal levels, more preferably at least about 1-fold over basal levels and even more preferably at least about 2-fold over basal levels by TPA stimulation when a cell producing the MEKK protein is contacted with TPA under the conditions described in Example 9.

TNF is capable of regulating cell death and other functions in different cell types. The present inventor discovered that MEKK stimulation by TNF is independent of Raf. Similarly, the present inventor is the first to appreciate that an MEKK protein can be directly stimulated by ultraviolet light (UV) damage of cells while a Raf-dependent pathway cannot. Therefore, both TNF and UV stimulate MEKK activity without substantially activating Raf. In addition, both UV and TNF activation of MEKK is Ras dependent.

Another aspect of the present invention is the recognition that an MEKK protein of the present invention is capable of regulating the apoptosis of a cell, an ability not shared by Raf protein. As used herein, apoptosis refers to the form of cell death that comprises: progressive contraction of cell volume with the preservation of the integrity of cytoplasmic organelles; condensation of chromatin, as viewed by light or electron microscopy; and DNA cleavage, as determined by centrifuged sedimentation assays. Cell death occurs when the membrane integrity of the cell is lost and cell lysis occurs. Apoptosis differs from necrosis in which cells swell and eventually rupture.

A preferred MEKK protein of the present invention is capable of inducing the apoptosis of cells, such that the cells have characteristics substantially similar to cytoplasmic shrinkage and/or nuclear condensation as shown in FIGS. 24, 25, 26, 27 and 28. The apoptotic cells in FIGS. 24 through 28 were obtained when cells were microinjected with expression plasmids encoding MEKK protein. Injected cells were identified using anti-β-Gal antibody and the DNA of the cells were stained with propidium iodide. Cytoplasmic organization was monitored using an anti-tubulin antibody. The cells were then imaged by differential fluorescent imaging microscopy using techniques standard in the art. The cells demonstrated apoptosis by displaying a morphology having cytoplasmic shrinkage and nuclear condensation.

Figure 2:
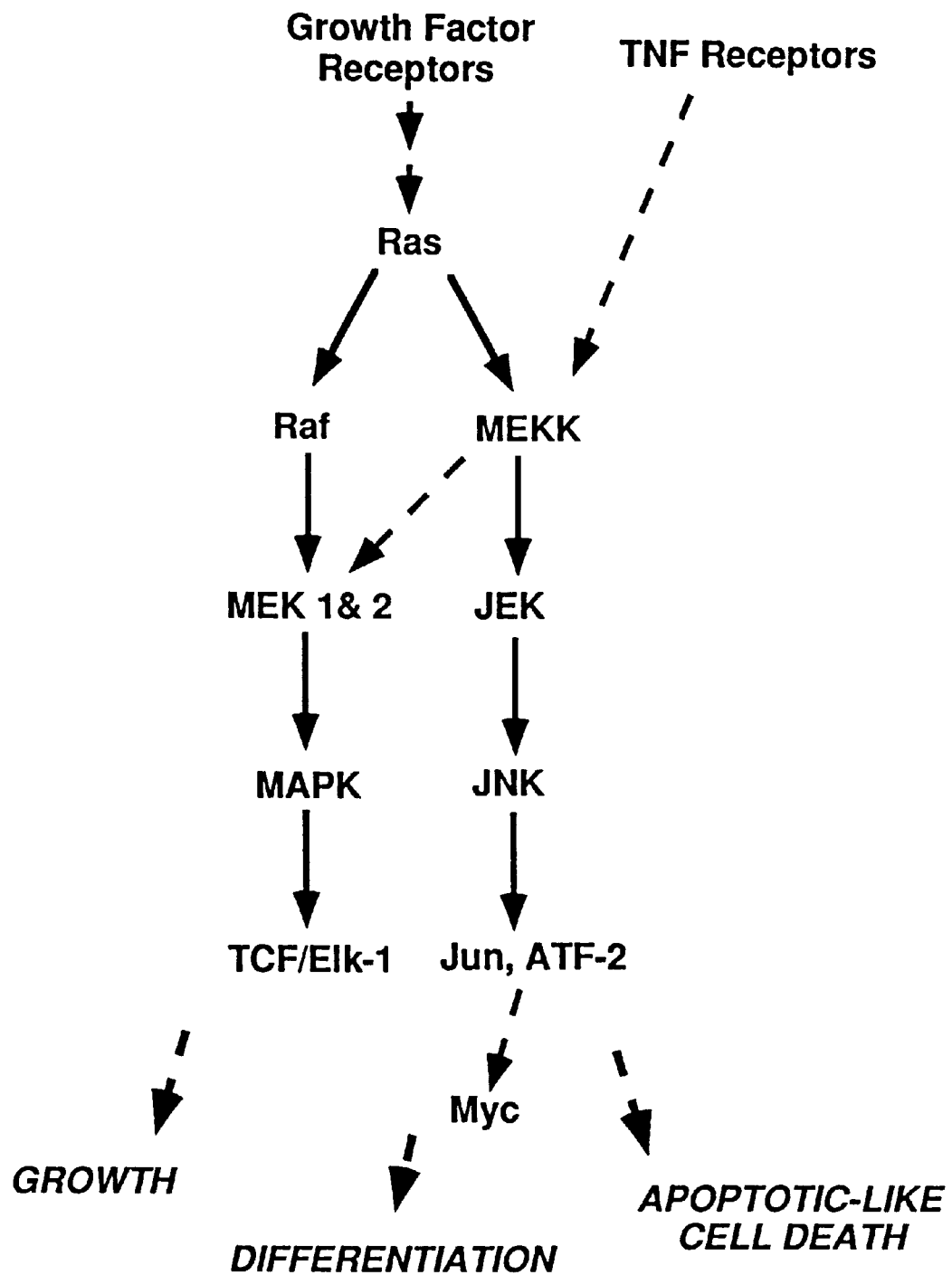
FIG. 2 is a schematic representation of the dual MEKK and Raf pathways divergent from Ras protein pathway.

A schematic representation of the cell growth regulatory signal transduction pathway that is MEKK dependent is shown in FIG. 2. An MEKK protein of the present invention is capable of regulating the activity of JEK protein, JNK protein, Jun protein and/or ATF-2 protein, and Myc protein, such regulation being substantially, if not entirely, independent of Raf protein. Such Raf-independent regulation can regulate the growth characteristics of a cell, including the apoptosis of a cell. In addition, an MEKK protein of the present invention is capable of regulating the activity of MEK protein, which is also capable of being regulated by Raf protein. As such, an MEKK protein of the present invention is capable of regulating the activity of MAPK protein and members of the Ets family of transcription factors, such as TCF protein, also referred to as Elk-1 protein.

Referring to FIG. 2, an MEKK protein of the present invention is capable of being activated by a variety of growth factors capable of activating Ras protein. In addition, an MEKK protein is capable of activating JNK protein which is also activated by Ras protein, but is not activated by Raf protein. As such, an MEKK protein of the present invention comprises a protein kinase at a divergence point in a signal transduction pathway initiated by different cell surface receptors. An MEKK protein is also capable of being regulated by TNF protein independent of Raf, thereby indicating an association of MEKK protein to a novel signal transduction pathway which is independent of Ras protein and Raf protein.

Thus, an MEKK protein is capable of performing numerous unique functions independent of or by-passing Raf protein in one or more signal transduction pathways. An MEKK protein is capable of regulating the activity of MEK and/or JEK activity. As such, an MEKK protein is capable of regulating the activity of members of a signal transduction pathway that does not substantially include Raf activity. Such members include, but are not limited to, JNK, Jun, ATF and Myc protein. In addition, an MEKK protein is capable of regulating the members of a signal transduction pathway that does involve Raf, such members including, but are not limited to, MEK, MAPK and TCF. An MEKK protein of the present invention is thus capable of regulating the apoptosis of a cell independent of significant involvement by Raf protein.

In addition to the numerous functional characteristics of an MEKK protein, an MEKK protein of the present invention comprises numerous unique structural characteristics. For example, in one embodiment, an MEKK protein of the present invention includes at least one of two different structural domains having particular functional characteristics. Such structural domains include an $NH_2$-terminal regulatory domain that serves to regulate a second structural domain comprising a COOH-terminal protein kinase catalytic domain that is capable of phosphorylating an MEK protein and/or JEK protein.

According to the present invention, an MEKK protein of the present invention includes a full-length MEKK protein, as well as at least a portion of an MEKK protein capable of performing at least one of the functions defined above. The phrase "at least a portion of an MEKK protein" refers to a portion of an MEKK protein encoded by a nucleic acid molecule that is capable of hybridizing, under stringent conditions, with a nucleic acid encoding a full-length MEKK protein of the present invention. Preferred portions of MEKK proteins are useful for regulating apoptosis in a cell. Additional preferred portions have activities useful for regulating MEKK kinase activity. Suitable sizes for portions of an MEKK protein of the present invention are as disclosed for MEKK protein homologues of the present invention.

In another embodiment, an MEKK protein of the present invention includes at least a portion of an MEKK protein having molecular weights ranging from about 70 kD to about 250 kD as determined by Tris-glycine SDS-PAGE, preferably using an 8% polyacrylamide SDS gel (SDS-PAGE) and resolved using methods standard in the art. A preferred MEKK protein has a molecular weight ranging from about 75 kD to about 225 kD and even more preferably from about 80 kD to about 200 kD.

In yet another embodiment, an MEKK protein of the present invention comprises at least a portion of an MEKK protein encoded by an mRNA (messenger ribonucleic acid) ranging from about 3.5 kb to about 12.0 kb, more preferably ranging from about 4.0 kb to about 11.0 kb, and even more preferably ranging from about 4.5 kb to about 10.0 kb. Particularly preferred MEKK proteins comprise at least a portion of an MEKK protein encoded by an mRNA having a size ranging from about 4.5 kb to about 5.0 kb, a size ranging from about 6.0 kb to about 6.5 kb, a size of about 7.0 kb, or a size ranging from about 8.0 kb to about 10.0 kb.

In another embodiment, an $NH_2$-terminal regulatory domain of the present invention includes an $NH_2$-terminal comprising about 400 amino acids having at least about 10% serine and/or threonine residues, more preferably about 400 amino acids having at least about 15% serine and/or threonine residues, and even more preferably about 400 amino acids having at least about 20% serine and/or threonine residues.

A preferred an $NH_2$-terminal regulatory domain of the present invention includes an $NH_2$-terminal comprising about 360 amino acids having at least about 10% serine and/or threonine residues, more preferably about 360 amino acids having at least about 15% serine and/or threonine residues, and even more preferably about 360 amino acids having at least about 20% serine and/or threonine residues.

Another preferred an $NH_2$-terminal regulatory domain of the present invention includes an $NH_2$-terminal comprising about 370 amino acids having at least about 10% serine and/or threonine residues, more preferably about 370 amino acids having at least about 15% serine and/or threonine residues, and even more preferably about 370 amino acids having at least about 20% serine and/or threonine residues.

In one embodiment, an MEKK protein of the present invention is devoid of $SH_2$ and $SH_3$ domains.

In another embodiment, an MEKK protein of the present invention includes at least a portion of an MEKK protein homologue preferably having at least about 50%, more preferably at least about 75%, and even more preferably at least about 85% amino acid homology (identity within comparable regions) with the kinase catalytic domain of a naturally occurring MEKK protein. Another MEKK protein of the present invention also includes at least a portion of an MEKK homologue of the present invention has at least about 10%, more preferably at least about 20%, and even more preferably at least about 30% amino acid homology with the $NH_2$-terminal regulatory domain of an MEKK protein of a naturally occurring MEKK protein.

The sequences comprising the catalytic domain of an MEKK protein are involved in phosphotransferase activity, and therefore display a relatively conserved amino acid sequence. The $NH_2$-terminal regulatory domain of an MEKK protein, however, can be substantially divergent. The lack of significant homology between MEKK protein $NH_2$-terminal regulatory domains is related to the regulation of each of such domains by different upstream regulatory proteins. For example, an MEKK protein can be regulated by the protein Ras, while others can be regulated independent of Ras. In addition, some MEKK proteins can be regulated by the growth factor $TNF\alpha$, while others cannot. As such, the $NH_2$-terminal regulatory domain of an MEKK protein provides selectivity for upstream signal transduction regulation, while the catalytic domain provides for MEKK substrate selectivity function.

A preferred MEKK homologue has at least about 50%, more preferably at least about 75% and even more preferably at least about 85% amino acid homology with the kinase catalytic domain of an MEKK protein having the amino acid sequence shown in SEQ ID NO:1 and SEQ ID NO: 2. Another preferred MEKK homologue has at least about 10%, more preferably at least about 20% and even more preferably at least about 30% amino acid homology with the $NH_2$-terminal regulatory domain of an MEKK protein having the amino acid sequence shown in SEQ ID NO:1 and SEQ ID NO:2.

In a preferred embodiment, an MEKK protein of the present invention includes at least a portion of an MEKK protein homologue of the present invention that is encoded by a nucleic acid molecule having at least about 50%, more preferably at least about 75%, and even more preferably at least about 85% homology with a nucleic acid molecule encoding the kinase catalytic domain of an MEKK protein. Another preferred MEKK protein homologue is encoded by a nucleic acid molecule having at least about 10%, more preferably at least about 20%, and even more preferably at least about 30% homology with a nucleic acid molecule encoding the $NH_2$-terminal regulatory domain of an MEKK protein.

Still another preferred MEKK homologue is encoded by a nucleic acid molecule having at least about 50%, more preferably at least about 75% and even more preferably at least about 85% amino acid homology with the kinase catalytic domain of an MEKK protein encoded by the nucleic acid sequence shown in SEQ ID NO:1 and SEQ ID NO:2. An MEKK homologue also includes those encoded by a nucleic acid molecule having at least about 10%, more preferably at least about 20% and even more preferably at least about 30% amino acid homology with the NH$_2$-terminal regulatory domain of an MEKK protein encoded by the nucleic acid sequence shown in SEQ ID NO:1 and SEQ ID NO:2.

In one embodiment, an MEKK protein of the present invention, referred to here as MEKK6, comprises an MEKK protein having (i.e., including) at least a portion of the sequence shown in SEQ ID NO:1 and SEQ ID NO:2. The foregoing sequences were deduced according to methods disclosed in the Examples. It should be noted that since nucleic acid and amino acid sequencing technology is not entirely error-free, the foregoing sequences, at best, represent apparent nucleic acid and amino acid sequences of an MEKK protein of the present invention.

According to the present invention, an MEKK protein of the present invention can include MEKK proteins that have undergone post-translational modification. Such modification can include, for example, glycosylation (e.g., including addition of N-linked and/or O-linked oligosaccharides) or post-translational conformational changes or post-translational deletions.

Another embodiment of the present invention is an isolated nucleic acid molecule capable of hybridizing, under stringent conditions, with an MEKK protein gene encoding an MEKK protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with a particular desired gene (e.g., MEKK genes) under stringent hybridization conditions. An isolated nucleic acid molecule of the present invention can also be produced using recombinant DNA technology (e.g., polymerase chain reaction (PCR) amplification, cloning) or chemical synthesis. Isolated MEKK protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an MEKK protein of the present invention or to form stable hybrids under stringent conditions with natural nucleic acid molecule isolates of MEKK.

Preferred modifications to an MEKK protein nucleic acid molecule of the present invention include truncating a full-length MEKK protein nucleic acid molecule by, for example: deleting at least a portion of an MEKK protein nucleic acid molecule encoding a regulatory domain to produce a constitutively active MEKK protein; deleting at least a portion of an MEKK protein nucleic acid molecule encoding a catalytic domain to produce an inactive MEKK protein; and modifying the MEKK protein to achieve desired inactivation and/or stimulation of the protein, for example, substituting a codon encoding a lysine residue in the catalytic domain (i.e., phosphotransferase domain) with a methionine residue to inactivate the catalytic domain.

A preferred truncated MEKK nucleic acid molecule encodes a form of an MEKK protein containing a catalytic domain but that lacks a regulatory domain. Preferred catalytic domain truncated MEKK nucleic acid molecules encode residues from about 352 to about 672 of MEKK6.

Another preferred truncated MEKK nucleic acid molecule encodes a form of an MEKK protein comprising an NH$_2$-terminal regulatory domain but lacking a catalytic domain. Preferred regulatory domain truncated MEKK nucleic acid molecules encode residues from about 1 to about 369 for MEKK6, thereby removing the catalyte domain to form the truncated MEKK molecule.

An isolated nucleic acid molecule of the present invention can include a nucleic acid sequence that encodes at least one MEKK protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides that comprise the nucleic acid molecule, the two phrases can be used interchangeably. As heretofore disclosed, MEKK proteins of the present invention include, but are not limited to, proteins having full-length MEKK protein coding regions, portions thereof, and other MEKK protein homologues.

As used herein, an MEKK protein gene includes all nucleic acid sequences related to a natural MEKK protein gene such as regulatory regions that control production of an MEKK protein encoded by that gene (including, but not limited to, transcription, translation or post-translation control regions) as well as the coding region itself. A nucleic acid molecule of the present invention can be an isolated natural MEKK protein nucleic acid molecule or a homologue thereof. A nucleic acid molecule of the present invention can include one or more regulatory regions, full-length or partial coding regions, or combinations thereof. The minimal size of an MEKK protein nucleic acid molecule of the present invention is the minimal size capable of forming a stable hybrid under stringent hybridization conditions with a corresponding natural gene.

An MEKK protein nucleic acid molecule homologue can be produced using a number of methods known to those skilled in the art (see, e.g., Sambrook et al., ibid.) . For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to phosphorylate MEK protein or JEK protein) and/or by hybridization with isolated MEKK protein nucleic acids under stringent conditions.

One embodiment of the present invention is an MEKK protein nucleic acid molecule capable of encoding at least a portion of an MEKK protein, or a homologue thereof, as described herein. A preferred nucleic acid molecule of the present invention includes, but is not limited to, a nucleic acid molecule that encodes a protein having at least a portion of an amino acid sequence shown in SEQ ID NO:1 and SEQ ID NO:2, or homologues thereof.

A preferred nucleic acid molecule of the present invention is capable of hybridizing under stringent conditions to a nucleic acid that encodes at least a portion of an MEKK protein, or a homologue thereof. Also preferred is an MEKK protein nucleic acid molecule that includes a nucleic acid sequence having at least about 50%, preferably at least about 75%, and more preferably at least about 85% homology with the corresponding region(s) of the nucleic acid sequence encoding the catalytic domain of an MEKK protein, or a homologue thereof. Also preferred is an MEKK protein nucleic acid molecule that includes a nucleic acid sequence having at least about 20%, preferably at least about 30%, and more preferably at least about 40% homology with the corresponding region(s) of the nucleic acid sequence encoding the $NH_2$-terminal regulatory domain of an MEKK protein, or a homologue thereof. A particularly preferred nucleic acid sequence is a nucleic acid sequence having at least about 50%, preferably at least about 75%, and more preferably at least about 85% homology with a nucleic acid sequence encoding the catalytic domain of an amino acid sequence shown in SEQ ID NO:1 and SEQ ID NO:2. Another particularly preferred nucleic acid sequence is a nucleic acid sequence having at least about 20%, preferably at least about 30%, and more preferably at least about 40% homology with a nucleic acid sequence encoding the $NH_2$-terminal regulatory domain of the amino acid sequence shown in SEQ ID NO:1 and SEQ ID NO:2.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having the nucleic acid sequence shown in SEQ ID NO:1 and SEQ ID NO:2.

Knowing a nucleic acid molecule of an MEKK protein of the present invention allows one skilled in the art to make copies of that nucleic acid molecule as well as to obtain additional portions of MEKK protein-encoding genes (e.g., nucleic acid molecules that include the translation start site and/or transcription and/or translation control regions), and/or MEKK protein nucleic acid molecule homologues. Knowing a portion of an amino acid sequence of an MEKK protein of the present invention allows one skilled in the art to clone nucleic acid sequences encoding such an MEKK protein.

The present invention also includes nucleic acid molecules that are oligonucleotides capable of hybridizing, under stringent conditions, with complementary regions of other, preferably longer, nucleic acid molecules of the present invention that encode at least a portion of an MEKK protein, or a homologue thereof. A preferred oligonucleotide is capable of hybridizing, under stringent conditions, with a nucleic acid molecule that is capable of encoding at least a portion of the amino acid sequence shown in SEQ ID NO:1 and SEQ ID NO:2, or homologues thereof. A more preferred oligonucleotide is capable of hybridizing to a nucleic acid molecule having the nucleic acid sequence shown in SEQ ID NO:1 and SEQ ID NO:2, or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of MEKK proteins by cells. Such therapeutic applications include the use of such oligonucleotides in, for example, antisense-, triplex formation-, ribozyme- and/or RNA drug-based technologies. The present invention, therefore, includes use of such oligonucleotides and methods to interfere with the production of MEKK proteins.

In one embodiment, an isolated MEKK protein of the present invention is produced by culturing a cell capable of expressing the protein under conditions effective to produce the protein, and recovering the protein. A preferred cell to culture is a recombinant cell that is capable of expressing the MEKK protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

The present invention also includes a recombinant vector which includes at least one MEKK protein nucleic acid molecule of the present invention inserted into any vector capable of delivering the nucleic acid molecule into a host cell. Such a vector contains heterologous nucleic acid sequences, for example nucleic acid sequences that are not naturally found adjacent to MEKK protein nucleic acid molecules of the present invention. The vector can be either RNA or DNA, and either prokaryotic or eukaryotic, and is typically a virus or a plasmid. Recombinant vectors can be used in the cloning, sequencing, and/or otherwise manipulating of MEKK protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

Preferred nucleic acid molecules to insert into a recombinant vector includes a nucleic acid molecule that encodes at least a portion of an MEKK protein, or a homologue thereof. A more preferred nucleic acid molecule to insert into a recombinant vector includes a nucleic acid molecule encoding at least a portion of the amino acid sequence shown in SEQ ID NO:1 and SEQ ID NO:2, or homologues thereof. An even more preferred nucleic acid molecule to insert into a recombinant vector includes the nucleic acid molecule shown in SEQ ID NO:1 and SEQ ID NO:2, or complements thereof.

Suitable host cells for transforming a cell can include any cell capable of producing MEKK proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with mammalian cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, baculovirus, vaccinia virus, herpesvirus, poxvirus, adenovirus, simian virus 40, retrovirus actin, retroviral long terminal repeat, Rous sarcoma virus, heat shock, phosphate and nitrate transcription control sequences, as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an MEKK protein.

Preferred nucleic acid molecules for insertion into an expression vector include nucleic acid molecules that encode at least a portion of an MEKK protein, or a homologue thereof. A more preferred nucleic acid molecule for insertion into an expression vector includes a nucleic acid molecule encoding at least a portion of the amino acid sequence shown in SEQ ID NO:1 and SEQ ID NO:2, or homologues thereof. An even more preferred nucleic acid molecule for insertion into an expression vector includes the nucleic acid molecule shown in SEQ ID NO:1 and SEQ ID NO:2, or complements thereof.

Expression vectors of the present invention may also contain fusion sequences which lead to the expression of inserted nucleic acid molecules of the present invention as fusion proteins. Inclusion of a fusion sequence as part of an MEKK nucleic acid molecule of the present invention can enhance the stability during production, storage and/or use of the protein encoded by the nucleic acid molecule. Furthermore, a fusion segment can function as a tool to simplify purification of an MEKK protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an MEKK protein. Linkages between fusion segments and MEKK proteins can be constructed to be susceptible to cleavage to enable straight-forward recovery of the MEKK proteins. Fusion proteins are preferably produced by culturing a recombinant cell transformed with a fusion nucleic acid sequence that encodes a protein including the fusion segment attached to either the carboxyl and/or amino terminal end of an MEKK protein.

A recombinant cell of the present invention includes any cells transformed with at least one of any nucleic acid molecule of the present invention. A preferred recombinant cell is a cell transformed with at least one nucleic acid molecule that encodes at least a portion of an MEKK protein, or a homologue thereof. A more preferred recombinant cell is transformed with at least one nucleic acid molecule that is capable of encoding at least a portion of the amino acid sequence shown in SEQ ID NO:1 and SEQ ID NO:2, or homologues thereof. An even more preferred recombinant cell is transformed with at least one nucleic acid molecule shown in SEQ ID NO:1 and SEQ ID NO:2, or complements thereof. Particularly preferred recombinant cells include mammalian cells involved in a disease transformed with at least one of the aforementioned nucleic acid molecules. Methods to improve expression of transformed nucleic acid molecules are disclosed in U.S. Pat. No. 5,405,941, which is incorporated herein by this reference.

As used herein, amplifying the copy number of a nucleic acid sequence in a cell can be accomplished either by increasing the copy number of the nucleic acid sequence in the cell's genome or by introducing additional copies of the nucleic acid sequence into the cell by transformation. Copy number amplification is conducted in a manner such that greater amounts of enzyme are produced, leading to enhanced conversion of substrate to product. For example, recombinant molecules containing nucleic acids of the present invention can be transformed into cells to enhance enzyme synthesis. Transformation can be accomplished using any process by which nucleic acid sequences are inserted into a cell. Prior to transformation, the nucleic acid sequence on the recombinant molecule can be manipulated to encode an enzyme having a higher specific activity.

In accordance with the present invention, recombinant cells can be used to produce an MEKK protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an MEKK protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant MEKK proteins may either remain within the recombinant cell or be secreted into the fermentation medium. The phrase "recovering the protein" refers simply to collecting the whole fermentation medium containing the protein and need not imply additional steps of separation or purification. MEKK proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

In addition, an MEKK protein of the present invention can be produced by isolating the MEKK protein from cells expressing the MEKK protein recovered from an animal. For example, a cell type, such as T cells, can be isolated from the thymus of an animal. MEKK protein can then be isolated from the isolated T cells using standard techniques described herein.

The present invention also includes a method to identify compounds capable of regulating signals initiated from a receptor on the surface of a cell, such signal regulation involving in some respect, MEKK protein. Such a method comprises the steps of: (a) contacting a cell containing an MEKK protein with a putative regulatory compound; (b) contacting the cell with a ligand capable of binding to a receptor on the surface of the cell; and (c) assessing the ability of the putative regulatory compound to regulate cellular signals by determining activation of a member of an MEKK-dependent pathway of the present invention. A preferred method to perform step (c) comprises measuring the phosphorylation of a member of an MEKK-dependent pathway. Such measurements can be performed using immunoassays having antibodies specific for phosphotyrosines, phosphoserines and/or phosphothreonines. Another preferred method to perform step (c) comprises measuring the ability of the MEKK protein to phosphorylate a substrate molecule comprising a protein including JEK, MEK1, MEK2, JNKK1, JNKK2, Raf-1, Ras-GAP and neurofibromin using methods described herein. Preferred substrates include JEK, MEK1, MEK2, JNKK1 and JNKK2. Yet another preferred method to perform step (c) comprises determining the ability of MEKK protein to bind to Ras protein. In particular, determining the ability of MEKK protein to bind to GST-Ras$^{V12}$(GTPγS).

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi) or by rational drug design.

In another embodiment, a method to identify compounds capable of regulating signal transduction in a cell can comprise the steps of: (a) contacting a putative inhibitory compound with an MEKK protein to form a reaction mixture; (b) contacting the reaction mixture with MEK protein; and (c) assessing the ability of the putative inhibitory compound to inhibit phosphorylation of the MEK protein by the MEKK protein. The results obtained from step (c) can be compared with the ability of a putative inhibitory compound to inhibit the ability of Raf protein to phosphorylate MEK protein, to determine if the compound can selectively regulate signal transduction involving MEKK protein independent of Raf protein. MEKK, MEK and Raf proteins used in the foregoing methods can be recombinant proteins or naturally-derived proteins.

In another embodiment, a method to identify compounds capable of regulating signal transduction in a cell can comprise the steps of: (a) contacting a putative inhibitory compound with either an MEKK protein or a Ras protein, or functional equivalents thereof, to form a first reaction mixture; (b) combining the first reaction mixture with either Ras protein (or a functional equivalent thereof) if MEKK protein was used in the first reaction mixture, or MEKK protein (or a functional equivalent thereof) if Raf protein if MEKK protein was added to the first reaction mixture; and (c) assessing the ability of the putative inhibitory compound to inhibit the binding of the Ras protein to the MEKK protein. The lack of binding of the MEKK protein to the Ras protein indicates that the putative inhibitory compound is effective at inhibiting binding between MEKK and Ras. MEKK and Ras proteins used in the foregoing method can be recombinant proteins or naturally-derived proteins. Preferred Ras protein for use with the foregoing method includes, but is not limited to, GST-Ras$^{V12}$(GTPγS). Preferred MEKK protein for use with the method includes recombinant MEKK protein. More preferred MEKK protein includes at least a portion of an MEKK protein having the kinase domain of MEKK. Even more preferred MEKK protein includes a protein encoded by p-MEKK1 (as described in Example 20), MEKK$_{COOH}$ (as described in Example 21) and/or MEKK$_{COOH}$-His (as described in Example 22).

The inhibition of binding of MEKK protein to Ras protein can be determined using a variety of methods known in the art. For example, immunoprecipitation assays can be performed to determine if MEKK and Ras co-precipitate. In addition, immunoblot assays can be performed to determine if MEKK and Ras co-migrate when resolved by gel electrophoresis. Another method to determine binding of MEKK to Ras comprises combining a substrate capable of being phosphorylated by MEKK protein with the Ras protein of the reaction mixture of step (b). In this method, Ras protein is separated from the reaction mixture of step (b) following incubation with MEKK protein. If MEKK protein is able to bind to the Ras, then the bound MEKK will be co-isolated with the Ras protein. The substrate is then added to the isolated Ras protein. Any co-isolated MEKK protein will phosphorylate the substrate. Thus, inhibition of binding between MEKK and Ras can be measured by determining the extent of phosphorylation of the substrate upon combination with the isolated Ras protein. The extent of phosphorylation can be determined using a variety of methods known in the art, including kinase assays using $[\gamma^{32}P]ATP$.

Moreover, one can determine whether the site of inhibitory action along a particular signal transduction pathway involves both Raf and MEKK proteins by carrying out experiments set forth above (i.e., see discussion on MEKK-dependent pathways).

Another aspect of the present invention includes a kit to identify compounds capable of regulating signals initiated from a receptor on the surface of a cell, such signals involving in some respect, MEKK protein. Such kits include: (a) at least one cell containing MEKK protein; (b) a ligand capable of binding to a receptor on the surface of the cell; and (c) a means for assessing the ability of a putative regulatory compound to alter phosphorylation of the MEKK protein. Such a means for detecting phosphorylation include methods and reagents known to those of skill in the art, for example, phosphorylation can be detected using antibodies specific for phosphorylated amino acid residues, such as tyrosine, serine and threonine. Using such a kit, one is capable of determining, with a fair degree of specificity, the location along a signal transduction pathway of particular pathway constituents, as well as the identity of the constituents involved in such pathway, at or near the site of regulation.

In another embodiment, a kit of the present invention can includes: (a) MEKK protein; (b) MEK protein; and (c) a means for assessing the ability of a putative inhibitory compound to inhibit phosphorylation of the MEK protein by the MEKK protein. A kit of the present invention can further comprise Raf protein and a means for detecting the ability of a putative inhibitory compound to inhibit the ability of Raf protein to phosphorylate the MEK protein.

Another aspect of the present invention relates to the treatment of an animal having a medical disorder that is subject to regulation or cure by manipulating a signal transduction pathway in a cell involved in the disorder. Such medical disorders include disorders which result from abnormal cellular growth or abnormal production of secreted cellular products. In particular, such medical disorders include, but are not limited to, cancer, autoimmune disease, inflammatory responses, allergic responses and neuronal disorders, such as Parkinson's disease and Alzheimer's disease. Preferred cancers subject to treatment using a method of the present invention include, but are not limited to, small cell carcinomas, non-small cell lung carcinomas with overexpressed EGF receptors, breast cancers with overexpressed EGF or Neu receptors, tumors having overexpressed growth factor receptors of established autocrine loops and tumors having overexpressed growth factor receptors of established paracrine loops. According to the present invention, the term treatment can refer to the regulation of the progression of a medical disorder or the complete removal of a medical disorder (e.g., cure). Treatment of a medical disorder can comprise regulating the signal transduction activity of a cell in such a manner that a cell involved in the medical disorder no longer responds to extracellular stimuli (e.g., growth factors or cytokines), or the killing of a cell involved in the medical disorder through cellular apoptosis.

One aspect of the present invention involves the recognition that an MEKK protein of the present invention is capable of regulating the homeostasis of a cell by regulating cellular activity such as cell growth cell death, and cell function (e.g., secretion of cellular products). Such regulation, in most cases, is independent of Raf, however, as discussed above (and as shown in FIG. 2), some pathways capable of regulation by MEKK protein may be subject to upstream regulation by Raf protein. Therefore, it is within the scope of the present invention to either stimulate or inhibit the activity of Raf protein and/or MEKK protein to achieve desired regulatory results. Without being bound by theory, it is believed that the regulation of Raf protein and MEKK protein activity at the divergence point from Ras protein (see FIG. 2) can be controlled by a "2-hit" mechanism. For example, a first "hit" can comprise any means of stimulating Ras protein, thereby stimulating a Ras-dependent pathway, including, for example, contacting a cell with a growth factor which is capable of binding to a cell surface receptor in such a manner that Ras protein is activated. Following activation of Ras protein, a second "hit" can be delivered that is capable of increasing the activity of JNK activity compared with MAPK activity, or vice versa. A second "hit" can include, but is not limited to, regulation of JNK or MAPK activity by compounds capable of stimulating or inhibiting the activity of MEKK, JEK, Raf and/or MEK. For example, compounds such as protein kinase C or phospholipase C kinase, can provide the second "hit" needed to drive the divergent Ras-dependent pathway down the MEKK-dependent pathway in such a manner that JNK is preferentially activated over MAPK.

One embodiment of the present: invention comprises a method for regulating the homeostasis of a cell comprising regulating the activity of an MEKK-dependent pathway relative to the activity of a Raf-dependent pathway in the cell. As used herein, the term "homeostasis" refers to the tendency of a cell to maintain a normal state using intracellular systems such as signal transduction pathways. Regulation of the activity of an MEKK-dependent pathway includes increasing the activity of an MEKK-dependent pathway relative to the activity of a Raf-dependent pathway by regulating the activity of a member of an MEKK-dependent pathway, a member of a Raf-dependent pathway, and combinations thereof, to achieve desired regulation of phosphorylation along a given pathway, and thus effect apoptosis. Preferred regulated members of an MEKK-dependent pathway or a Raf-dependent pathway to regulate include, but are not limited to, proteins including MEKK, Ras, Raf, JEK, MEK, MAPK, JNK, TCF, ATF-2, Jun and Myc, and combinations thereof.

In one embodiment, the activity of a member of an MEKK-dependent pathway, a member of a Raf-dependent pathway, and combinations thereof, are regulated by altering the concentration of such members in a cell. One preferred regulation scheme involves altering the concentration of proteins including MEKK, Ras, Raf, JEK, MEK, MAPK, JNK, TCF, Jun, ATF-2, and Myc, and combinations thereof. A more preferred regulation scheme involves increasing the concentration of proteins including MEKK, Ras, JEK, JNK, Jun, ATF-2, and Myc, and combinations thereof. Another more preferred regulation scheme involves decreasing the concentration of proteins including Raf, MEK, MAPK, and TCF, and combinations thereof. It is also within the scope of the present invention that the regulation of protein concentrations in two or more of the foregoing regulation schemes can be combined to achieve an optimal apoptotic effect in a cell.

A preferred method for increasing the concentration of a protein in a regulation scheme of the present invention includes, but is not limited to, increasing the copy number of a nucleic acid sequence encoding such protein within a cell, improving the efficiency with which the nucleic acid sequence encoding such protein is transcribed within a cell, improving the efficiency with which a transcript is translated into such a protein, improving the efficiency of post-translational modification of such protein, contacting cells capable of producing such protein with anti-sense nucleic acid sequences, and combinations thereof.

In a preferred embodiment of the present invention, the homeostasis of a cell is controlled by regulating the apoptosis of a cell. A suitable method for regulating the apoptosis of a cell is to regulate the activity of an MEKK-dependent pathway in which the MEKK protein regulates the pathway substantially independent of Raf. A particularly preferred method for regulating the apoptosis of a cell comprises increasing the concentration of MEKK protein by contacting a cell with a nucleic acid molecule encoding an MEKK protein that possesses unregulated kinase activity. A preferred nucleic acid molecule with which to contact a cell includes a nucleic acid molecule encoding the MEKK protein shown in SEQ ID NO:1 and SEQ ID NO:2, and combinations thereof. A more preferred nucleic acid molecule with which to contact a cell includes a nucleic acid molecule encoding a truncated MEKK protein having only the kinase catalytic domain (i.e., no regulatory domain) of the MEKK protein shown in SEQ ID NO:1 and SEQ ID NO:2. An even more preferred nucleic acid molecule with which to contact a cell includes a nucleic acid molecule including MEKK6$_{358-626}$. Again, suitable variation of an MEKK protein described herein comprises a protein encoded by a nucleic acid molecule that are able to hybridize to any of the above sequences under stringent conditions.

It is within the scope of the invention that the foregoing method can further comprise the step of decreasing the activity of MEK protein in the cell by contacting the cell with a compound capable of inhibiting MEK activity. Such compounds can include: peptides capable of binding to the kinase domain of MEK in such a manner that phosphorylation of MAPK protein by the MEK protein is inhibited; and/or peptides capable of binding to a portion of a MAPK protein in such a manner that phosphorylation of the MAPK protein is inhibited.

In another embodiment, the activity of a member of an MEKK-dependent pathway, a member of a Raf-dependent pathway, and combinations thereof, can be regulated by directly altering the activity of such members in a cell. A preferred method for altering the activity of a member of an MEKK-dependent pathway, includes, but is not limited to, contacting a cell with a compound capable of directly interacting with a protein including MEKK, Ras, JEK, JNK, Jun, ATF-2, and Myc, and combinations thereof, in such a manner that the proteins are activated; and/or contacting a cell with a compound capable of directly interacting with a protein including Raf, MEK, MAPK, TCF protein, and combinations thereof in such a manner that the activity of the proteins are inhibited. A preferred compound with which to contact a cell that is capable of regulating a member of an MEKK-dependent pathway includes a peptide capable of binding to the regulatory domain of proteins including MEKK, Ras, JEK, JNK, Jun, ATF-2, and Myc, in which the peptide inhibits the ability of the regulatory domain to regulate the activity of the kinase domains of such proteins. Another preferred compound with which to contact a cell includes TNFα, growth factors regulating tyrosine kinases, hormones regulating G protein-coupled receptors and FAS ligand.

A preferred compound with which to contact a cell that is capable of regulating a member of a Raf-dependent pathway includes a peptide capable of binding to the kinase catalytic domain of a protein selected from the group consisting of Raf, MEK-1, MEK-2, MAPK, and TCF, in which the peptide inhibits the ability of the protein to be phosphorylated or to phosphorylate a substrate.

In accordance with the present invention, a compound can regulate the activity of a member of an MEKK-dependent pathway by affecting the ability of one member of the pathway to bind to another member of the pathway. Inhibition of binding can be achieved by directly interfering at the binding site of either member, or altering the conformational structure, thereby precluding the binding between one member and another member.

Another preferred compound with which to contact a cell that is capable of regulating a member of an MEKK-dependent pathway includes an isolated compound that is capable of regulating the binding of MEKK protein to Ras protein (referred to herein as a Ras:MEKK binding compound). In one embodiment, a Ras:MEKK binding compound of the present invention comprises an isolated peptide (or mimetope thereof) comprising an amino acid sequence derived from a Ras protein. In another embodiment, a Ras:MEKK binding compound of the present invention comprises an isolated peptide (or mimetope thereof) comprising an amino acid sequence derived from an MEKK protein. According to the present invention, an isolated, or biologically pure, peptide, is a peptide that has been removed from its natural milieu. As such, "isolated" and "biologically pure" do not necessarily reflect the extent to which the protein has been purified. An isolated compound of the present invention can be obtained from a natural source or produced using recombinant DNA technology or chemical synthesis. As used herein, an isolated peptide can be a full-length protein or any homolog of such a protein in which amino acids have been deleted (e.g., a truncated version of the protein), inserted, inverted, substituted and/or derivatized (e.g., by glycosylation, phosphorylation, acetylation, myristylation, prenylation, palmitilation, and/or amidation) such that the peptide is capable of regulating the binding of Ras protein to MEKK protein.

In accordance with the present invention, a "mimetope" refers to any compound that is able to mimic the ability of an isolated compound of the present invention. A mimetope can be a peptide that has been modified to decrease its susceptibility to degradation but that still retain regulatory activity. Other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds as disclosed herein that are capable of inhibiting the binding of Ras to MEKK. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

In one embodiment, a Ras:MEKK binding compound of the present invention comprises an isolated peptide having a domain of a Ras protein that is capable of binding to an MEKK protein (i.e., that has an amino acid sequence which enable the peptide to be bound by an MEKK protein). A Ras peptide of the present invention is of a size that enables the peptide to be bound by an MEKK protein, preferably, at least about 4 amino acid residues, more preferably at least about 12 amino acid residues, and even more preferably at least about 25 amino acid residues. In particular, a Ras peptide of the present invention is capable of being bound by the COOH-terminal region of MEKK, preferably the region of MEKK containing the MEKK kinase domain. Preferably, a Ras peptide of the present invention comprises the effector domain of Ras and more preferably amino acid residues 17–42 of H-Ras.

In another embodiment, a Ras:MEKK binding compound of the present invention comprises an isolated MEKK peptide that has a domain of an MEKK protein that is capable of binding to a Ras protein (i.e., that has an amino acid sequence which enables the peptide to be bound by a Ras protein). An MEKK peptide of the present invention is of a size that enables the peptide to be bound by a Ras protein, in particular by the effector domain of a Ras protein. Preferably, an MEKK peptide of the present invention at least about 320 amino acids in length. Preferably, an MEKK peptide of the present invention comprises the COOH-terminal region of an MEKK protein and more preferably $MEKK_{COOH}$ (as described in detail in Example 21).

Ras is a critical component of tyrosine kinase growth factor receptor and G-protein coupled receptor regulation of signal transduction pathways controlling mitogenesis and differentiation. According to the present invention, the protein serine-threonine kinases Raf-1 and MEKK1 are Ras effectors and selectively bind to Ras in a GTP dependent manner. The p110 catalytic subunit of the lipid kinase has also been shown to directly interact with Ras in a GTP dependent manner. Ras-GAP and neurofibromin also regulate Ras GTPase activity. Raf-1, MEKK1 and PI3-kinase are capable of increasing the activity in cells expressing GTPase-deficient Ras consistent with their interaction with Ras-GTP being involved in their regulation.

Different functional domains of Ras effectors bind to Ras in a GTP dependent manner. The Ras binding domain for Raf-1 is encoded in the extreme $NH_2$-terminal regulatory domain of Raf-1. The Ras binding domain is encoded within the catalytic domain of MEKK1. Both Raf-1 and MEKK1 binding to Ras is blocked by a Ras effector domain peptide. Thus, Raf-1, MEKK1 and other Ras effectors can compete for interaction with Ras-GTP presumably at the Ras effector domain. The relative abundance and affinity of each Ras effector in different cells may influence the magnitude, onset and duration of each effector response. Secondary inputs, such as phosphorylation of the different Ras effectors, can also influence their interaction with Ras-GTP. The kinetic properties of Ras effector activation in cells relative to effector affinity for Ras-GTP are predictable based on the foregoing information. For example, MEKK1 can preferentially regulate the SEK/Jun kinase pathways relative to MAPK. Activation of the SEK/Jun kinase pathway is generally slower in onset and maintained as maximal activity longer than the activation of MAPK. As additional MEKKs are characterized it will be important to characterize their regulation and interaction with Ras-GTP. Undoubtedly additional Ras effectors will be identified in the near future.

The present invention also includes a method to administer isolated compounds of the present invention to a cell to regulate signal transduction activity in the cell. In particular, the present invention includes a method to administer an isolated compound of the present invention to a cell to regulate apoptosis of the cell.

The present invention also includes a method for regulating the homeostasis of a cell comprising injecting an area of a subject's body with an effective amount of a naked plasmid DNA compound (such as is taught, for example in Wolff et al., 1990, *Science* 247, 1465–1468). A naked plasmid DNA compound comprises a nucleic acid molecule encoding an MEKK protein of the present invention, operatively linked to a naked plasmid DNA vector capable of being taken up by and expressed in a recipient cell located in the body area. A preferred naked plasmid DNA compound of the present invention comprises a nucleic acid molecule encoding a truncated MEKK protein having deregulated kinase activity. Preferred naked plasmid DNA vectors of the present invention include those known in the art. When administered to a subject, a naked plasmid DNA compound of the present invention transforms cells within the subject and directs the production of at least a portion of an MEKK protein or RNA nucleic acid molecule that is capable of regulating the apoptosis of the cell.

A naked plasmid DNA compound of the present invention is capable of treating a subject suffering from a medical disorder including cancer, autoimmune disease, inflammatory responses, allergic responses and neuronal disorders, such as Parkinson's disease and Alzheimer's disease. For example, a naked plasmid DNA compound can be administered as an anti-tumor therapy by injecting an effective amount of the plasmid directly into a tumor so that the plasmid is taken up and expressed by a tumor cell, thereby killing the tumor cell. As used herein, an effective amount of a naked plasmid DNA to administer to a subject comprises an amount needed to regulate or cure a medical disorder the naked plasmid DNA is intended to treat, such mode of administration, number of doses and frequency of dose capable of being decided upon, in any given situation, by one of skill in the art without resorting to undue experimentation.

One aspect of the present invention relates to the recognition that an MEKK protein is capable of activating MAPK and that MAPK can regulate various cellular functions as disclosed in U.S. Pat. No. 5,405,941, which is incorporated herein by this reference.

An isolated compound of the present invention can be used to formulate a therapeutic composition. In one embodiment, a therapeutic composition of the present invention includes at least one isolated peptide of the present invention. A therapeutic composition of the present invention can further comprise suitable excipients. A therapeutic composition of the present invention can be formulated in an excipient that the subject to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful excipients include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic composition can also comprise a carrier. Carriers are typically compounds that increase the half-life of a therapeutic composition in the treated animal. Suitable carriers include, but are not limited to, liposomes, micelles, cells, polymeric controlled release formulations, biodegradable implants, bacteria, viruses, oils, esters, and glycols. Preferred carriers include liposomes and micelles.

A therapeutic composition of the present invention can be administered to any subject having a medical disorder as herein described. Acceptable protocols by which to administer therapeutic compounds of the present invention in an effective manner can vary according to individual dose size, number of doses, frequency of dose administration, and mode of administration. Determination of such protocols can be accomplished by those skilled in the art without resorting to undue experimentation. An effective dose refers to a dose capable of treating a subject for a medical disorder as described herein. Effective doses can vary depending upon, for example, the therapeutic composition used, the medical disorder being treated, and the size and type of the recipient animal. Effective doses to treat a subject include doses administered over time that are capable of regulating the activity, including growth, of cells involved in a medical disorder. For example, a first dose of a naked plasmid DNA compound of the present invention can comprise an amount of that causes a tumor to decrease in size by about 10% over 7 days when administered to a subject having a tumor. A second dose can comprise at least the same the same therapeutic compound than the first dose.

Another aspect of the present invention includes a method for prescribing treatment for subjects having a medical disorder as described herein. A preferred method for prescribing treatment comprises: (a) measuring the MEKK protein activity in a cell involved in the medical disorder to determine if the cell is susceptible to treatment using a method of the present invention; and (b) prescribing treatment comprising regulating the activity of an MEKK-dependent pathway relative to the activity of a Raf-dependent pathway in the cell to induce the apoptosis of the cell. The step of measuring MEKK protein activity can comprise: (1) removing a sample of cells from a subject; (2) stimulating the cells with a TNFα; and (3) detecting the state of phosphorylation of JEK protein using an immunoassay using antibodies specific for phosphothreonine and/or phosphoserine.

The present invention also includes antibodies capable of selectively binding to an MEKK protein of the present invention. Such an antibody is herein referred to as an anti-MEKK antibody. Polyclonal populations of anti-MEKK antibodies can be contained in an MEKK antiserum. MEKK antiserum can refer to affinity purified polyclonal antibodies, ammonium sulfate cut antiserum or whole antiserum. As used herein, the term "selectively binds to" refers to the ability of such an antibody to preferentially bind to MEKK proteins. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., Molecular Cloning: A Laboratory Manual, Cold Spring Harbor Labs Press, 1989.

Antibodies of the present invention can be either polyclonal or monoclonal antibodies and can be prepared using techniques standard in the art. Antibodies of the present invention include functional equivalents such as antibody fragments and genetically-engineered antibodies, including single chain antibodies, that are capable of selectively binding to at least one of the epitopes of the protein used to obtain the antibodies. Preferably, antibodies are raised in response to proteins that are encoded, at least in part, by a MEKK nucleic acid molecule. More preferably antibodies are raised in response to at least a portion of an MEKK protein, and even more preferably antibodies are raised in response to either the amino terminus or the carboxyl terminus of an MEKK protein. Preferably, an antibody of the present invention has a single site binding affinity of from about $10^3 M^{-1}$ to about $10^{12} M^{-1}$ for an MEKK protein of the present invention.

A preferred method to produce antibodies of the present invention includes administering to an animal an effective amount of an MEKK protein to produce the antibody and recovering the antibodies. Antibodies of the present invention have a variety of potential uses that are within the scope of the present invention. For example, such antibodies can be used to identify unique MEKK proteins and recover MEKK proteins.

Another aspect of the present invention comprises a therapeutic compound capable of regulating the activity of an MEKK-dependent pathway in a cell identified by a process, comprising: (a) contacting a cell with a putative regulatory molecule; and (b) determining the ability of the putative regulatory compound to regulate the activity of an MEKK-dependent pathway in the cell by measuring the activation of at least one member of said MEKK-dependent pathway. Preferred methods to measure the activation of a member of an MEKK-dependent pathway include measuring the transcription regulation activity of c-Myc protein, measuring the phosphorylation of a protein selected from the group consisting of MEKK, JEK, JNK, Jun, ATF-2, Myc, and combinations thereof.

Mitogen-activated protein kinase kinase (MEKK1) is a serine/threonine protein kinase that functions parallel to Raf-1 in the regulation of sequential protein kinase pathways that involve both mitogen-activated and stress-activated protein kinases. In this study, we examined the interaction of MEKK1 with 14-3-3 proteins. The T cell 14-3-3 isoform, but not the β and stratifin isoforms, interacted with MEKK1 in the two-hybrid system. We also prepared GST fusion proteins of the T cell, β, and stratifin 14-3-3 isoforms to further characterize the domains of MEKK1 and Raf-1 that interact with these proteins. We demonstrate that the T cell and β 14-3-3 isoform, but not stratifin, interact with COS cell-expressed MEKK1. Furthermore, the amino-terminal moiety, but not the carboxyl-terminal moiety, of expressed MEKK1 interacts with the GST•14-3-3 although the interaction is best when holoMEKK1 is expressed. In contrast, GST•14-3-3 proteins interact with both the amino- and carboxyl-regions of COS cell-expressed Raf-1 protein. Thus, although MEKK1 and Raf-1 function at a parallel point in the sequential protein kinase pathways, the interaction of 14-3-3 proteins with these kinases is not identical, suggesting a differential regulation between Raf-1 and MEKK1-stimulated pathways.

The following examples are provided for the purposes of illustration and are not intended to limit the scope of the present invention.

EXAMPLES

Example 1

This example describes the structural characterization of MEKK1 protein.

A. MEKK1 Nucleotide Sequence

MEKK1 protein was cloned by the following method. Unique degenerate inosine oligodeoxynucleotides were designed to correspond to regions of sequence identity between the yeast Ste11 and Byr2 genes. With primers and cDNA templates derived from polyadenylated RNA from NIH 3T3 cells, a polymerase chain reaction (PCR) amplification product of 320 base pairs (bp) was isolated. This 320 bp cDNA was used as a probe to identify an MEKK1 cDNA of 3260 bp from a mouse brain cDNA library using standard methods in the art. The MEKK1 nucleotide sequence was determined by dideoxynucleotide sequencing of double-stranded DNA using standard methods in the art.

Referring to Table 1, based on the Kozak consensus sequence for initiation codons, the starting methionine can be predicted to occur at nucleotide 486.

TABLE 1

|  |  |  |  |  |  |  |  |  |  |  |  |  |  |  |  |  |  |  |
|---|---|---|---|---|---|---|---|---|---|---|---|---|---|---|---|---|---|---|
|  | Met | Val | Thr | Ala | Val | Pro | Ala | Val | Phe | Ser | Lys | Leu | Val | Thr | Met | Leu |  | MEKK1 |
| Asn | Ala | Ser | Gly | Ser | Thr | His | Phe | Thr | Arg | Met | Arg | Arg | Arg | Leu | Met | Ala | Ile | MEKK1 |
|  |  |  |  |  |  |  |  |  |  |  |  |  |  | Met | Asp | Asp | Gln | MEKK2 |
|  |  |  |  |  |  |  |  |  |  |  |  |  |  | Met | Asp | Glu | Gln | MEKK3 |
| Ala | Asp | Glu | Val | Glu | Ile | Ala | Glu | Val | Ile | Gln | Leu | Gly | Val | Glu | Asp | Thr | Val | 1 |
| Gln | Ala | Leu | Asn | Ser | Ile | Met | Gln | Asp | Ile | — | — | — | — | — | — | — | — | 2 |
| Glu | Ala | Leu | Asp | Ser | Ile | Met | Lys | Asp | Leu | Val | Ala | Leu | Gln | Met | Ser | Arg | Arg | 3 |
| Asp | Gly | His | Gln | Asp | Ser | Leu | — | Ala | Val | Ala | Pro | Thr | Ser | Cys | Leu | Glu | Asn | 1 |
| — | — | — | — | — | — | — | — | Ala | Val | Leu | His | Lys | Pro | Val | Gly | Gln | His | 2 |
| Thr | Arg | Leu | — | — | — | — | — | Ser | — | — | Gly | Tyr | Glu | Thr | Met | Lys | Asn | 3 |
| Ser | Ser | Leu | Glu | His | Thr | Val | His | Arg | Glu | Lys | Thr | Gly | Lys | Gly | Leu | Ser | Ala | 1 |
| Tyr | Leu | Tyr | Lys | Lys | Pro | Gly | Lys | Arg | Met | Gln | Asn | Leu | His | His | Gln | Lys | Asn | 2 |
| Lys | Asp | Thr | Gly | His | Pro | Asn | Arg | Gln | Ser | Asp | Val | Arg | Ile | Lys | Phe | Glu | His | 3 |
| Thr | Arg | Leu | Ser | Ala | Ser | Ser | Glu | Asp | Ile | Ser | Asp | Arg | Leu | Ala | Gly | Val | Ser | 1 |
| Met | Phe | Glu | Ser | Asn | Leu | Asn | Ile | Glu | Glu | Glu | Lys | Arg | Ile | Leu | Gln | Val | Thr | 2 |
| Asn | Gly | Glu | Arg | Arg | Ile | — | Ile | Ala | Phe | Ser | Arg | Pro | Val | Arg | Tyr | Glu | Asp | 3 |
| Val | Gly | Leu | Pro | Ser | Ser | Thr | Thr | Thr | Glu | Gln | Pro | Lys | Pro | Ala | Val | Gln | Thr | 1 |
| Arg | Pro | Val | Lys | Leu | Glu | Asp | Leu | Arg | Ser | Lys | Ser | Lys | Ile | Ala | Phe | Gly | Gln | 2 |
| Val | Glu | His | Lys | Val | Thr | Thr | Val | Phe | Gly | Gln | Pro | Leu | Asp | Leu | His | Tyr | Met | 3 |
| Lys | Gly | Arg | Pro | His | Ser | Gln | Cys | Leu | Asn | Ser | Ser | — | Pro | Leu | Ser | His | Ala | 1 |
| Ser | Met | Asp | Leu | His | Tyr | Thr | Asn | Asn | Glu | Leu | Val | Ile | Pro | Leu | Thr | Thr | Gln | 2 |
| Asn | Asn | Glu | Leu | Ser | Ile | Leu | Leu | Lys | Asn | Gln | Asp | Asp | Leu | Asp | Lys | Ala | Ile | 3 |
| Gln | Leu | Met | Phe | Pro | Ala | Pro | Ser | Ser | Ala | Cys | Ser | Ala | Pro | Ser | Ser | Val | Pro | 1 |
| Asp | Asp | Leu | Asp | Lys | Ala | Val | Glu | Leu | Leu | Asp | Arg | Ser | Ile | His | Met | Lys | Ser | 2 |
| Asp | Ile | Leu | Asp | Arg | Ser | Ser | Ser | Met | Lys | Ser | Leu | Arg | Ile | Leu | Leu | Leu | Ser | 3 |
| Asp | Ile | Ser | Lys | His | Arg | Pro | Gln | Ala | Phe | Val | Pro | Cys | Lys | Ile | Pro | Ser | Ala | 1 |
| Leu | — | Lys | Ile | Leu | Leu | Val | Val | Asn | Gly | Ser | Thr | Val | Ala | — | Thr | Asn | Leu | 2 |
| Gln | Asp | Arg | Asn | His | Thr | Ser | Ser | Ser | Pro | His | Ser | Gly | Val | Ser | Arg | Gln | Val | 3 |
| Ser | Pro | Gln | Thr | Gln | Arg | Lys | Phe | Ser | Leu | Gln | Phe | Gln | Arg | Asn | Cys | Ser | Glu | 1 |
| Glu | Pro | Ser | Pro | Ser | Pro | Glu | Asp | Leu | Asn | Asn | Thr | Pro | Leu | Gly | Ala | Glu | Arg | 2 |
| Arg | Ile | Glu | Lys | Pro | Ser | Gln | Ser | Ala | Gly | Ser | Asn | Thr | Ile | Tyr | Gln | Ala | Pro | 3 |
| His | Arg | Asp | Ser | Asp | Gln | Leu | Ser | Pro | Val | Phe | Thr | Gln | Ser | — | Arg | Pro | Pro | 1 |
| Lys | Lys | Arg | Leu | Ser | Val | Val | Gly | Pro | Pro | Asn | Arg | — | — | Asp | Arg | Ser | Ser | 2 |
| Glu | Pro | Arg | Ser | Arg | His | Leu | Ser | Val | Ser | Ser | Gln | Asn | Pro | Gly | Arg | Ser | Ser | 3 |
| Pro | Ser | Ser | Asn | Ile | His | Arg | Pro | Lys | Pro | Val | Pro | Ser | Pro | Gly | Ser | Thr | Thr | 1 |
| Pro | Pro | Pro | Gly | Tyr | Ile | Pro | Asp | Ile | Leu | His | Gln | Ile | Ala | Pro | Arg | Asn | Gly | Ser | 2 |
| Pro | Pro | Pro | Gly | Tyr | Val | Pro | Glu | Arg | Gln | Gln | His | Ile | Ala | Arg | Gln | Gly | Ser | 3 |
| Ser | Lys | Leu | Gly | Asp | Ala | Thr | Lys | Ser | Ser | Met | Thr | Leu | Asp | Leu | Gly | Ser | Ala | 1 |
| Phe | Thr | Ser | Ile | Asn | Ser | Glu | Gly | Glu | Phe | Ile | Pro | Glu | Ser | Met | Asp | Gln | — | 2 |
| Phe | Thr | Ser | Ile | Asn | Ser | Glu | Gly | Glu | Phe | Ile | Pro | Glu | Thr | Ser | Glu | Gln | Cys | 3 |
| Ser | Arg | Cys | Asp | Asp | Ser | Phe | Gly | Gly | Gly | Asn | Ser | Gly | Asn | Ala | Val | Ile | 1 |
| Met | Leu | Asp | Pro | Leu | Ser | Leu | Ser | Ser | Pro | Glu | Asn | Ser | Gly | Ser | Gly | Ser | Cys | 2 |
| Met | Leu | Asp | Pro | Leu | Ser | Ser | Ala | Glu | Asn | Ser | Leu | Ser | Gly | Ser | Cys | Gln | Ser | 3 |
| Pro | Ser | Asp | Glu | Thr | Val | Phe | Thr | Pro | Val | Glu | Asp | Lys | Cys | Arg | Leu | Asp | Val | 1 |
| Pro | Ser | Leu | Asp | Ser | Pro | Leu | Asp | Gly | Glu | Ser | Tyr | Pro | Lys | Ser | Arg | Met | Pro | 2 |
| Leu | Asp | Arg | Ser | Ala | Asp | Ser | Pro | Ser | Phe | Arg | Lys | Ser | Gln | Met | Ser | Arg | Ala | 3 |
| Asn | Thr | Glu | Leu | Asn | Ser | Ser | Ile | Glu | Asp | Leu | Leu | Glu | Ala | Ser | Met | Pro | Ser | 1 |
| Arg | Ala | Gln | Ser | Tyr | Pro | Asp | Asn | His | Gln | Phe | Thr | Asp | Tyr | Asp | Asn | Pro | 2 |
| Arg | Ser | Phe | Pro | Asp | Asn | Arg | — | — | — | Glu | Cys | Ser | Asp | Lys | — | — | — | 3 |
| Ser | Asp | Thr | Thr | Val | Thr | Phe | Lys | Ser | Glu | Val | Ala | Val | Leu | Ser | Pro | Glu | Lys | 1 |
| Ile | Phe | Glu | Lys | Phe | Gly | Lys | Gly | Gly | Thr | Tyr | Pro | Arg | Arg | Tyr | His | Val | Ser | 2 |
| — | Arg | Glu | Gln | Leu | Tyr | Asp | Lys | Gly | Val | Gly | Gly | Thr | Tyr | Pro | Arg | 3 |
| Ala | Glu | Asn | Asp | Asp | Thr | Tyr | Lys | Asp | Asp | Val | Asn | His | Asn | Gln | Lys | Cys | Lys | 1 |
| Tyr | His | His | Gln | Glu | Tyr | Asn | Asp | Gly | Arg | Lys | Thr | Phe | Pro | Arg | Ala | Arg | Arg | 2 |
| Arg | Tyr | His | Val | Ser | Val | His | His | Lys | Asp | Tyr | Asn | Asp | Gly | Arg | Arg | Thr | Phe | 3 |
| Glu | Lys | Met | Glu | Ala | Glu | Glu | Glu | Ala | Leu | Ala | Ile | Ala | Met | Ala | Met | Ser | 1 |
| Thr | Gln | Gly | Thr | Ser | Phe | Arg | Gly | Ser | Pro | Val | Pro | Thr | Asp | His | Ser | Ser | 2 |
| Pro | Arg | Ile | Arg | Arg | His | Gln | Gly | Asn | Leu | Phe | Thr | Leu | Val | Pro | Ser | Ser | Arg | 3 |
| Ala | Ser | Gln | Asp | Ala | Leu | Pro | Ile | Val | Pro | Gln | Leu | Gln | Val | Glu | Asn | Gly | Glu | 1 |
| Leu | Ser | Thr | Ser | Ser | Gly | Ser | Ser | Val | Phe | Thr | Pro | Glu | Tyr | Asp | Asp | Ser | Arg | 2 |
| Ser | Leu | Ser | Thr | Asn | Gly | Glu | Asn | Met | Gly | Val | Ala | Val | Gln | Tyr | Leu | Asp | Pro | 3 |
| Asp | Ile | Ile | Ile | Ile | Gln | Gln | Asp | Thr | Pro | Glu | Thr | Leu | Pro | Gly | His | Thr | Lys | 1 |
| Ile | Arg | Arg | Arg | Gly | Ser | Asp | Ile | Asp | Asn | Pro | Thr | Leu | Thr | Val | Thr | Asp | Ile | 2 |
| Arg | Gly | Arg | Leu | Arg | Ser | Ala | Asp | Ser | Glu | Asn | Ala | Leu | Thr | Val | Gln | Glu | Arg | 3 |

TABLE 1-continued

| | | | | | | | | | | | | | | | | | | |
|---|---|---|---|---|---|---|---|---|---|---|---|---|---|---|---|---|---|---|
| Ala | Lys | Gln | Pro | Tyr | Arg | Glu | *Asp* | *Ala* | *Glu* | *Trp* | *Leu* | *Lys* | *Gly* | *Gln* | *Gln* | *Ile* | *Gly* | 1 |
| Ser | Pro | Pro | Ser | Arg | Ser | Pro | Arg | Ala | Pro | Thr | Asn | Trp | Arg | Leu | Gly | Lys | Leu | 2 |
| Asn | Val | Pro | Thr | Lys | Ser | Pro | Ser | Ala | Pro | Ile | Asn | Trp | Arg | Arg | Gly | Lys | Leu | 3 |
| *Leu* | *Gly* | *Ala* | *Phe* | *Ser* | *Ser* | *Cys* | *Tyr* | *Gln* | *Ala* | *Gln* | *Asp* | *Val* | *Gly* | *Thr* | *Gly* | *Thr* | *Leu* | 1 |
| Leu | Gly | Gln | Gly | Ala | Phe | Gly | Arg | Val | Tyr | Leu | Cys | Tyr | Asp | Val | Asp | Thr | Gly | 2 |
| Leu | Gly | Gln | Gly | Ala | Phe | Gly | Arg | Val | Tyr | Leu | Cys | Tyr | Asp | Val | Asp | Thr | Gly | 3 |
| *Met* | *Ala* | *Val* | *Lys* | *Gln* | *Val* | *Thr* | *Tyr* | *Val* | *Arg* | *Asn* | *Thr* | *Ser* | *Glu* | *Gln* | *Glu* | *Glu* | *Glu* | 1 |
| Arg | Glu | Leu | Ala | Val | Lys | Gln | Val | Gln | Phe | Asn | Pro | Glu | Ser | Pro | Glu | Thr | Ser | 2 |
| Arg | Glu | Leu | Ala | Ser | Lys | Gln | Val | Gln | Phe | Asp | Pro | Asp | Ser | Pro | Glu | Thr | Ser | 3 |
| *Val* | *Val* | *Glu* | *Ala* | *Leu* | *Arg* | *Glu* | *Glu* | *Ile* | *Arg* | *Met* | *Met* | *Gly* | *His* | *Leu* | *Asn* | *His* | *Pro* | 1 |
| Lys | Glu | Val | Asn | Ala | Leu | Glu | Cys | Glu | Ile | Gln | Leu | Leu | Lys | Asn | Leu | Leu | His | 2 |
| Lys | Glu | Val | Ser | Ala | Leu | Glu | Cys | Glu | Ile | Gln | Leu | Leu | Lys | Asn | Leu | Gln | His | 3 |
| *Asn* | *Ile* | *Ile* | *Arg* | *Met* | *Leu* | *Gly* | *Ala* | *Thr* | *Cys* | *Glu* | *Lys* | *Ser* | *Asn* | *Tyr* | *Asn* | *Leu* | *Phe* | 1 |
| Glu | Arg | Ile | Val | Gln | Tyr | Tyr | Gly | Cys | Leu | Arg | Asp | Pro | Gln | Glu | Lys | Thr | Leu | 2 |
| Glu | Arg | Ile | Val | Gln | Tyr | Tyr | Gly | Cys | Leu | Arg | Asp | Pro | Gln | Glu | Lys | Ile | Leu | 3 |
| *Ile* | *Glu* | *Trp* | *Met* | *Ala* | *Gly* | *Gly* | *Ser* | *Val* | *Ala* | *His* | *Leu* | *Leu* | *Ser* | *Lys* | *Tyr* | *Gly* | *Ala* | 1 |
| Ser | Ile | Phe | Met | Glu | Leu | Ser | Pro | Gly | Gly | Ser | Ile | Lys | Asp | Gln | Leu | Lys | Ala | 2 |
| Thr | Ile | Phe | Met | Glu | Tyr | Met | Pro | Gly | Gly | Ser | Val | Lys | Asp | Gln | Leu | Lys | Ala | 3 |
| *Phe* | *Lys* | *Glu* | *Ser* | *Val* | *Val* | *Ile* | *Asn* | *Tyr* | *Thr* | *Glu* | *Gln* | *Leu* | *Leu* | *Arg* | *Gly* | *Leu* | *Ser* | 1 |
| Tyr | Gly | Ala | Leu | Thr | Glu | Asn | Val | Thr | Arg | Lys | Tyr | Thr | Arg | Gln | Ile | Leu | Glu | 2 |
| Tyr | Gly | Ala | Leu | Thr | Glu | Ser | Val | Thr | Arg | Lys | Tyr | Thr | Arg | Gln | Ile | Leu | Glu | 3 |
| *Tyr* | *Leu* | *His* | *Glu* | *Asn* | — | — | *Gln* | — | *Ile* | *Ile* | *His* | *Arg* | *Asp* | *Val* | *Lys* | *Gly* | *Ala* | 1 |
| Gly | Val | His | Tyr | Leu | His | Ser | Asn | Met | Ile | Val | His | Arg | Asp | Ile | Lys | Gly | Ala | 2 |
| Gly | Met | Ser | Tyr | Leu | His | Ser | Asn | Met | Ile | Val | His | Arg | Asp | Ile | Lys | Gly | Ala | 3 |
| *Asn* | *Leu* | *Leu* | *Ile* | *Asp* | *Ser* | *Thr* | *Gly* | *Gln* | — | *Arg* | *Leu* | *Arg* | *Ile* | *Ala* | *Asp* | *Phe* | *Gly* | 1 |
| Asn | Ile | Leu | Arg | Asp | Ser | Thr | Gly | Asn | Ile | Lys | Leu | Gly | Asp | Phe | Gly | Ala | Ser | 2 |
| Asn | Ile | Leu | Arg | Asp | Ser | Ala | Gly | Asn | Val | Lys | Leu | Gly | Asp | Phe | Gly | Ala | Ser | 3 |
| *Ala* | *Ala* | *Ala* | *Arg* | *Leu* | *Ala* | *Ser* | *Lys* | — | *Gly* | *Thr* | *Gly* | *Gln* | *Phe* | *Gln* | *Gly* | *Gln* | *Gly* | 1 |
| Lys | Arg | Leu | Gln | Thr | Ile | Cys | Leu | Ser | Gly | Thr | Gly | Met | Lys | Ser | Val | Thr | Gly | 2 |
| Lys | Arg | Leu | Gln | Thr | Ile | Cys | Met | Ser | Gly | Thr | Gly | Ile | Arg | Ser | Val | Thr | Gly | 3 |
| *Gln* | *Leu* | *Leu* | *Gly* | *Thr* | *Ile* | *Ala* | *Phe* | *Met* | *Ala* | *Pro* | *Glu* | *Val* | *Leu* | *Arg* | *Gly* | *Gln* | *Gln* | 1 |
| — | Pro | Tyr | — | — | — | — | Trp | Met | Ser | Pro | Glu | Val | Ile | Ser | Gly | Glu | Gly | 2 |
| Thr | Pro | Tyr | — | — | — | — | Trp | Met | Ser | Pro | Glu | Val | Ile | Ser | Gly | Glu | Gly | 3 |
| *Tyr* | *Gly* | *Arg* | *Ser* | *Cys* | *Asp* | *Val* | *Trp* | *Ser* | *Val* | *Gly* | *Cys* | *Ala* | *Ile* | *Ile* | *Glu* | *Met* | *Ala* | 1 |
| Tyr | Gly | Arg | Lys | Ala | Asp | Ile | Trp | Ser | Val | Ala | Cys | Thr | Val | Val | Glu | Met | Leu | 2 |
| Tyr | Gly | Arg | Lys | Ala | Asp | Val | Trp | Ser | Leu | Gly | Cys | Thr | Val | Val | Glu | Met | Leu | 3 |
| *Cys* | *Ala* | *Lys* | *Pro* | *Pro* | *Trp* | *Asn* | *Ala* | *Glu* | *Lys* | *His* | *Ser* | *Asn* | *His* | *Leu* | *Ala* | *Leu* | *Ile* | 1 |
| Thr | Glu | Lys | Pro | Pro | Trp | — | Ala | Glu | Phe | Glu | Ala | — | Met | Ala | Ala | — | Ile | 2 |
| Thr | Glu | Lys | Pro | Pro | Trp | — | Ala | Glu | Tyr | Glu | Ala | — | Met | Ala | Ala | — | Ile | 3 |
| *Phe* | *Lys* | *Ile* | *Ala* | *Ser* | *Ala* | *Thr* | *Thr* | *Ala* | *Pro* | *Ser* | *Ile* | *Pro* | *Ser* | *His* | *Leu* | *Ser* | *Pro* | 1 |
| Phe | Lys | Ile | Ala | Thr | Gln | Pro | Thr | Asn | Pro | Lys | Leu | Pro | Pro | His | Val | Ser | Asp | 2 |
| Phe | Lys | Ile | Ala | Thr | Gln | Pro | Thr | Asn | Pro | Gln | Leu | Pro | Ser | His | Ile | Ser | Glu | 3 |
| *Gly* | *Leu* | *Arg* | *Asp* | *Val* | *Ala* | *Val* | *Arg* | *Cys* | *Leu* | *Glu* | *Leu* | *Gln* | *Pro* | *Gln* | *Asp* | *Arg* | *Pro* | 1 |
| Tyr | Thr | Arg | Asp | Phe | Leu | Lys | Arg | Ile | Phe | Val | Glu | Ala | Lys | Leu | — | Arg | Pro | 2 |
| His | Gly | Arg | Asp | Phe | Leu | Arg | Arg | Ile | Phe | Val | Glu | Ala | Arg | Gln | — | Arg | Pro | 3 |
| *Pro* | *Ser* | *Arg* | *Glu* | — | *Leu* | *Leu* | *Lys* | *His* | *Pro* | *Val* | *Phe* | *Arg* | *Thr* | *Thr* | *Trp* | | | 1 |
| — | Ser | Ala | Glu | Glu | Leu | Leu | Arg | His | Met | Phe | Val | His | Tyr | His | | | | 2 |
| — | Ser | Ala | Glu | Glu | Leu | Leu | Thr | His | His | Phe | Ala | Gln | Leu | Val | Tyr | | | 3 |

Bold Amino Terminus - Regulatory Domain
Underline sequence - Regulatory hinge Sequence
Bold Italics - Catalytic Domain With this methionine at the start, the cDNA encodes a protein of 672 amino acids, corresponding to a molecular size of 73 kD. There is another in-frame methionine at position 441, which does not follow the Kozak rule, but would yield a protein of 687 amino acid residues (74.6 kD). Also referring to Table 1, 20% of the NH$_2$-terminal 400 amino acids are serine or threonine and there are only two tyrosines. Several potential sites of phosphorylation by protein kinase C are apparent in the NH$_2$-terminal region. The kinase catalytic domain is located in the COOH-terminal half of the MEKK1.

B. Southern Blot Analysis of MEKK1 Transcript

Figure 3A:
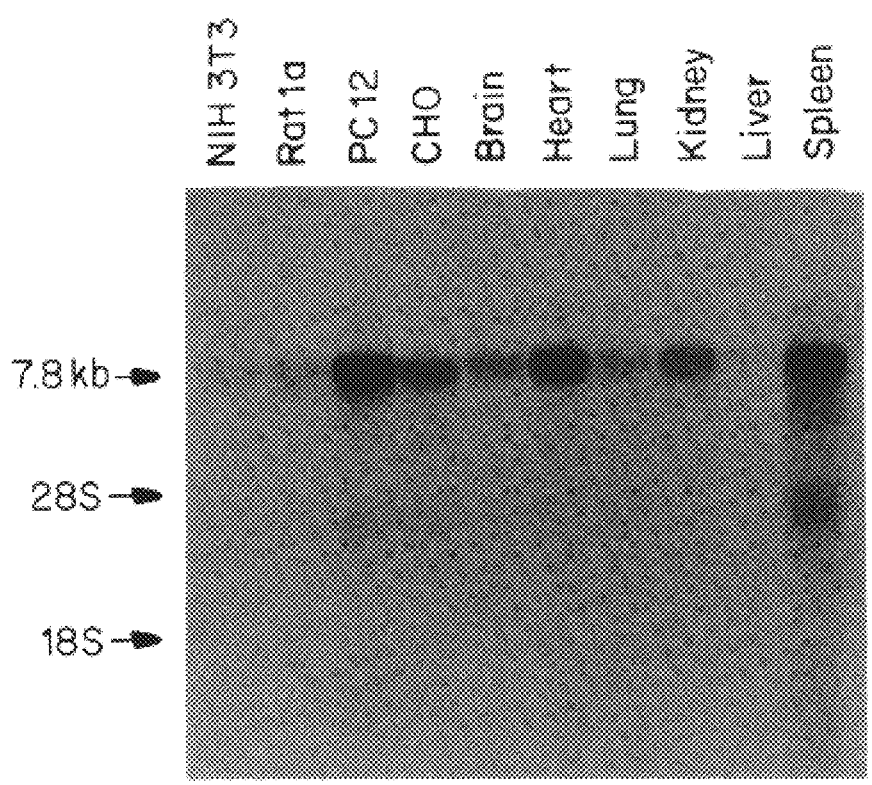
FIG. 3A shows a Northern (RNA) blot of a single 7.8 kb MEKK mRNA in several cell lines and mouse tissues.

Equal amounts (20 μg) of total RNA were loaded onto the gel as indicated by ethidium bromide staining. Blots were probed with either a 320-bp cDNA fragment encoding a portion of the MEKK1 kinase domain or an 858-bp fragment encoding a portion of the NH$_2$ terminal region of MEKK1 using standard methods in the art. Referring to FIG. 3A, a 7.8 kb mRNA was identified with probes derived from both the 5' and 3' ends of the MEKK1 cDNA in several cell lines and mouse tissues. The MEKK mRNA was highly expressed in mouse heart and spleen, an in lower amounts in liver.

C. Southern Blot Analysis

Figure 3B:
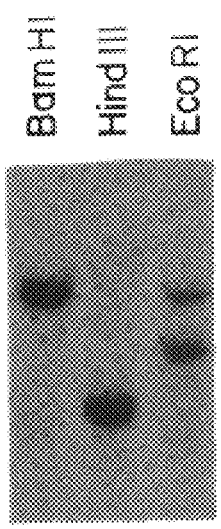
FIG. 3B shows a Southern (DNA) blot of the MEKK gene.

Mouse genomic DNA (10 μg) was digested with either Bam HI, Hind III or Eco RI and applied to gels using standard methods in the art. Blots were probed with a 320-bp fragment of the MEKK1 gene. FIG. 3B shows the appearance of one band in the Bam HI and Hind III digests which indicates that MEKK is encoded by one gene. The appearance of two bands in the Eco RI digest indicates the likely presence of an Eco RI site within an intron sequence spanned by the probe.

D. Immunoblots Using Anti-MEKK Antibodies

Three polyclonal antisera were prepared using three different antigens. A first polyclonal antiserum was prepared using an antigen comprising a 15 amino acid peptide Asp Arg Pro Pro Ser Arg Glu Leu Leu Lys His Pro Val Glu Arg (SEQ ID NO: 13) derived from the COOH-terminus of MEKK1 corresponding to amino acids 655 to 669 of SEQ ID NO:2. NZW rabbits were immunized with the peptide and antisera was recovered using standard methods known in the art. This first polyclonal antiserum is hereinafter referred to as the DRPP antiserum.

A second polyclonal antiserum was produced using a DNA clone comprising an MEKK1 cDNA digested with EcoR1 and PstI, thereby creating a 1270 bp fragment that encodes the amino terminus of MEKK1. This fragment was cloned into pRSETC to form the recombinant molecule pMEKK$_{1-369}$ comprising amino acid residues 1 to 369 of MEKK1. The pMEKK$_{1-369}$ recombinant molecule was expressed in *E. coli* and protein encoded by the recombinant molecule was recovered and purified using standard methods known in the art. NZW rabbits were immunized with the purified recombinant MEKK$_{1-369}$ protein and antisera was recovered using standard methods known in the art. This second polyclonal antiserum is hereinafter referred to as the MEKK$_{1-369}$ antiserum.

A third polyclonal antiserum was produced using a DNA clone comprising an MEKK1 cDNA digested with Pst I and Kpn 1, thereby creating a 1670 bp fragment that encodes the catalytic domain of MEKK1. This fragment was cloned into PRSETC to form the recombinant molecule pMEKK$_{370-672}$ comprising amino acid residues 370 to 672 of MEKK1 (encoded by base pairs 1592–3260). The pMEKK$_{370-672}$ recombinant molecule was expressed in *E. coli* and protein encoded by the recombinant molecule was recovered and purified using standard methods known in the art. NZW rabbits were immunized with the purified recombinant MEKK$_{370-672}$ protein and antisera was recovered using standard methods known in the art. This second polyclonal antiserum is hereinafter referred to as the MEKK$_{370-672}$ antiserum.

Figure 3C:
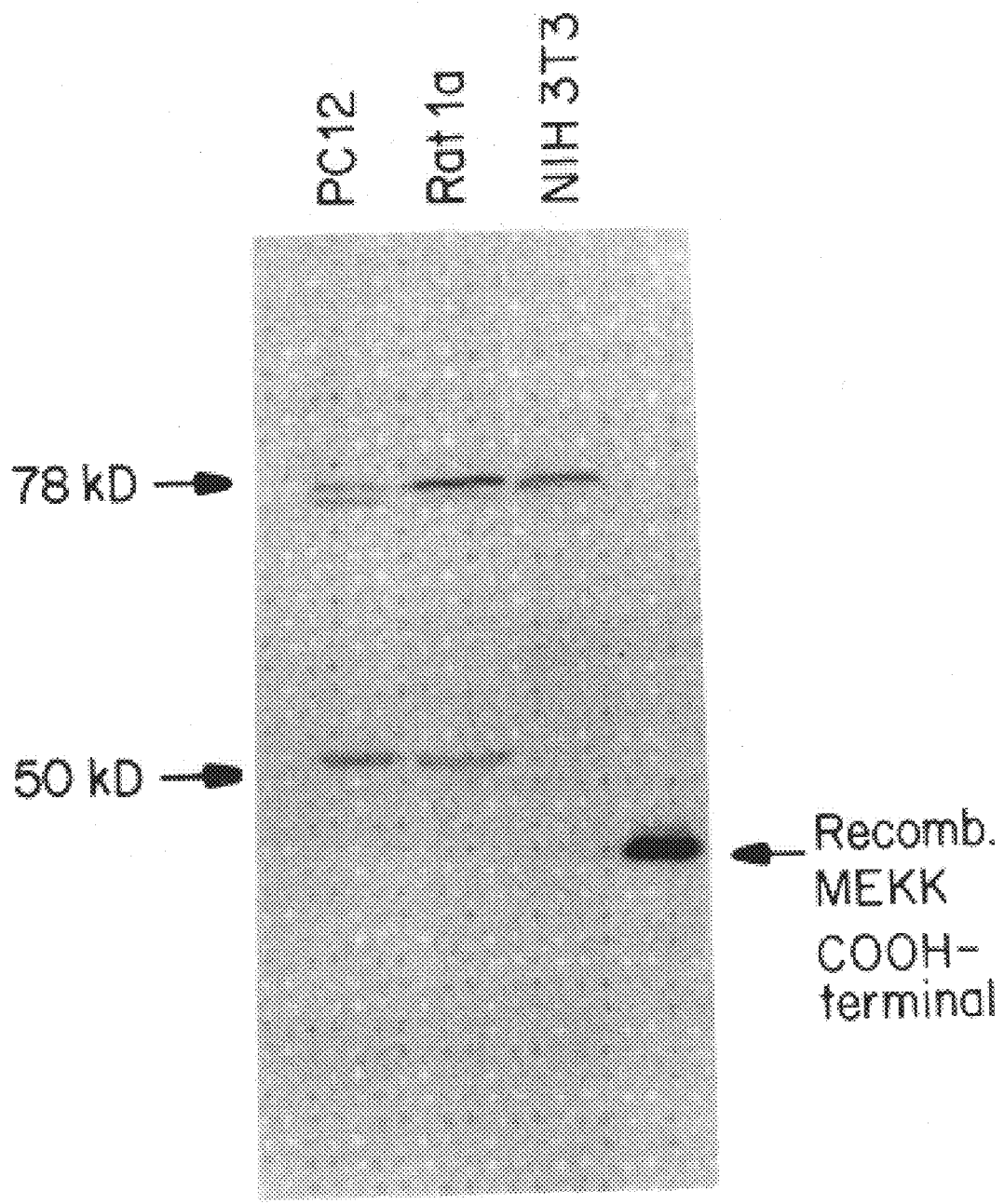
FIG. 3C shows an immunoblot showing expression of the 78 kD and 50 kD forms of MEKK in rodent cell lines.

The DRPP antiserum was used to probe Western Blots of soluble cellular protein derived from several rodent cell lines. Soluble cellular protein (100 µg) or recombinant MEKK COOH-terminal fusion protein (30 ng) was loaded onto a 10% Tris Glycine SDS-PAGE gel and the protein transferred to a nylon filter using methods standard in the art. The nylon filter was immunoblotted with affinity purified DRPP antiserum (1:300 dilution). Referring to FIG. 3C, a 78 kD immunoreactive protein was identified in the samples comprising protein from Pheochromocytoma (PC12), Rat 1a, and NIH 3T3 cells. A prominent 50 kD immunoreactive band was also commonly present but varied in intensity from preparation to preparation indicating the band is a proteolytic fragment. Visualization of both the 78 kD and 50 kD immunoreactive bands on immunoblots was inhibited by pre-incubation of the 15 amino acid peptide antigen with the affinity purified DRPP antiserum. The MEKK protein detected by immunoblotting is similar to the molecular size predicted from the open reading frame of the MEKK1 cDNA.

Figure 4:
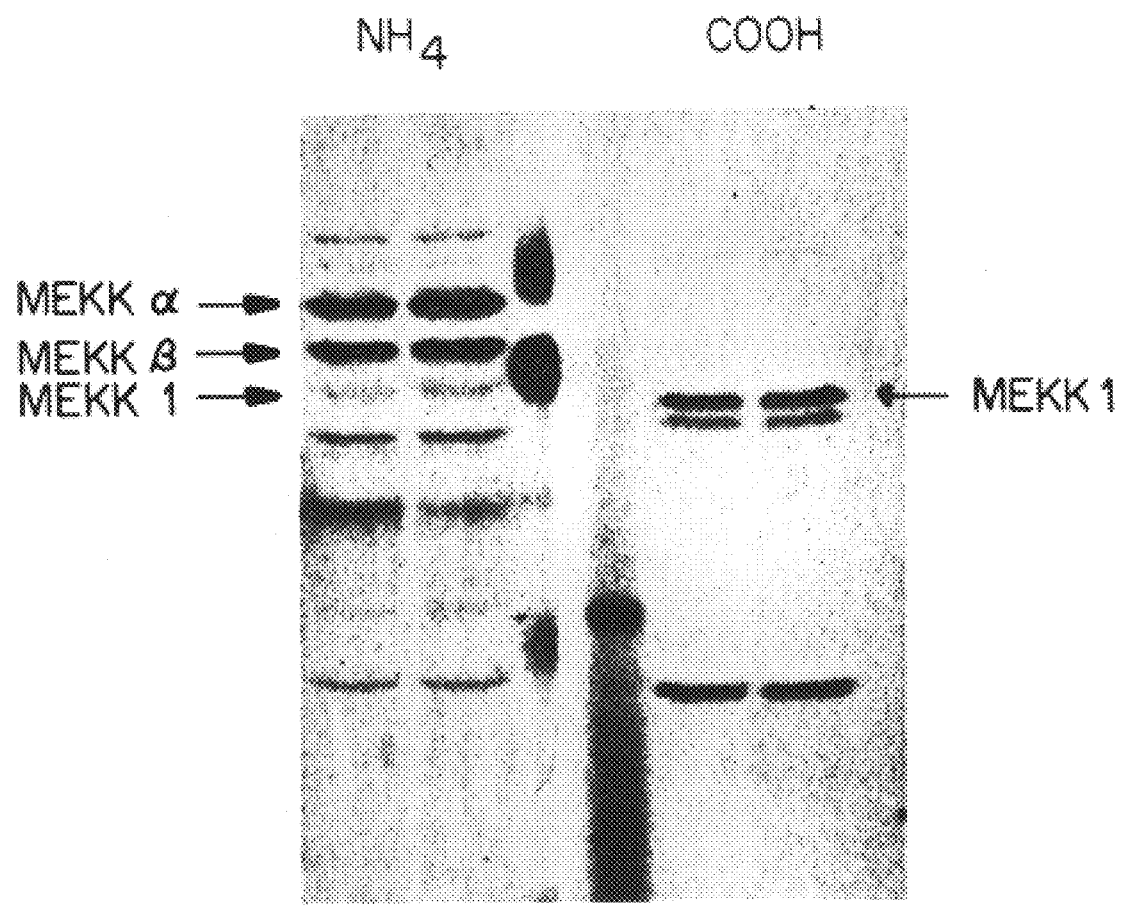
FIG. 4 shows immunprecipitates of MEKK protein using MEKK antiserum.

In a second immunoblot experiment, PC12 cells stimulated or not stimulated with EGF were lysed and resolved on 10% Tris Glycine SDS-PAGE gel as described above. MEKK proteins contained in the cell lysates were identified by immunoblot using affinity purified MEKK$_{1-369}$ antiserum (1:300) using methods standard in the art. Referring to FIG. 4, MEKK1 and two higher molecular weight proteins having MEKK activity, MEKKα and MEKKβ, were identified using the affinity purified MEKK$_{1-369}$ antiserum. MEKK1, and not MEKKα and MEKKβ, were identified using the affinity purified MEKK$_{370-672}$ antiserum.

Using the same procedure described above, two MEKK immunoreactive species of approximately 98 kD and 82 kD present in PC12, Rat1a, NIH3T3, and Swiss3T3 cell lysates were recognized by affinity purified MEKK$_{1-369}$ antiserum as shown in FIG. 5. It should be noted that the 98 kD MEKK protein described herein was originally identified as a 95 kD MEKK protein in the related PCT application (International application no. PCT/US94/04178). Visualization of both of these proteins was inhibited by incubation of the affinity purified MEKK$_{1-369}$ antiserum with purified recombinant MEKK$_{1-369}$ fusion protein antigen. A single 98 kD MEKK protein was present in MEKK immunoprecipitates, but not in immunoprecipitates using preimmune serum. More of the 98 kD MEKK was expressed in PC12 cells relative to fibroblast cell lines. Immunoblotting with antibodies that specifically recognize Raf-1 or Raf-B indicated that neither of these enzymes were present as contaminants of MEKK immunoprecipitates. 98 kD MEKK in MEKK immunoprecipitates did not comigrate with Raf-1 or Raf-B in PC12 cell lysates and no cross-reactivity between MEKK and Raf antibodies was observed.

Example 2

This example describes the isolation of nucleic acid sequences encoding MEKK2, MEKK3 and MEKK4 protein.

PCR primers were designed based on the nucleotide sequence of MEKK1. PCR amplification of fragments from DNA isolated from reverse transcriptase reactions of RNA isolated form PC12 and HL60 cells was conducted using standard techniques. The resultant PCR products were cloned into the pGEX cloning vector (Promega, Wis.) using standard procedures and submitted to DNA sequence analysis using standard techniques.

Example 3

This example describes the expression of MEKK1 protein in COS-1 cells to define its function in regulating the signaling system that includes MAPK.

COS cells in 100-mm culture dishes were transfected with either the pCVMV5 expression vector alone (1 µg: control) or the pCVMV5 MEKK construct (1 µg: MEKK). After 48 hours, the cells were placed in serum-free medium containing bovine serum albumin (0.1 percent) for 16 to 18 hours to induce quiescence. Cells were then treated with human EGF (30 ng/ml) (+EGF) or buffer (control) for 10 minutes, washed twice in cold phosphate buffered saline (PBS), and lysed in cell lysis buffer containing 50 mM β-glycerophosphate (pH 7.2), 100 µM sodium vanadate, 2 mM MgCl$_2$, 1 mM EGTA Triton X-100 (0.5 percent), leupeptin (2 µg/ml), aprotinin (2 µg/ml), and 1 mM dithiothreitol (600 µl). After centrifugation for 10 minutes at maximum speed in a microfuge, COS cell lysates containing 0.5 to 1 mg of soluble protein were subjected to FPLC on a MONO Q column, and eluted fractions were assayed for MAPK activity according to the method described in Heasley et al., p. 545, 1992, *Mol. Biol. Cell*, Vol. 3.

Figure 6A:
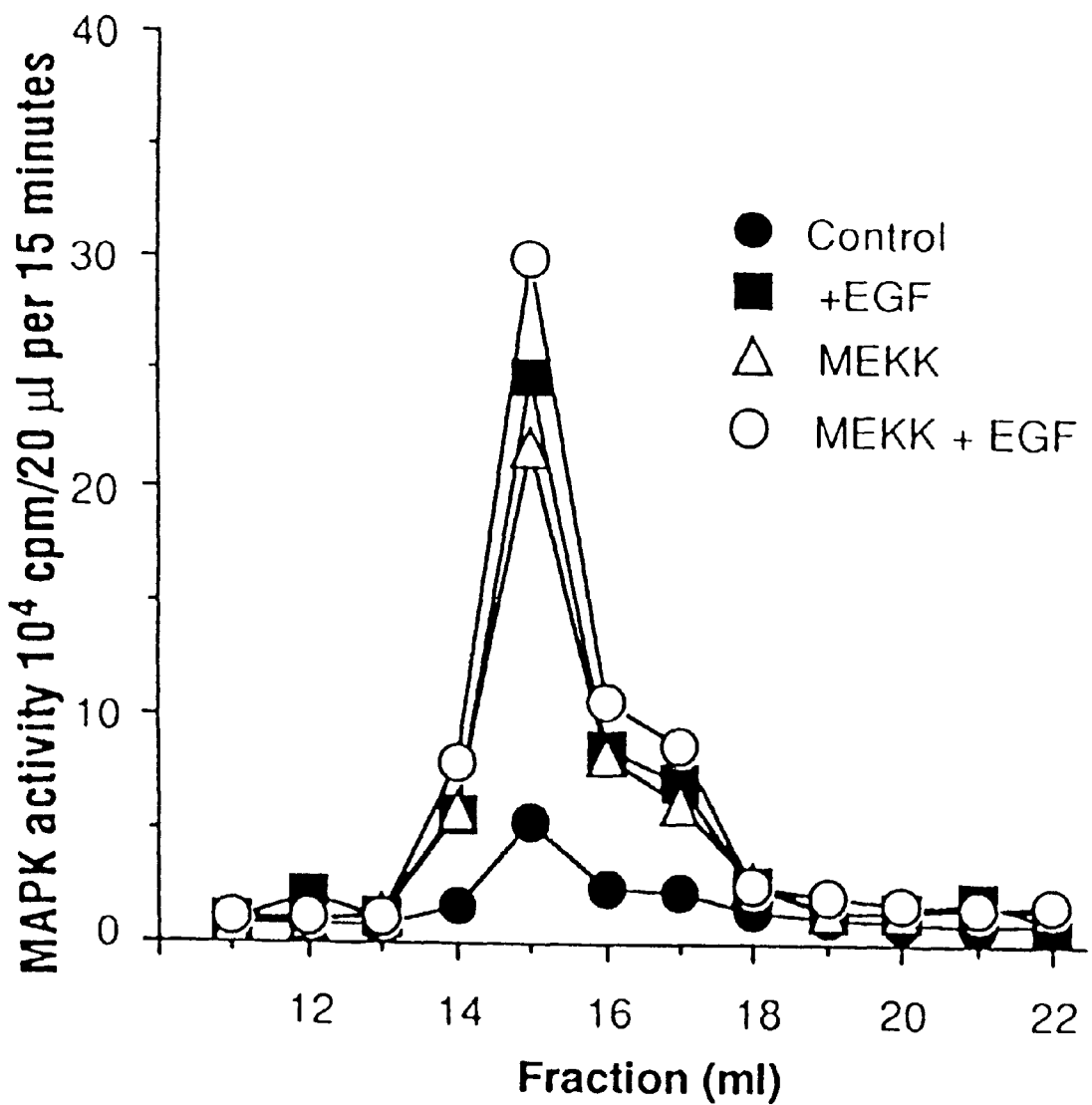
FIG. 6A shows the activation of MAPK in COS cells transfected with MEKK.

Referring to FIG. 6A, when MEKK1 was overexpressed in COS 1 cells, MAPK activity was four to five times greater than that in control cells transfected with plasmid lacking an MEKK1 cDNA insert. The activation of MAPK occurred in COS cells deprived of serum and in the absence of any added growth factor. The activity of MAPK was similar to that observed after stimulation of control cells with EGF. Stimulation of COS cells transiently overexpressing MEKK with EGF resulted in only a slight increase in MAPK activity compared to that observed with MEKK expression alone.

Figure 6B:
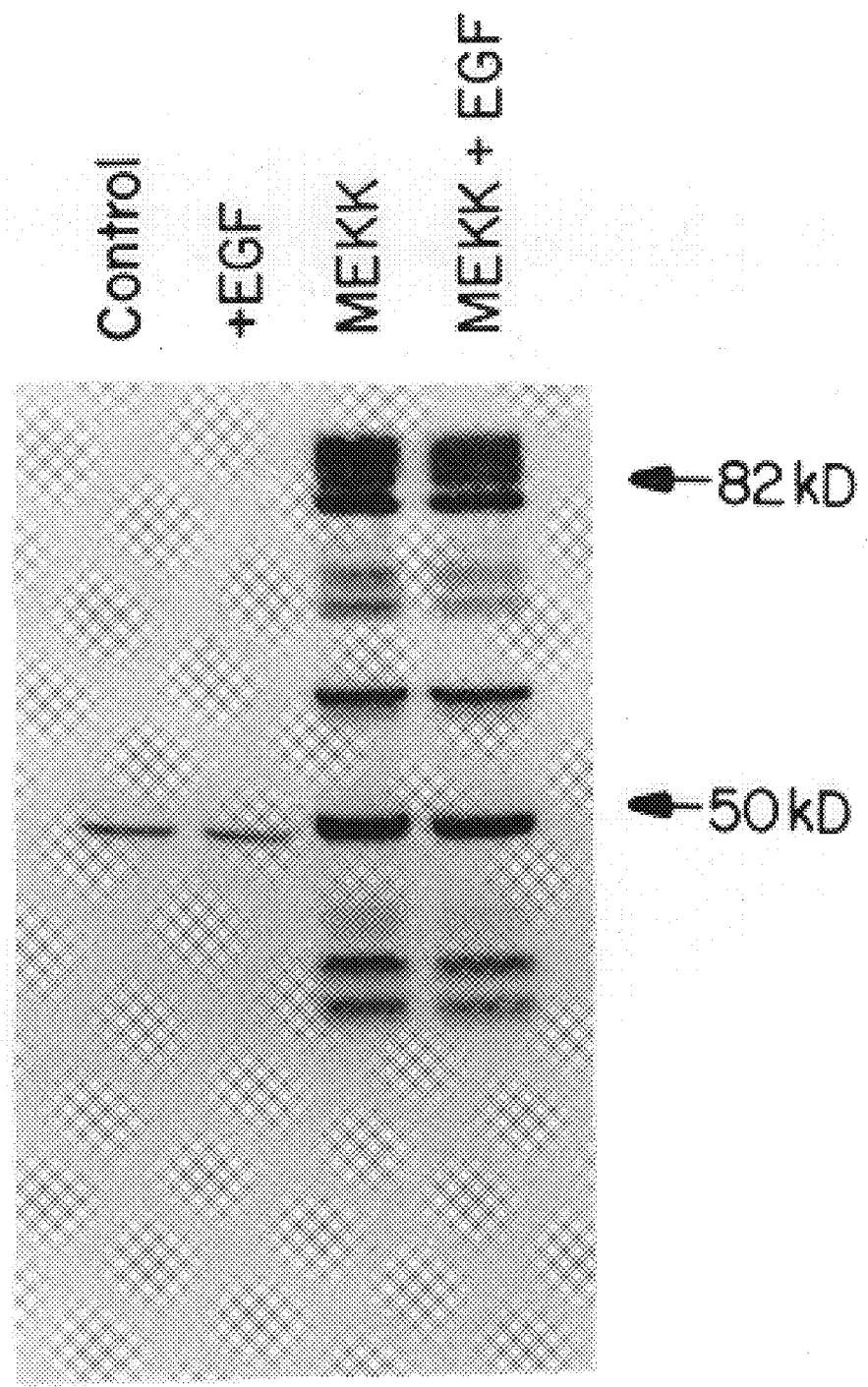
FIG. 6B is an immunoblot showing expression of MEKK in cells either treated or not treated with EGF.

To ensure that MEKK protein was present in the samples tested for MAPK activity, protein from cell lysates of the transfected COS 1 cells were immunoblotted with MEKK specific antiserum. Equal amounts (100 µg) of soluble protein lysate from COS cells were placed on the gel for immunoblotting using the methods described in Example 1. The filters were immunoblotted using the affinity purified DRPP antiserum (1:300) and affinity purified MEKK$_{1-369}$ antiserum (1:300). Referring to FIG. 6B, the results indicate that expression of MEKK in cells transfected with vector encoding MEKK that were treated with or without EGF. Only the 50 kD MEKK immunoreactive fragment was detected in lysates from control COS cells using the DRPP antiserum. Transient expression of MEKK in COS cells yielded a predominant 82 kD band that was slightly larger than that observed in PC12, Rat 1a, or NIH 3T3 cells. Addition of the 15 amino acid DRPP peptide antigen to the antiserum during immunoblotting prevented detection of all of the immunoreactive bands; these bands were not detected in extracts of control COS cells, an indication that they were derived from the expressed MEKK protein.

Example 4

This Example describes the expression of MEKK1 in COS cells to test the ability of MEKK protein to activate MEK protein.

Recombinant MAPK was used to assay MEK activity in COS cell lysates that had been fractionated by fast protein liquid chromatography (FPLC) on a Mono S column. A cDNA encoding p42 MAPK from Xenopus laevis was cloned into the pRSETB expression vector. This construct was used for expression in the LysS strain of Escherichia coli BL21(DE3) of a p42 MAPK fusion protein containing a polyhistidine sequence at the $NH_2$-terminus. Cultures containing the expression plasmid were grown at 37° C. to an optical density of 0.7 to 0.9 at 600 nM. Isopropyl-β-thiogalactopyranoside (0.5 mM) was added to induce fusion protein synthesis and the cultures were incubated for 3 hours. The cells were then collected and lysed by freezing, thawing, and sonication. The lysate was centrifuged at 10,000 g for 15 minutes at 4° C. The supernatant was then passed over a $Ni^{2+-}$ charged Sepharose resin and the soluble recombinant MAPK was eluted in sodium phosphate buffer (pH 4.5). The purified recombinant MAPK was more than 80 percent pure. The purified recombinant MAPK served as a substrate for MEK and catalyzed the phosphorylation of a peptide consisting of residues 662 to 681 of the EGF receptor ($EGFR^{662-681}$).

Soluble cell lysates from COS cells transiently transfected with MEKK, mock-transfected (control), or mock-transfected and treated with EGF (30 ng/ml) (+EGF), were fractionated by FPLC on a Mono S column and endogenous MEK activity was measured. Endogenous MAPK eluted in fractions 2 to 4, whereas MEK was contained in fractions 9 to 13. For assaying endogenous MEK activity, cells were washed twice in cold PBS and lysed in 650 µl of a solution containing 50 mM β-glycerophosphate, 10 mM N-N-morpholinoethane-sulfonic acid (pH 6.0), 100 µM sodium vanadate, 2 mM $MgCl_2$, 1 mM EGTA, Triton X-100 (0.5 percent), leupeptin (5 µg/ml), aprotinin (2 µg/ml), and 1 mM dithiothreitol. After centrifugation at maximum speed for 10 minutes in a microfuge, soluble cell lysates (1 to 2 mg of protein) were applied to a Mono S column equilibrated in elution buffer (50 mM β-glycerophosphate, 10 mM MES (pH 6.0), 100 µM sodium vanadate, 2 mM $MgCl_2$, 1 mM EGTA, and 1 mM dithiothreitol. The column was washed with buffer (2 ml) and bound proteins were eluted with a 30 ml linear gradient of 0 to 350 mM NaCl in elution buffer. A portion (30 µl) of each fraction was assayed for MEK activity by mixing with buffer (25 mM β-glycerophosphate, 40 mM N-(2-hydroxyethyl)piperazine-N'-(2-ethanolsulfonicacid) (pH7.2) 50 mM sodium vanadate, 10 mM $MgCl_2$, 100 µM γ-$^{32}$P-ATP (3000 to 4000 cpm/pmol), inhibitor protein-20 (IP-20; Thy Thy Tyr Ala Asp Phe Ile Ala Ser Gly Arg Thr Gly Arg Arg Asn Ala Ile His Asp (SEQ ID NO: 14) 25 µg/ml), 0.5 mM EGTA, recombinant MAP kinase (7.5 µg/ml), and 200 µM $EGFR^{662-681}$) in a final volume of 40 µl. After incubation at 30° C. for 20 minutes, the incorporation of γ-$^{32}$P-ATP into $EGFR^{662-681}$ was measured. In this assay, the ability of each column fraction to activate added recombinant MAPK was measured by the incorporation of γ-$^{32}$P-ATP into the MAPK substrate, a peptide derived from the EGF receptor (EGFR).

Figure 7:
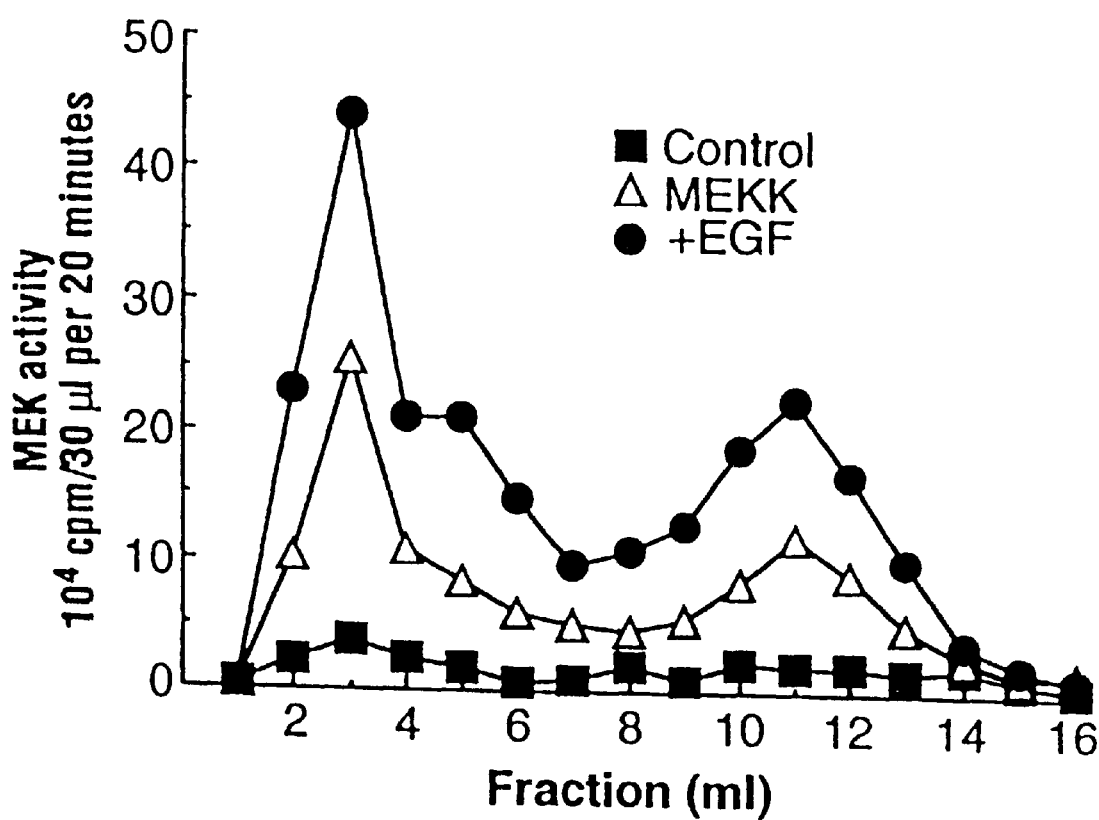
FIG. 7 shows the activation and phosphorylation of MEK in COS cells transfected with MEKK.

Referring to FIG. 7, the first peak of activity eluted represents endogenous activated MAPK, which directly phosphorylates the EGFR peptide substrate. The second peak of activity represents the endogenous MEK in COS cells.

COS cell lysates were fractionated by FPLC on a Mono Q column to partially purify the expressed MEKK. Purified recombinant MEK-1 was then used as a substrate for MEKK in the presence of γ-$^{32}$P-ATP to determine whether MEKK directly phosphorylates MEK-1.

A cDNA encoding MEK-1 was obtained from mouse B cell cDNA templates with the polymerase chain reaction and oligodeoxynucleotide primers corresponding to portions of the 5' coding region and 3' untranslated region of MEK-1. The catalytically inactive MEK-1 was generated by site-directed mutagenesis of $Lys^{343}$ to Met. The wild-type MEK-1 and catalytically inactive MEK-1 proteins were expressed in pRSETA as recombinant fusion proteins containing a polyhistidine sequence at their $NH_2$-termini.

Lysates from COS cells transfected with MEKK or mock-transfected (control) were subjected to FPLC on a Mono Q column as described above. Portions (20 µl) of fractions containing MEKK were mixed with buffer containing 50 mM β-glycerophosphate (pH 7.2), 100 µM sodium vanadate, 2 nM $MgCl_2$, 1 mM EGTA, 50 µM ATP, IP-20 (50 µg/ml), and 10 µl γ-$^{32}$P-ATP in a reaction volume of 40 µl and incubated for 40 minutes in the presence (+) or absence (−) of recombinant, catalytically inactive MEK-1 (150 ng) (kinase-MEK-1). Reactions were stopped by the addition of 5×SDS sample buffer (10 µl), 1×SDS buffer contains 2 percent SDS, 5 percent glycerol, 62.5 mM tris-HCl (pH 6.8), 5 percent β-mercaptoethanol, and 0.001 percent bromophenol blue. The samples were boiled for 3 minutes and subjected to SDS-PAGE and autoradiography.

Figure 8A:
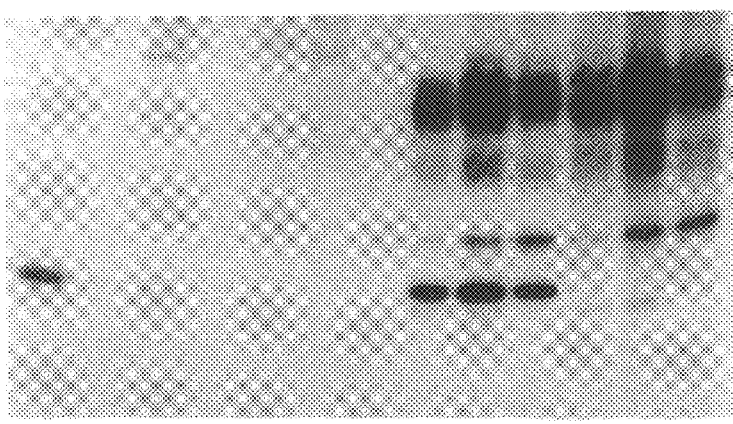
FIG. 8A shows the phosphorylation of MEK-1 by MEKK.

Referring to FIG. 8A, autophosphorylated recombinant wild-type MEK-1 (WT MEK-1) comigrated with phosphorylated catalytically inactive MEK-1. Thus, MEKK was capable of phosphorylating MEK-1. Corresponding fractions of lysates from control cells, however, were not able to phosphorylate MEK-1.

Example 5

Figure 8B:
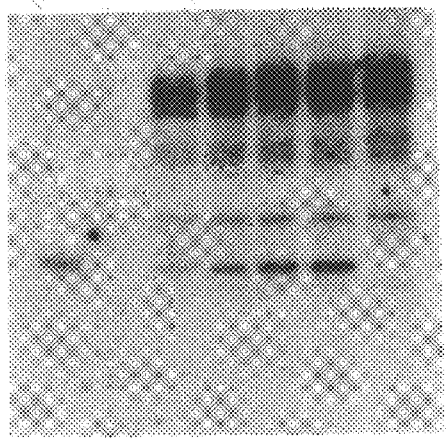
FIG. 8B shows the time course of phosphorylation of MEK-1 by MEKK expressed in COS cells.
Figure 8C:
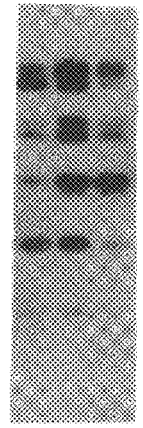
FIG. 8C is an immunoblot of MEKK overexpressed in COS cells.

Phosphorylation of catalytically inactive MEK-1 by MEKK was time dependent (FIG. 8B); MEKK was also phosphorylated. Fraction 22 from FPLC on a Mono Q column (20 µl) was incubated with or without recombinant catalytically inactive MEK-1 (0.15 µg) for the indicated times. Referring to FIG. 8B, phosphorylation of kinase MEK-1 and MEKK was visible after 5 minutes and maximal after about 20 minutes. The time-dependent increase in MEKK phosphorylation correlated with a decreased mobility of the MEKK protein during SDS-PAGE. Referring to FIG. 8C, immunoblotting demonstrated that the MEKK protein co-eluted (after FPLC on a Mono Q column) with the peak of activity (fraction 22) that phosphorylated MEK. The slowly migrating species of MEKK were also detected by immunoblotting. Thus, expression of MEKK appears to activate MAPK by activating MEK.

Example 6

This Example describes that the phosphorylation of MEK by overexpressed MEKK resulted in activation of MEK, recombinant wild-type MEK-1 and a modified form of MAPK that is catalytically inactive.

Figure 9A:
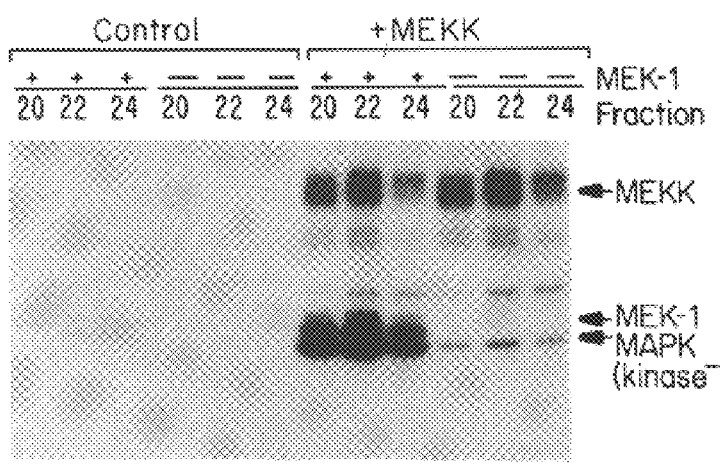
FIG. 9A shows the phosphorylation of MAPK by activated MEK-1.

COS cell lysates were separated by Mono Q-FPLC and fractions containing MEKK were assayed for their ability to activate added wild-type MEK-1 such that it would phosphorylate catalytically inactive recombinant MAPK in the presence of $\gamma$-$^{32}$P-ATP. Lysates from COS cells transfected with MEKK or mock-transfected (control) were fractionated by FPLC on a Mono Q column and portions (20 $\mu$l) of fractions containing MEKK were mixed with buffer. Each fraction was incubated in the presence (+) or absence (−) of purified recombinant wild-type MEK-1 (150 ng) and in the presence of purified recombinant, catalytically inactive (kinase$^-$) MAPK (300 ng). Referring to FIG. 9A, fractions 20 to 24 from lysates of COS cells transfected with MEKK activated MEK-1. Thus, MEKK phosphorylated and activated MEK-1, leading to MAPK phosphorylation.

Example 7

This Example describes studies demonstrating that MEKK activated MEK directly, and not through the activation of one or more other kinases contained in the column fractions.

Overexpressed MEKK was immunoprecipitated from COS cell lysates with affintiy purified MEKK$_{1-369}$ antiserum. Immunoprecipitated MEKK was resuspended in 10 to 15 $\mu$l of PAN (10 mM piperazine-N, N'-bis-2-ethanesulfonic acid (Pipes) (pH 7.0), 100 mM NaCl, and aprotinin (20 $\mu$g/ml) and incubated with (+) or without (−) catalytically inactive MEK-1 (150 ng) and 25 $\mu$Ci of $\gamma$-$^{32}$P-ATP in 20 mM pipes (pH 7.0), 10 mM MnCl$_2$, and aprotinin (20 $\mu$g/ml) in a final voume of 20 $\mu$l for 15 minutes 30° C. Reactions were stopped by the addition of 5×SDS sample buffer (5 $\mu$l). The samples were boiled for 3 minutes and subjected to SDS-PAGE and autoradiography.

Figure 9B:
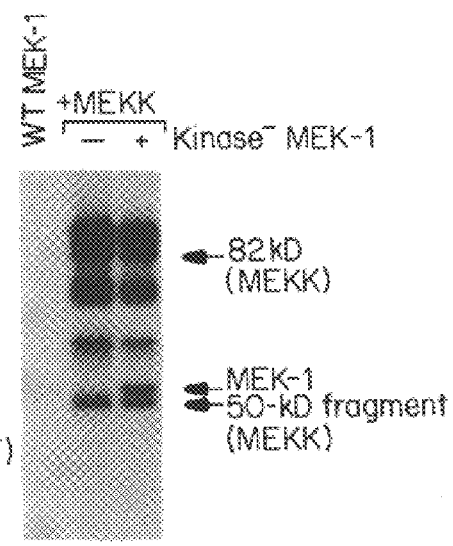
FIG. 9B shows phosphorylation of MEK-1 by immunoprecipitated MEKK.

Referring to FIG. 9B, MEKK phosphorylated catalytically inactive MEK-1, which comigrated with wild-type MEK-1 on SDS-PAGE. Several phosphorylated bands of overexpressed MEKK were detected in the immunoprecipitates. These bands probably resulted from autophosphorylation of MEKK and corresponded to the forms of MEKK identified by immunoblotting of lysates from COS cells transfected with MEKK. Immunoprecipitates obtained with pre-immune serum contained no MEKK and did not phosphorylate MEK-1. Thus, MEKK appears to directly phosphorylate MEK.

Taken together, the results from Examples 4 through 7 show that MEKK can phosphorylate and activate MEK, which in turn phosphorylates and activates MAPK.

Example 8

This Example demonstrates that Raf can also phosphorylate and activate MEK.

Figure 10A:
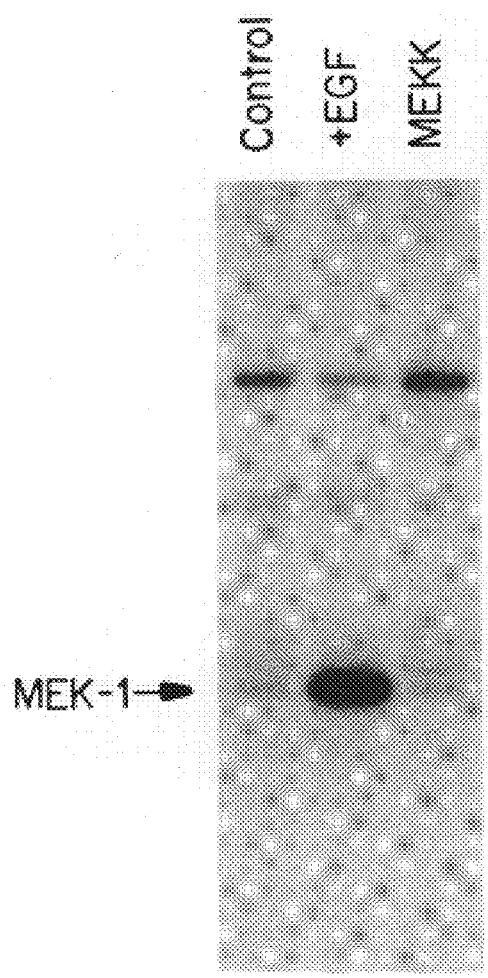
FIG. 10A shows the phosphorylation of MEK-1 by activated Raf.
Figure 10B:
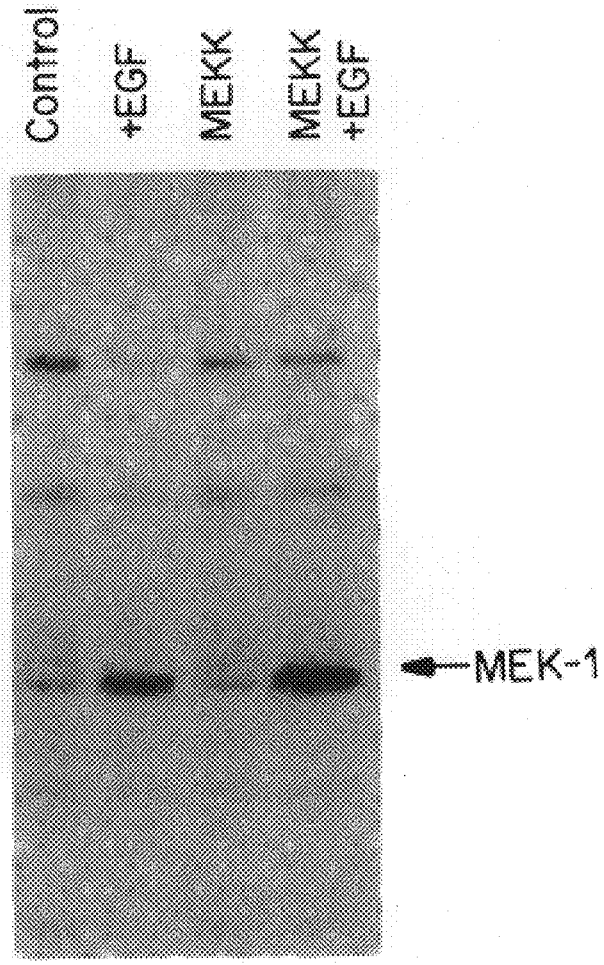
FIG. 10B shows the phosphorylation state of Raf isolated from COS cells which are overexpressing MEKK and have been treated with EGF.

COS cells deprived of serum were stimulated with EGF, and Raf was immunoprecipitated with an antibody to the COOH-terminus of Raf-1. Cos cells were transiently transfected with vector alone (control) or with the PCV/M5-MEKK construct (MEKK). Quiescent control cells were treated with or without human EGF (30 ng/ml) for 10 minutes and Raf was immunoprecipitatd from cell lysates with an antibody to a COOH-terminal peptide from Raf. Immunoprecipitated Raf was incubated with catalytically inactive MEK-1 (150 ng) and 25 $\mu$l of $\gamma$-$^{32}$P-ATP. The immunoprecipitated Raf phosphorylated MEK-1 in the presence of $\gamma$-$^{32}$P-ATP (FIG. 10A). Little or no phosphorylation of MEK-1 by Raf was observed in immunoprecipitates of Raf from COS cells overexpressing MEKK. Treatment of COS cells overexpressing MEKK with EGF resulted in a similar degree of phosphorylation of MEK-1 by immunoprecipitated Raf (FIG. 10B). Cells transfected with MEKK and deprived of serum were treated with EGF, and Raf was immunoprecipitated and incubated with catalytically inactive MEK-1. Equal amounts of Raf were immunoprecipitated in each sample as demonstrated by immunoblotting with antibodies to Raf. The slowest migrating band represents an immunoprecipitated phosphoprotein that is unrelated to Raf or MEK-1. The amount of Raf in the immunoprecipitates from control cells and cells transfected with MEKK was similar as shown by subsequent SDS-PAGE and immunoblotting with the antibody to Raf. Thus, both MEKK and Raf can independently activate MEK.

Example 9

This Example describes the activation of a 98 kD MEKK protein isolated from PC12 cells in response to stimulation of cells containing MEKK protein by growth factors.

PC12 calls were deprived of serum by incubation in starvation media (DMEM, 0.1% BSA) for 18–20 hours and MEKK was immunoprecipitated from lysates containing equal amounts of protein from untreated controls or cells treated with EGF (30 ng/ml) or NGF (100 ng/ml) for 5 minutes with the above-described anti-MEKK antibodies speicific for the NH$_4$-terminal portion of MEKK. Immunoprecipitated MEKK was resuspended in 8 $\mu$l of PAN (10 mM piperazine-N,N'-bis-2-ethanesulfonic acid (Pipes) (pH 7.0), 100 mM NaCl, and aprotinin (20 $\mu$g/ml)) and incubated with catalytically inactive MEK-1 (150 ng) and 40 $\mu$Ci of ($\gamma$-$^{32}$P) ATP in universal kinase buffer (20 mM piperazine-N,N'-bis-2-ethanesulfonic acid (Pipes) (pH 7.0), 10 mM MnCl$_2$, and aprotinin (20 $\mu$g/ml)) in a final volume of 20 $\mu$l for 25 minutes at 30° C. Reactions were stopped by the addition of 2×SDS sample buffer (20 $\mu$l). The samples were boiled for 3 minutes and subjected to SDS-PAGE and autoradiography. Raf-B was immunoprecipitated from the same untreated and treated PC12 cell lysates as above with an antiserum to a COOH-terminal peptide of Raf-B (Santa Cruz Biotechnology, Inc.) and assayed similarly. Raf-1 was immunoprecipitated with an antiserum to the 12 COOH-terminal amino acids of Raf-1 (Santa Cruz Biotechnology, Inc.). Epidermal growth factor (EGF) treatment of serum starved PC12 cells resulted in increased MEKK activity.

Figure 11:
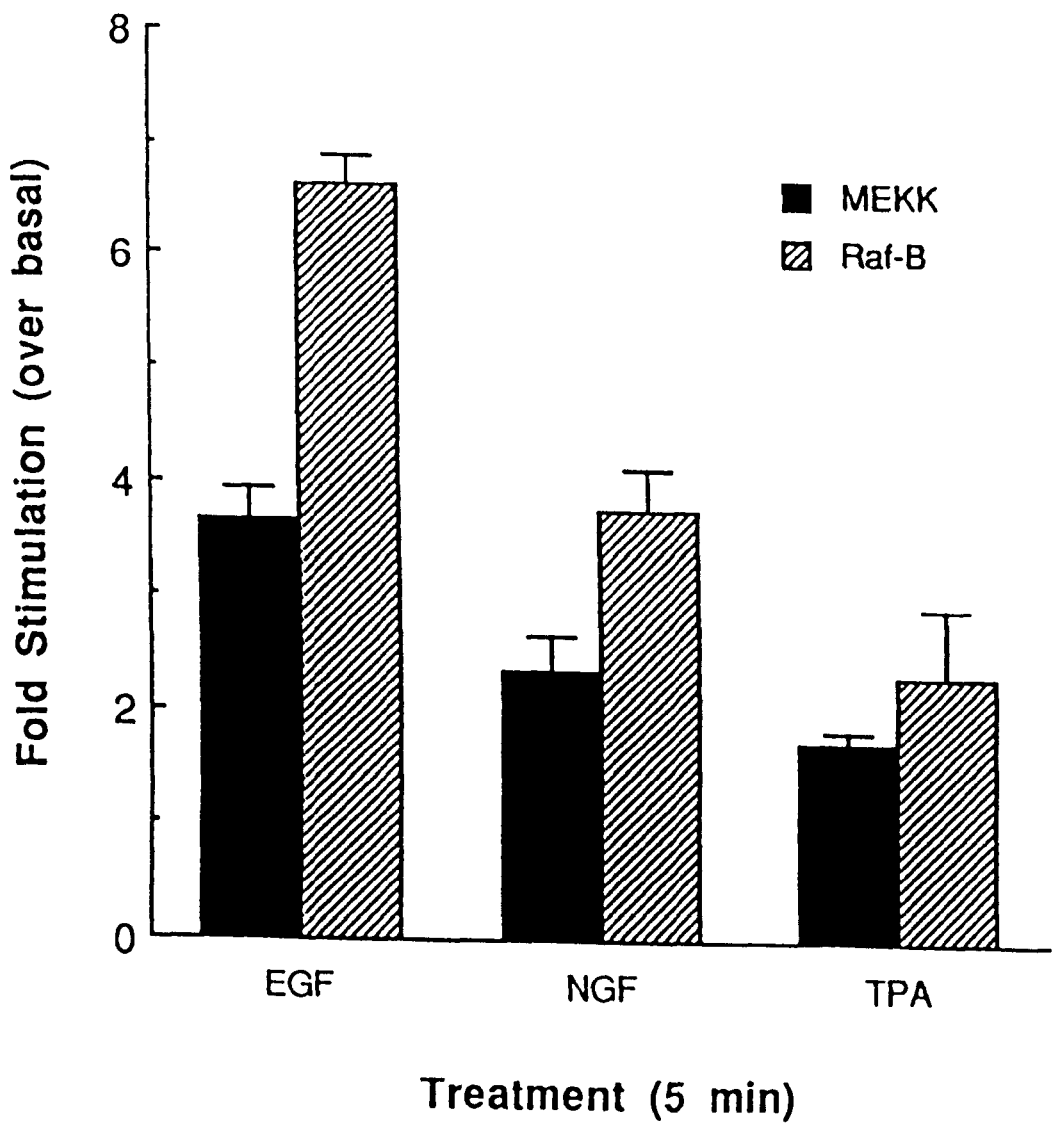
FIG. 11 shows the relative ability of immunoprecipitated MEKK and Raf-B to phosphorylate kinase inactive MEK-1.

Referring to FIG. 11, the results were obtained by measuring the phosphorylation of purified MEK-1 (a kinase inactive form) by immunoprecipitates of MEKK in in vitro kinase assays. NGF stimulated a slight increase in MEKK activity compared to control immunoprecipitates from untreated cells. Stimulation of MEKK activity by NGF and EGF was similar to Raf-B activation by these agents, although Raf-B exhibited a high basal activity. Activation of c-Raf-1 by NGF and EGF was almost negligible in comparison to that of MEKK or Raf-B.

Figure 12:
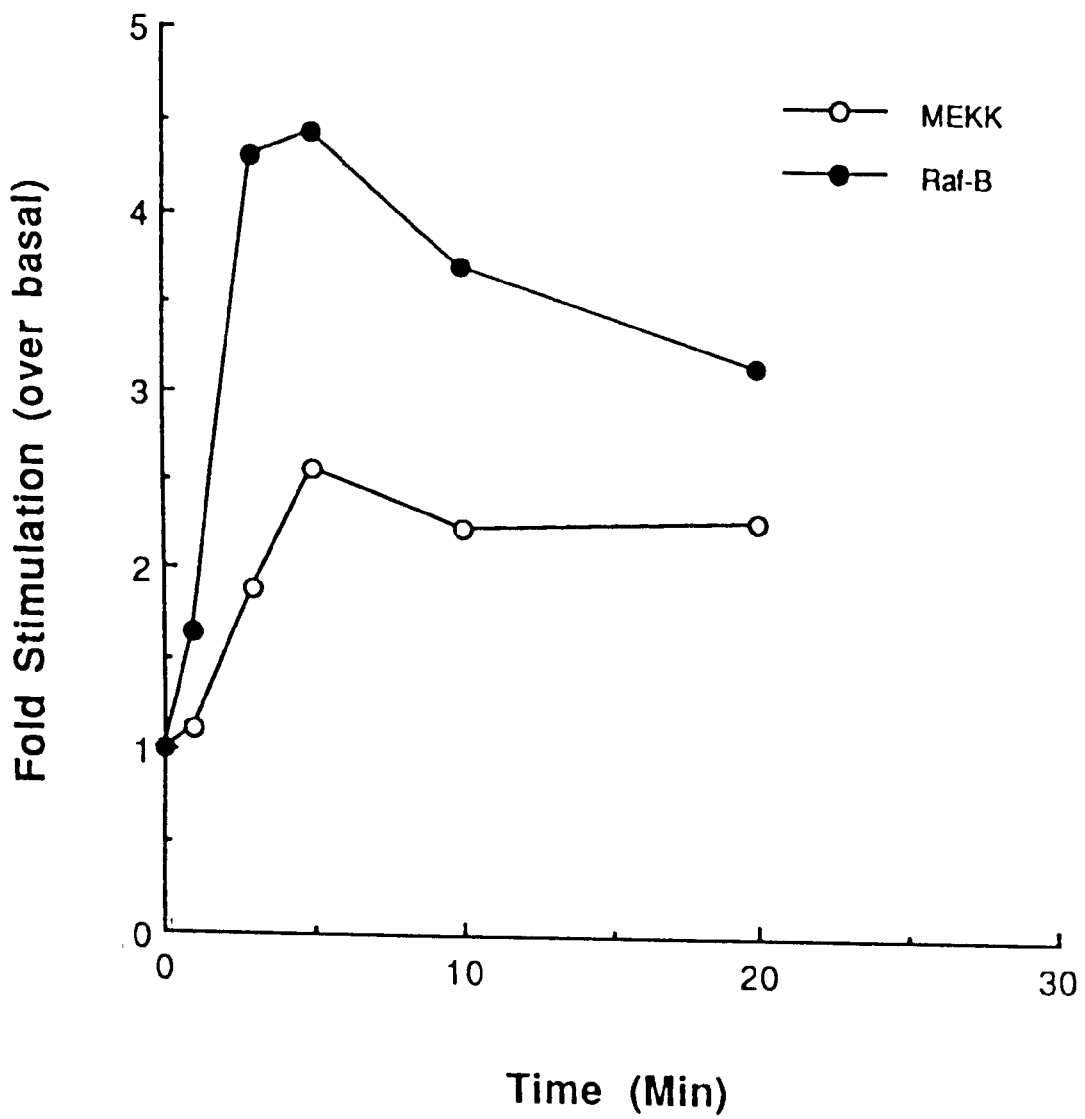
FIG. 12 shows a time course of EGF-stimulated MEKK and Raf-B activation.

A timecourse of MEKK stimulation by EGF was established by immunoprecipitating MEKK or Raf-B protein from lysates of PC12 cells treated with EGF (30 ng/ml) for 0, 1, 3, 5, 10, or 20 minutes and incubating the protein with catalytically inactive MEK-1 (150 ng) and ($\gamma$-$^{32}$P)ATP as described above. Data represent the relative magnitude of the response for each timepoint as quantitated by phosphorimager analysis of radioactive gels from a typical experiment. A timecourse of EGF treatment indicated that MEKK activation reached maximal levels following 5 minutes and persisted for at least 30 minutes (FIG. 12). Raf-B exhibited a similar timecourse; peak activity occurred within 3–5 minutes following EGF treatment and was persistent for up to 20 minutes.

Figure 13:
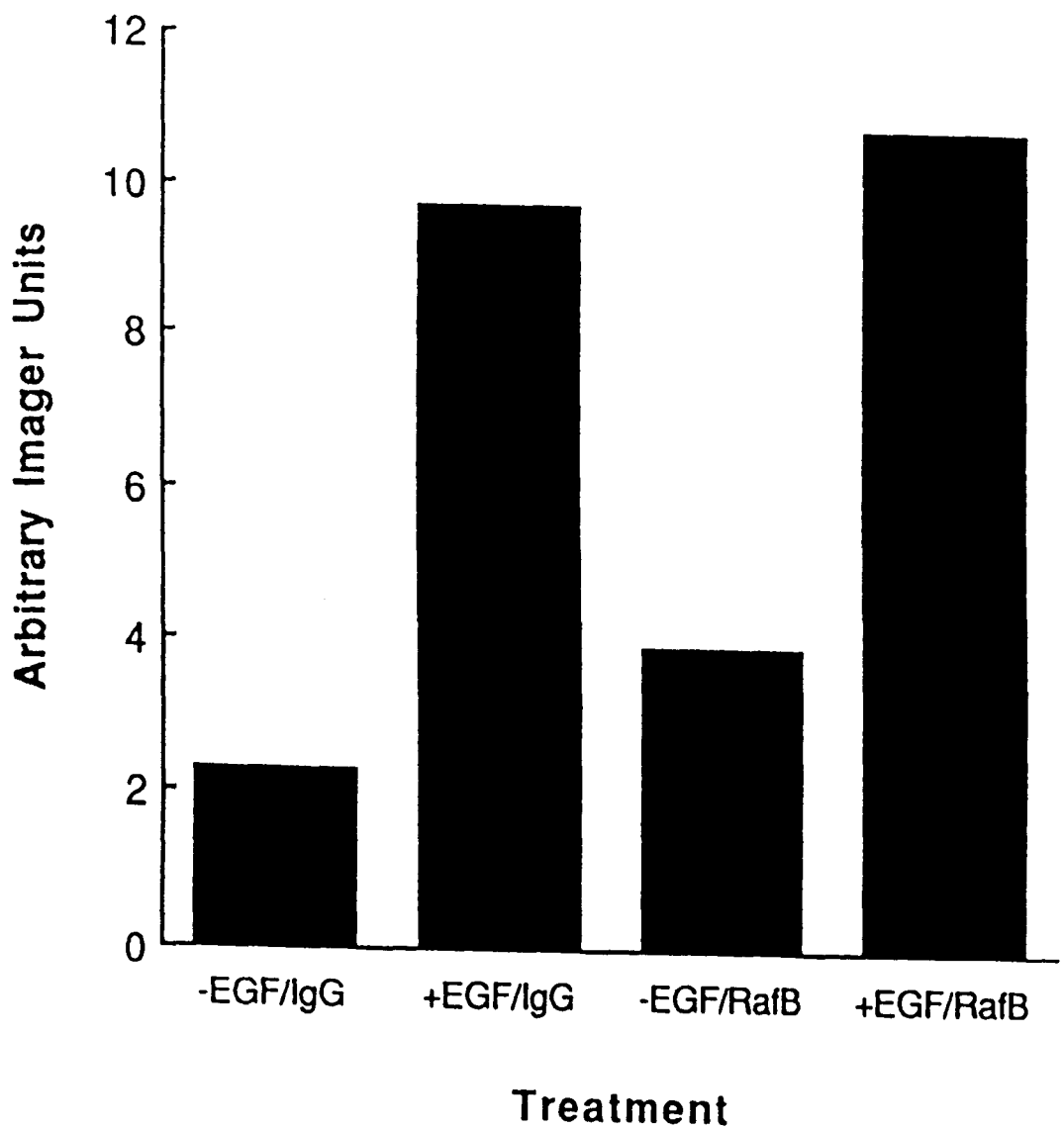
FIG. 13 shows that the immunodepletion of Raf-B from MEKK immunoprecipitates has no effect on MEKK activity.
Figure 14:
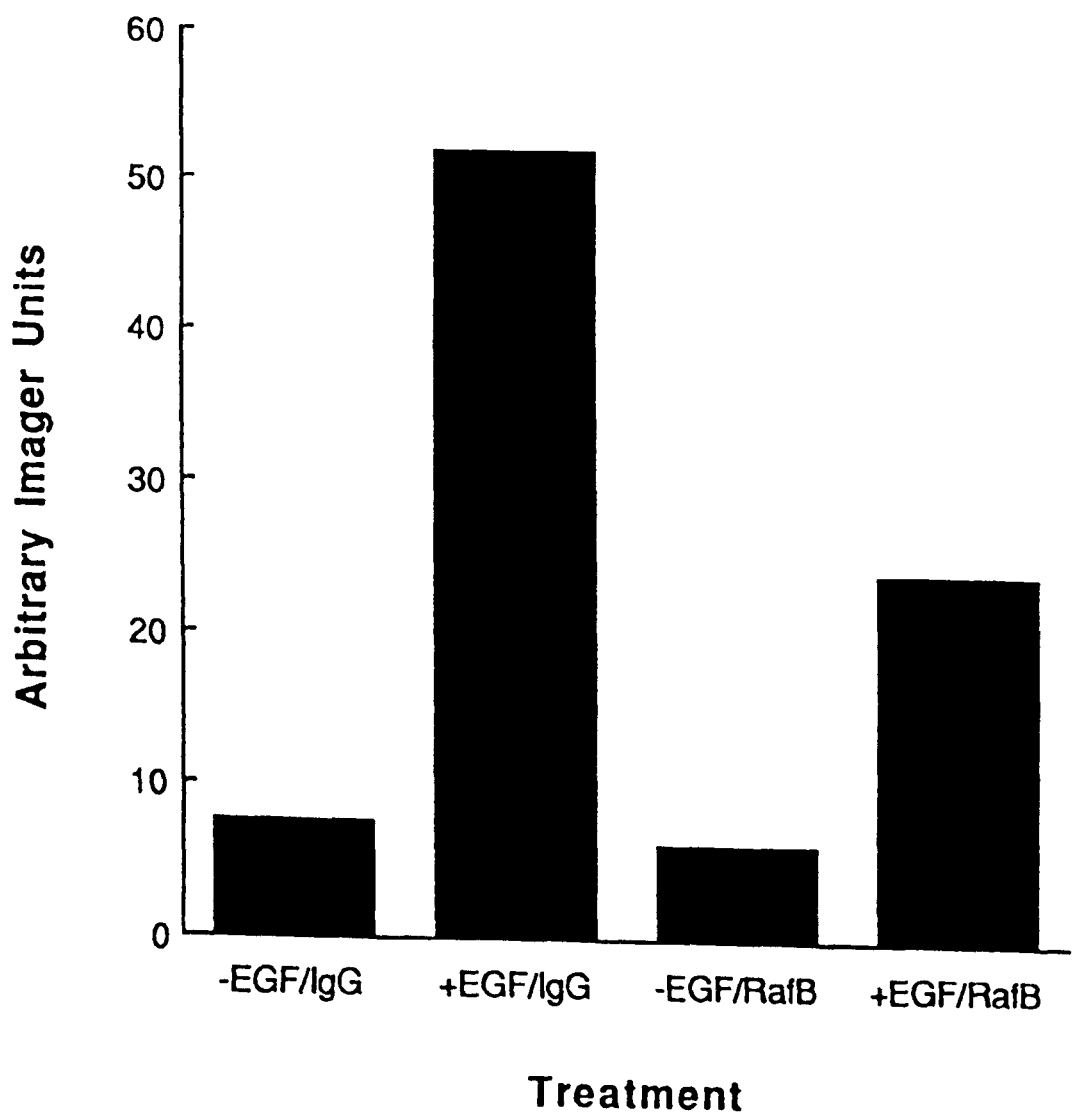
FIG. 14 shows that the immunodepletion of Raf-B from MEKK immunoprecipitates decreases Raf-B activity.

To further dissociate EGF-stimulated MEKK activity from that of Raf-B, Raf-B was immunodepleted from cell lysates prior to MEKK immunoprecipitation. Raf-B was pre-cleared from lysates of serum-starved PC12 cells which had been either treated or not treated with EGF (30 ng/ml) for 5 minutes. Raf-B was pre-cleared two times using antisera to Raf-B or using preimmune IgG antisera as a control. The pre-cleared supernatant was then immunoprecipitated with either MEKK or Raf-B antisera and incubated with catalytically inactive MEK-1 and ($\gamma$-$^{32}$P)ATP as described in detail above. EGF-stimulated and unstimulated PC12 cell lysates were precleared with either IgG or Raf-B antisera and then subjected to immunoprecipitation with MEKK antiserum or Raf-B antibodies. The results shown in FIG. 14 indicate that pre-clearing with Raf-B resulted in a 60% diminution of Raf-B activity as measured by phosphorimager analysis of Raf-B in vitro kinase assays. FIG. 13 shows that EGF-stimulated MEKK activity was unaffected by Raf-B depletion, suggesting that Raf-B is not a component of MEKK immunoprecipitates. At least 40% of the Raf-B activity is resistant to preclearing with Raf-B antibodies. Recombinant wild type MEKK over-expressed in COS cells readily autophosphorylates on serine and threonine residues and the amino-terminus of MEKK is highly serine and threonine rich. MEKK contained in immunoprecipitates of PC12 cells were tested for selective phosphorylation of purified recombinant MEKK amino-terminal fusion protein in in vitro kinase assays.

Serum-starved PC12 cells were treated with EGF (30 ng/ml) for 5 minutes and equal amounts of protein from the same cell lysates were immunoprecipitated with either MEKK, Raf-B, or preimmune antiserum as a control. Immunoprecipitates were incubated with purified recombinant MEKK NH$_2$-terminal fusion protein (400 ng) and ($\gamma$-$^{32}$P) ATP as described above. MEKK immunoprecipitated from lysates of EGF-stimulated and unstimulated PC12 cells robustly phosphorylated the inert 50 kD MEKK NH$_2$-fusion protein, while Raf-B or preimmune immunoprecipitates from EGF-stimulated or unstimulated cells did not use the MEKK NH$_2$-fusion protein as a substrate. Thus, the EGF-stimulated MEKK activity contained in MEKK immunoprecipites is not due to contaminating Raf kinases.

Example 10

This Example describes MEKK activity in FPLC Mono Q ino-exchnage column fractions of PC12 cell lysates.

Figure 15A:
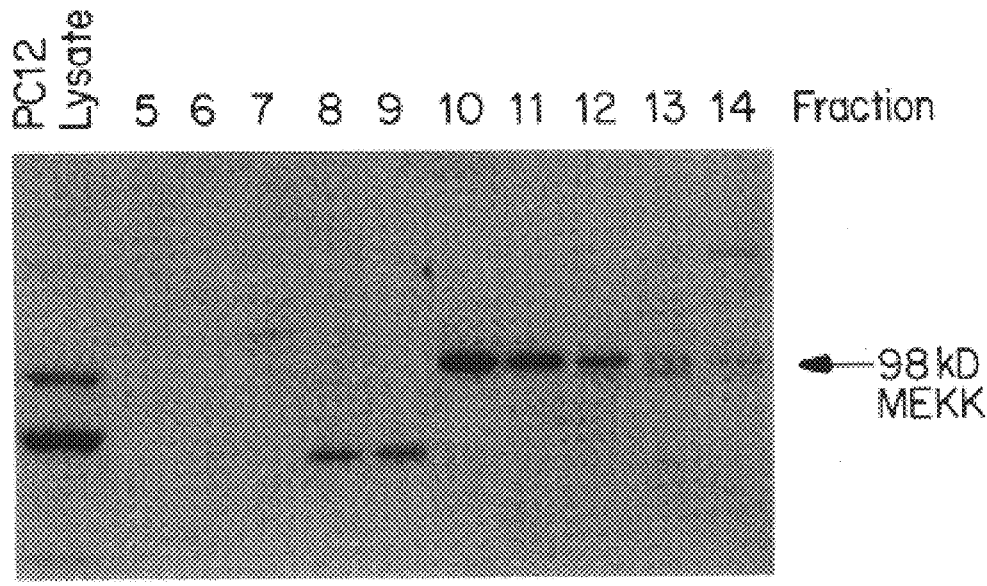
FIG. 15 shows MEKK activity in FPLC Mono Q ion-exchange column fractions of PC12 cell lysates.

Cell lysates were prepared from EGF-stimulated PC12 cells. Portions (900 $\mu$l) of 1 ml column fractions (1 to 525 mM NaCl gradient) were concentrated by precipitation with trichloroacetic acid and loaded on gels as described above. The gels were blotted and then immunoblotted with MEKK specific antibody. The results are shown in FIG. 15A indicate that 98 kD MEKK immunoreactivity eluted in fractions 10 to 12. The peak of B-Raf immunoreactivity eluted in fraction 14, whereas Raf-1 was not detected in the eulates from the column.

Figure 15B:
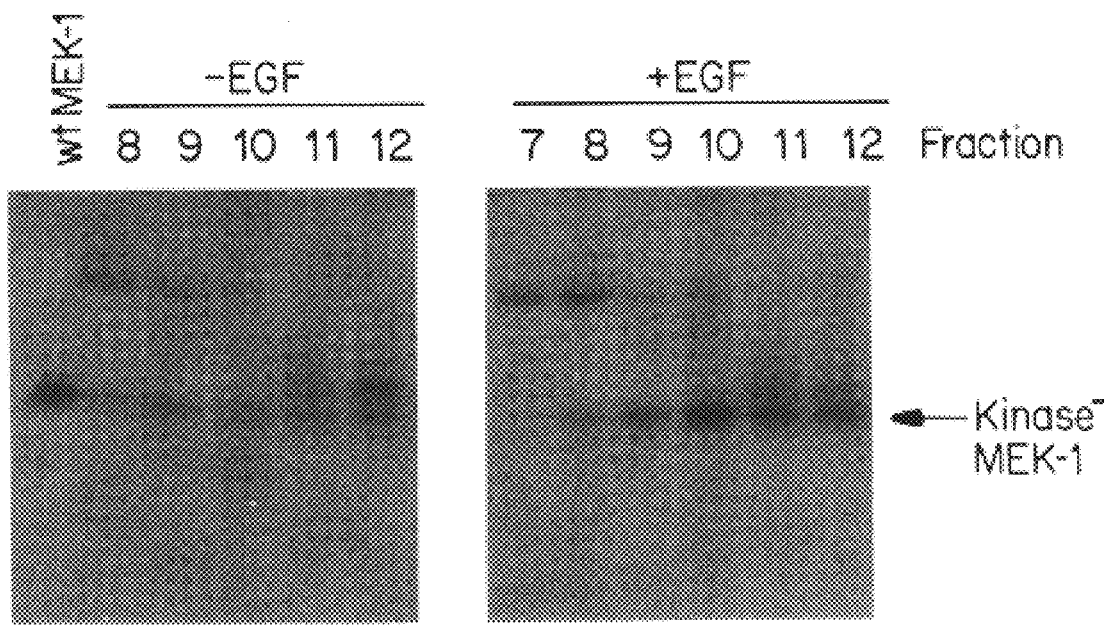

Portions (30 $\mu$l) of each fraction from the PC12 lysates of unstimulated control cells or EGF-treated cells were assayed as described above in buffer containing purified recombinant MEK-1 (150 ng) as a substrate. The results shown in FIG. 15B indicate that the peak of MEKK activity eluted in fractions 10 to 12 from EGF-stimulated PC12 cells phosphorylated MEK, whereas little MEK phosphorylation occurred in fractions from unstimulated cells.

Example 11

This Example describes studies demonstrating that the phosphorylation of both MEK-1 and the MEKK NH$_2$-terminal fusion protein were due to the activity of the 98 kD PC12 cell MEKK.

Cell lysates prepared from EGF-stimulated and unstimulated cells were fractionated by FPLC on a Mono-Q column to partially purify the endogenous MEKK. Lysates from unstimulated control PC12 cells or cells treated with EGF (30 ng/ml) for 5 minutes were fractionated by FPLC on a Mono Q column using a linear gradient of 0 to 525 mM NaCl. A portion (30 $\mu$l) of each even numbered fraction was mixed with buffer (20 mM piperazine-N,N'-bis-2-ethanesulfonic acid (Pipes) (pH 7.0), 10 mM MnCl$_2$, aprotinin (20 $\mu$g/ml), 50 mM $\beta$-glycerophosphate (pH 7.2), 1 mM EGTA, IP-20 (50 $\mu$g/ml), 50 mM NaF, and 30 $\mu$Ci ($\gamma$-$^{32}$P)ATP) containing purified recombinant MEK-1 (150 ng) as a substrate in a final volume of 40 $\mu$l and incubated at 30° C. for 25 minutes. Reactions were stopped by the addition of 2×SDS sample buffer (40 $\mu$l), boiled and subjected to SDS-PAGE and autoradiography. The peak of MEKK activity eluted in fractions 10–12. Portions (30 $\mu$l) of each even numbered fraction from lysates of EGF-treated PC12 cells were mixed with buffer as described above except containing purified recombinant MEKK NH$_2$-terminal fusion protein (400 ng) as a substrate instead of MEK-1. Purified recombinant kinase inactive MEK-1 or the MEKK NH$_2$-terminal fusion protein were then used as substrates in the presence of ($\gamma$-$^{32}$P)ATP to determine whether 98 kD MEKK directly phosphorylates either substrate. Fractions 10–14 of lysate from PC12 cells treated with EGF phosphorylated MEK-1 while little MEK-1 phosphorylation occurred in untreated:control fractions. The MEKK NH$_2$-terminal fusion protein was also phosphorylated in the same fractions as was MEK-1, although the peak of activity was slightly broader (fractions 8–16).

immunoblotting of column fractions demonstrated that the 98 kD MEKK protein co-eluted with the peak of activity that phosphorylated either exogenously added kinase inactive MEK-1 or the 50 kD MEKK NH$_2$-terminal fusion protein. Portions (900 $\mu$l) of even numbered column fractions were concentrated by precipitation with trichloroacetic acid and immunoblotted with MEKK antibody. The peak of immunoreactivity eluted in fractions 10–12.

Example 12

This Example describes the activation of MEK by a 98 kD MEKK.

Figure 17A:
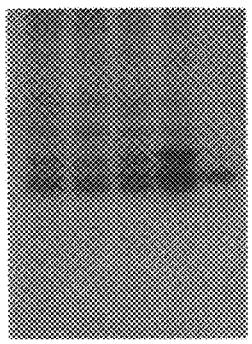
FIG. 17 shows activation of MEK protein by 98 kD MEKK.
Figure 17B:
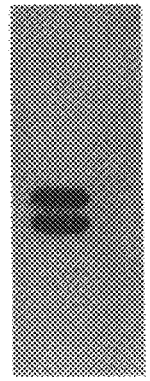
Figure 17C:
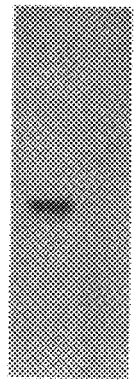

98 kD MEKK was immunoprecipitated using the MEKK$_{1-369}$ antiserum described in Example 1 from untreated (−) or EGF-treated (+) PC12 cell lysates. The immunoprecipitates were incubated in the presence (+) or absence (−) of purified recombinant wild-type MEK (150 ng) and in the presence of purified recombinant catalytically inactive MAPK (300 ng) and ($\gamma$-$^{32}$P)ATP. The results shown in FIG. 17A indicate that immunoprecipitated MEKK from EGF-stimulated cells phosphorylated and activated MEK, leading to MAPK phosphorylation. No phosphorylation of MAPK occurred in the absence of added recombinant MEK. Immunoblotting demonstrated that there was no contaminating MAPK (FIG. 17B) or contaminating MEK (FIG. 17C) in the MEKK immunoprecipitates from the EGF-stimulated PC12 cells. Thus, phosphorylation and activation of MEK is due to EGF stimulation of MEKK activity measured in the immunoprecipitates.

Example 13

This Example describes whether 98 kD PC12 cell MEKK and Raf-B require functional Ras proteins for growth factor mediated signalling.

Figure 16:
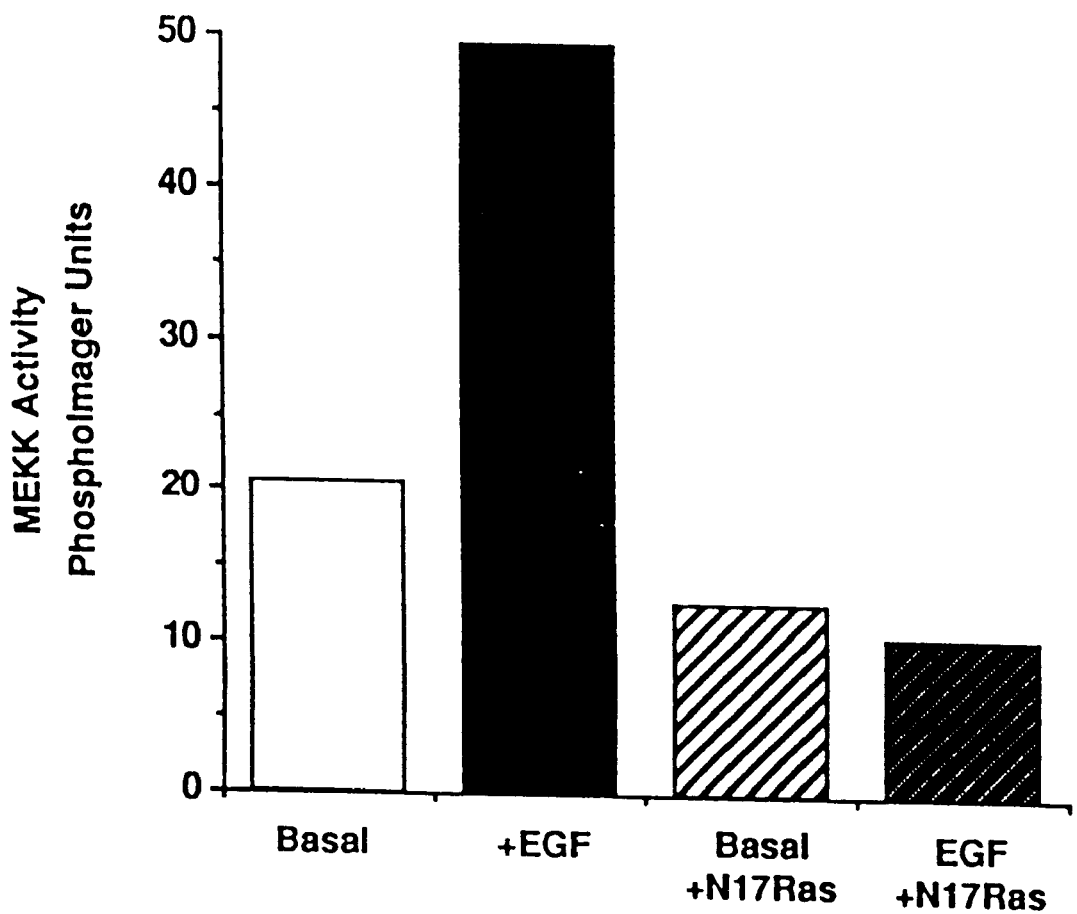
FIG. 16 shows inhibition of MEKK activation by dominant negative $N^{17}RAS$ expression.
Figure 18:
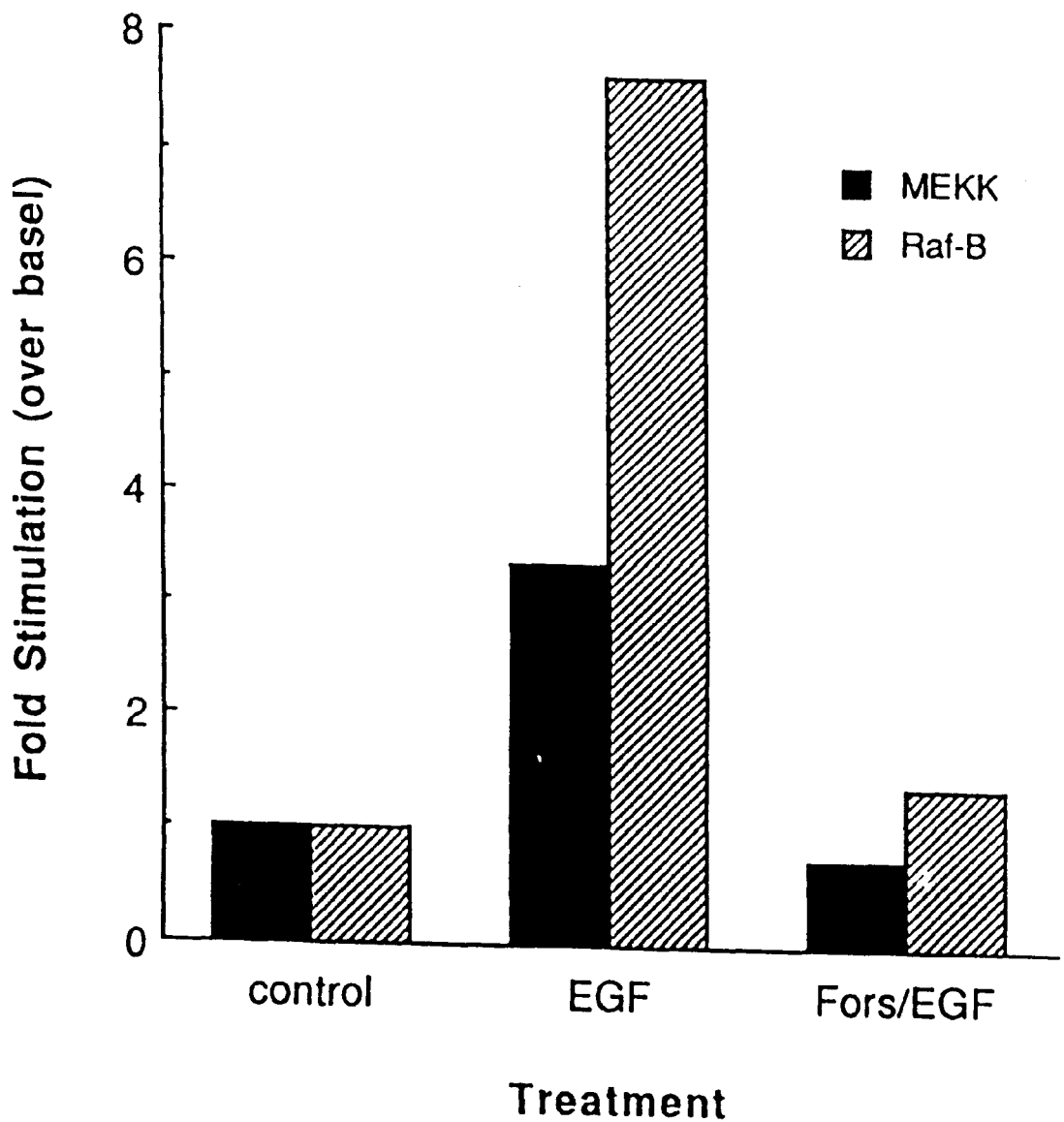
FIG. 18 shows inhibition of EGF activation of MEKK by forskolin.

Dominant negative Ha-ras(Asn 17) ($N^{17}$Ras) was expressed in PC12 cells and EGF-stimulated MEKK or Raf-B activation was assayed in immunoprecipitates using kinase inactive MEK-1 as a substrate. PC12 cells stably expressing dexamethasone inducible $N^{17}$Ras were serum starved for 18–20 hours in media containing 0.1% BSA with or without 1M dexamethasone and then untreated or treated with EGF (30 ng/ml) for 5 minutes. Equal amounts of soluble protein from cell lysates was immunoprecipitated with either MEKK or Raf-B antisera and incubated with purified recombinant catalytically inactive MEK-1 and ($\gamma$-$^{32}$P)ATP as described above. Expression of $N^{17}$Ras was induced in PC12 clones stabley transfected with the $N^{17}$Ras gene by the addition of dexamethasone to the starvation media. FIG. 16 shows that $N^{17}$Ras expression inhibited the activation of MEKK by EGF as measured by its ability to phosphorylate kinase inactive MEK. EGF-mediated activation of Raf-B was also greatly reduced in $N^{17}$Ras expressing PC12 cells compared to uninduced $N^{17}$Ras transfectants. Addition of dexamethasone to wild type PC12 cells had no effect on the magnitude of MEKK or Raf-B activation elicited by EGF. PC12 cell clones stably transfected with the $N^{17}$Ras gene are less responsive to EGF-mediated activation of MEKK activity than are wild type PC12 cells. These results indicate that functional Ras is required for growth factor stimulated activation of both Raf-B and MEKK in PC12 cells, suggesting that Ras may mediate its effects on cell growth and differentiation through the activation of multiple protein kinase effectors from both the Raf and MEKK families. Thus, EGF stimulated a peak of MEKK activity within minutes which persisted for at least 30 minutes following treatment, and was similar to the time-course of Raf-B activation. Nerve growth factor (NGF) and the phorbol ester TPA also activated MEKK, although to a lesser degree than EGF. MEKK activity in immunoprecipitates or column fractions was dissociable from that of EGF-stimulated c-Raf-1 and Raf-B activities. Forskolin pretreatment abolished both MEKK and Raf-B activation by EGF, NGF, and TPA (FIG. 18). Both MEKK and Raf-B activation in response to EGF was inhibited by stable expression of dominant negative $N^{17}$ Ras. These findings represent the first demonstration of Ras-dependent MEKK regulation by growth factors and suggest the emergence of a complex intracellular kinase network in which Ras may alternately couple between members of the Raf and MEKK families.

To determine whether the growth factor-mediated activation of 98 kD PC12 cell MEKK was inhibited by PKA, forskolin was used to elevate intracellular cAMP and activate PKA. Serum-starved PC12 cells were pretreated with or without forskolin (50 $\mu$M) for 3 minutes to activate protein kinase A and then with EGF (30 ng/ml), NGF (100 ng/ml), or TPA (200nM) for 5 minutes and MEKK was immunoprecipitated from equal amounts of soluble protein from cell lysates and incubated with purified recombinant catalytically inactive MEK-1 and ($\gamma$-$^{32}$P)ATP as described above. Raf-B activity was also assayed from the same cell lysates to test whether its regulation differed from that of MEKK. Raf-B was immunoprecipitated from the same cell lysates as described above and assayed for its ability to phosphorylate MEK-1 as described above. Forskolin pretreatment abolished the activation of both MEKK and Raf-B by EGF, NGF, and TPA, as measured by their ability to phosphorylate kinase-inactive MEK-1 (FIG. 18). Forskolin treatment alone had no appreciable effect on either kinase. These results demonstrate that in addition to Raf-1 and Raf-B, PKA activation inhibits growth factor stimulation of 98 kD PC12 cell MEKK, suggesting the existence of a common regulatory control point for PKA action which lies between or downstream of Ras and upstream or at the level of each of these three kinases.

Example 14

This Example describes the determination of whether a similar or distinct MEK activity is involved in activation of MAPK though $G_i$ protein coupled receptors by measuring MEK activity in cell lysates from thrombin stimulated Rat 1a cells.

Thrombin stimulated cells exhibited a MEK activity which co-fractionated with the major MEK peak detected in EGF stimulated cells. The magnitude of MEK activity from thrombin challenged cells was generally two to three-fold less than that observed with EGF stimulation, which correlates with the smaller MAPK response the present inventors have observed in thrombin challenged cells.

Differential regulation of MEK in Rat 1a and NIH3T3 cells expressing gip2, v-src, v-ras, or v-raf led the present inventor to investigate the protein kinases that are putative regulators of MEK-1. Recently, it was shown that Raf-1 can phosphorylate and activate MEK. Raf activation was assayed in the following manner. Cells were serum starved and challenged in the presence or absence of the appropriate growth factors, as described above. Serum starved Rat 1a cells were challenged with buffer alone or with EGF and Raf was immunoprecipitated using an antibody recognizing the C terminus of Raf. Cells were lysed by scraping in ice cold RIPA buffer (50 mM Tris, pH 7.2, 150 nM NaCl, 0.1% SDS, 0.5% sodium deoxycholate, 1.0% Triton X 100, 10 mM sodium pyrophosphate, 25 mM sodium glycerophosphate, 2 mM sodium vanadate, 2.1 $\mu$g/ml aprotinin) and were microfuged for 10 min to remove nuclei. The supernatants were normalized for protein content and precleared with protein A Sepharose prior to immunoprecipitation with rabbit antiserum to the C terminus of Raf-1 and protein A Sepharose for 2–3 h at 4° C. The beads were washed twice with ice cold RIPA and twice with PAN (10 mM Pipes, pH 7.0, 100 mM NaCl, 21 $\mu$g/ml aprotinin). A portion of the immunoprecipitate was diluted with SDS sample buffer and used for immunoblot analysis. The remainder was resuspended in kinase buffer (20 mM Pipes pH 7.0, 10 nM $MnCl_2$, 150 ng kinase-inactive MEK-1, 30 $\mu$Ci $\gamma$-$^{32}$P-ATP and 20 $\mu$g/ml aprotinin) in a final volume of 50 $\mu$l for 30 min at 30° C. Wild type recombinant MEK-1 was autophosphorylated in parallel as a marker. Reactions were terminated by the addition of 12.5 $\mu$l 5×SDS sample buffer, boiled for 5 minutes and subjected to SDS-PAGE and autoradiography.

The immunoprecipitated Raf, in the presence of $\gamma$-$^{32}$P-ATP, was able to phosphorylate MEK-1. The recombinant MEK-1 used in this assay was kinase inactive to ensure it did not autophosphorylate as is observed with wild type MEK-1. Little or no phosphorylation of MEK-1 by Raf was observed in immunoprecipitates from control cells. EGF challenge clearly stimulated Raf catalyzed phosphorylation of MEK-1;

in contrast, thrombin challenge of Rat 1a cells did not measurably activate Raf even though endogenous MEK was clearly activated. EGF stimulated Raf phosphorylation of recombinant MEK-1 by approximately 2.6-fold over basal. Little phosphorylation of MEK by Raf was observed in Raf immunoprecipitates from Gip2 or v-Src expressing Rat 1a cells. EGF stimulation was still capable of activating Raf catalyzed phosphorylation of MEK-1 in these cell lines by 1.8 and 1.4-fold, respectively. The blunting of the EGF response in Gip2 and v-Src expressing cells is likely a result of desensitization of the EGF receptor upon constitutive activation of MAPK. The amount of Raf in the immuno-precipitates was shown to be similar by subsequent SDS-PAGE and immunoblotting using Raf antibody. Since thrombin stimulation of MEK is two to three-fold over basal, at least a 1.5-fold stimulation of MEK phosphorylation is expected if Raf significantly contributed to MEK activation by this growth factor. This level of activation was detectable in the EGF stimulated Gip2 and v-Src expressing cells lines. Thus, it is unlikely that the failure to detect thrombin activation of Raf is due to the sensitivity of the assay. Thrombin stimulation of MAPK is maximal at 3 minutes. Stimulation of Rat 1a cells for 1 or 5 minutes with thrombin did not increase Raf activity.

In NIH3T3 cells, as in Rat 1a cells, EGF activates Raf approximately 2.7-fold, while thrombin does not. V-Raf expressing NIH3T3 cells showed no increase in MEK-1 phosphorylation. This result was unexpected since MEK was clearly activated in v-Raf expressing NIH3T3 cells. Both the p90 and p75 gag-raf fusion proteins in addition to c-Raf-1 were immunoprecipitated from v-Raf NIH3T3 cells by the antisera. P75gag-raf has been shown to exhibit protein kinase activity, but it is possible that the $NH_2$ terminal gag fusion protein sterically hinders Raf phosphorylation of recombinant MEK-1 in the in vitro assay system. Further studies will have to be done to measure v-Raf kinase activity. The results argue that activation of MEK cannot be accounted for exclusively by the activation of Raf. Additional regulatory kinases for MEK must exist which contribute to MEK activation in thrombin stimulated, $G_i$ protein coupled pathways and in gip2 and v-src transfected cells.

Example 15

This Example demonstrates the ability of a PPPSS-trunc and Nco1-trunc of MEKK protein to activate MAPK activity compared with full-length MEKK protein and a negative control protein.

Figure 19:
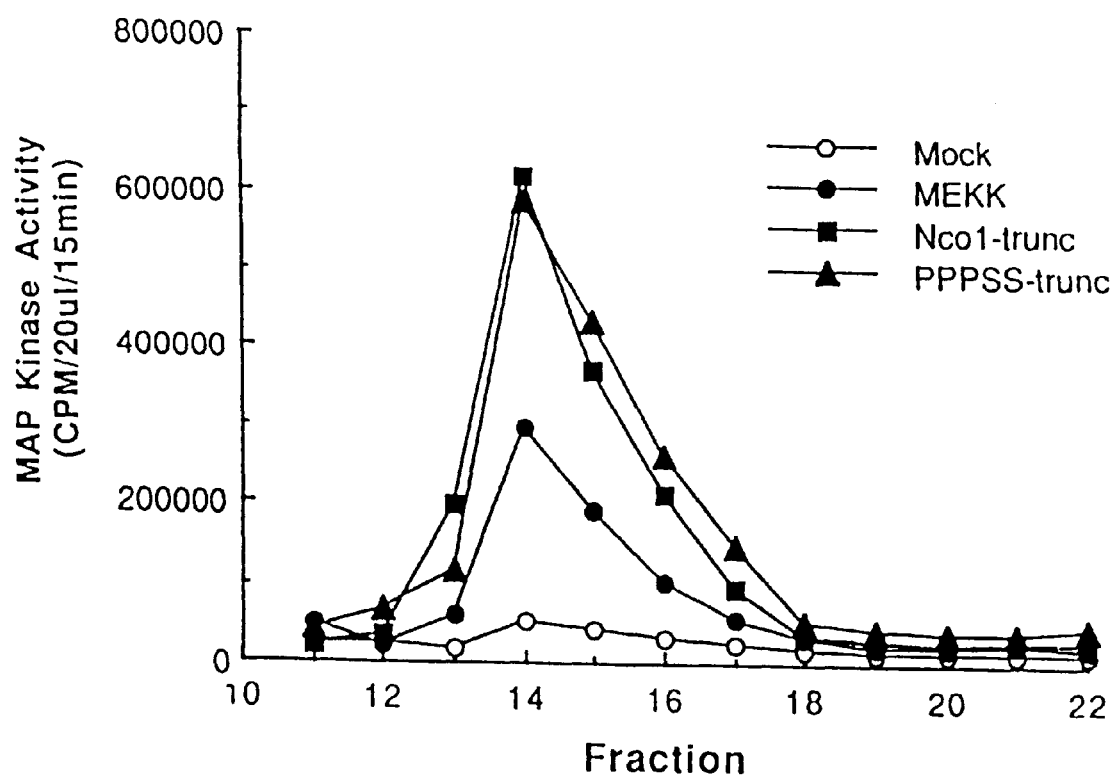
FIG. 19 shows improved MEKK activity by truncated MEKK molecules.

The results shown in FIG. 19 indicate that the truncated MEKK molecules were more active than the full-length MEKK. Indeed, the truncated MEKK molecules were at least about 1.5 times more active than full-length MEKK protein. Thus, removal of the regulatory domain of MEKK deregulates the activity of the catalytic domain resulting in improved enzyme activity.

Example 16

This example describes the preferential activation of JNK by MEKK compared with Raf.

Figure 20:
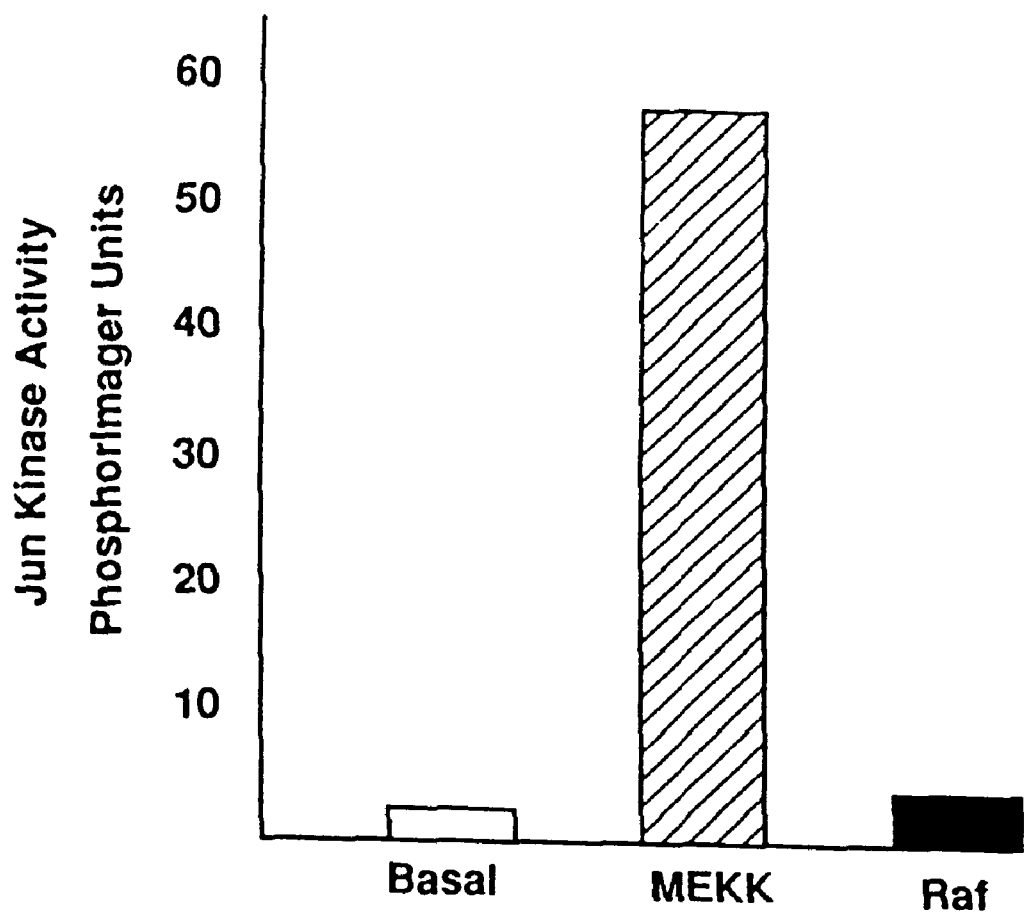
FIG. 20 shows JNK activation by MEKK protein.

HeLa cells were transiently transfected with truncated $MEKK_{370-672}$ under control of an inducible mammary tumor virus promoter, together with epitope tagged JNK1 (described in detail in Derijard et al., p. 1028, 1994, Cell, Vol. 76). Other HeLa cells were also transiently transfected with truncated BXB-Raf under control of an inducible mammary tumor virus promoter, together with epitope tagged JNK1 (Derijard et al., ibid.). The following day, $MEKK_{370-672}$ expression and BXB-Raf expression were induced by administration of dexamethasone (10 µM) for 17 hours. Cell extracts were then prepared and assayed for JNK activity using an immune complex kinase assay (detailed in Derijard et al., ibid.). Phosphorylation was quantitated by phosphorimager analysis. The results shown in FIG. 20 indicate that MEKK stimulated about 30-fold to about 50-fold activation more JNK activity over unstimulated cells (basal) and about 15-fold to about 25-fold JNK activity over Raf stimulated cells.

Example 17

This example describes that the phosphorylation of c-Myc transactivation domain in response to MEKK expression activates MYC-GAL 4 transcriptional activity.

Two separate expression plasmids were constructed as follows. The expression plasmid pLNCX was ligated to a cDNA clone comprising c-myc (1–103) ligated to GAL4 (1–147) (Seth et al., pp. 23521–23524, 1993, J. Biol. Chem., Vol. 266) to form the recombinant molecule pMYC-GAL 4. The expression plasmid $UAS_G$-TK Luciferase (Sadowski et al., pp. 563–564, 1988, Nature, Vol. 335) was transfected with either pMYC-GAL 4 or pLU-GAL into Swiss 3T3 cells using standard methods in the art to form recombinant cells herein referred to as LU/GAL cells. Recombinant control cells were also produced by transfecting in pGAL4-Control plasmids containing GAL4 (1–147) alone in the absence of c-myc (1–103).

LU/Gal cells were transfected with either $pMEKK_{370-672}$, pMEKK (encoding full-length $MEKK_{1-672}$), BXB-Raf, pMyc-Gal4, pCREB-Gal4 (encoding $CREB_{1-126}$, fused to $Gal4_{1-147}$; Hoeffler et al., pp. 868–880, 1989, Mol. Endocrinol., Vol. 3), pGal4, or CREB fusion protein referred to as GAL4.

Figure 21:
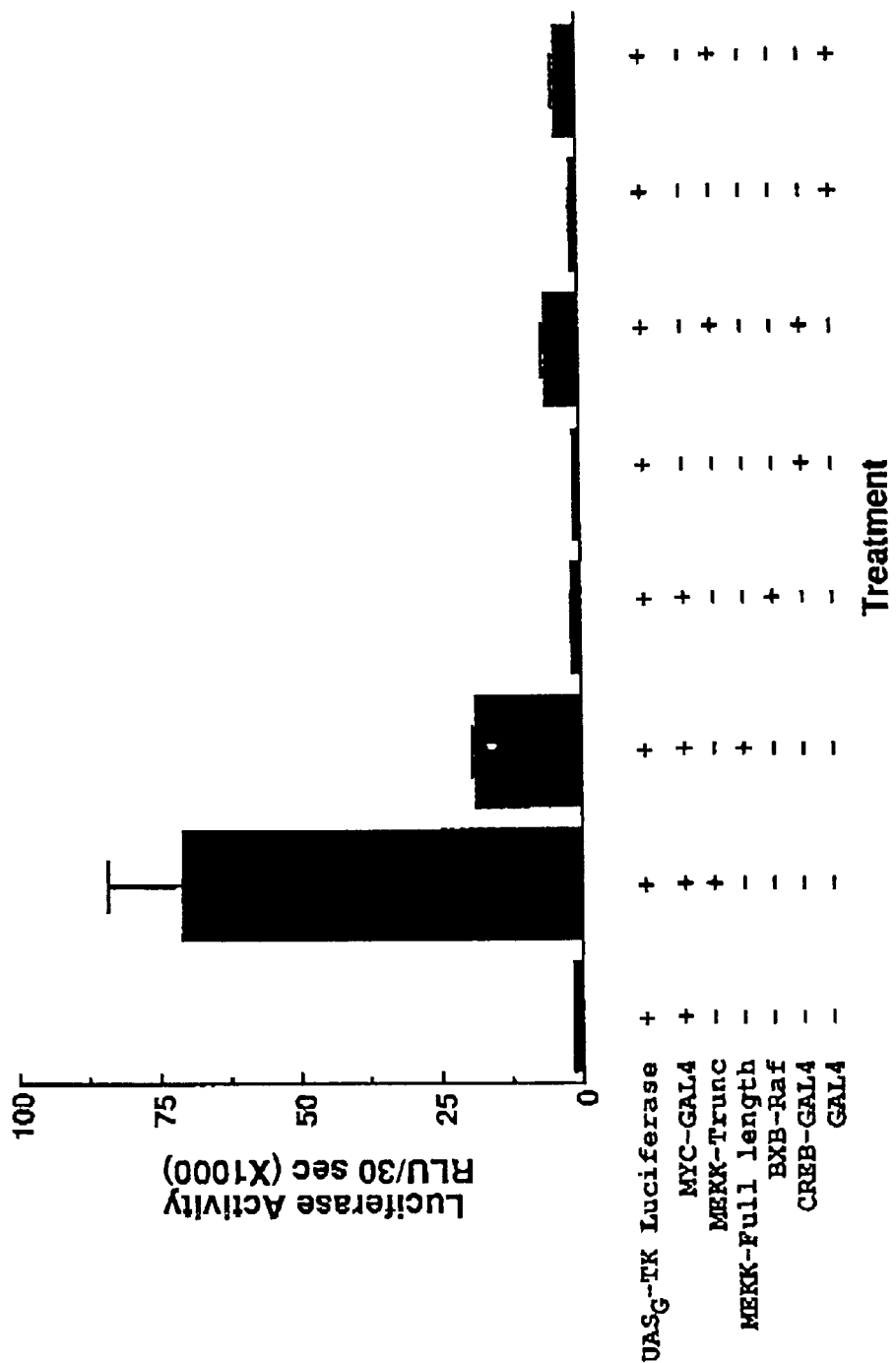
FIG. 21 shows regulation of c-Myc controlled transcription and not CREB controlled transcription by MEKK protein.
Figure 22A:
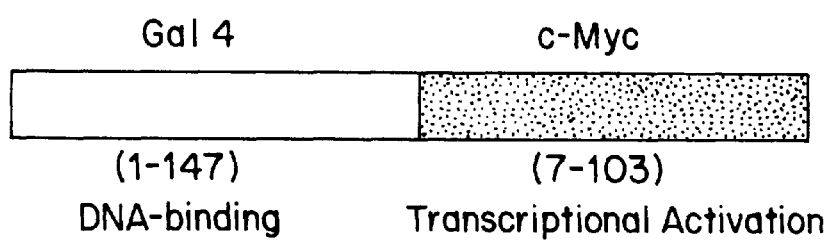
FIG. 22 is a schematic representation of MEKK regulation of c-Myc controlled transcription.
Figure 22B:
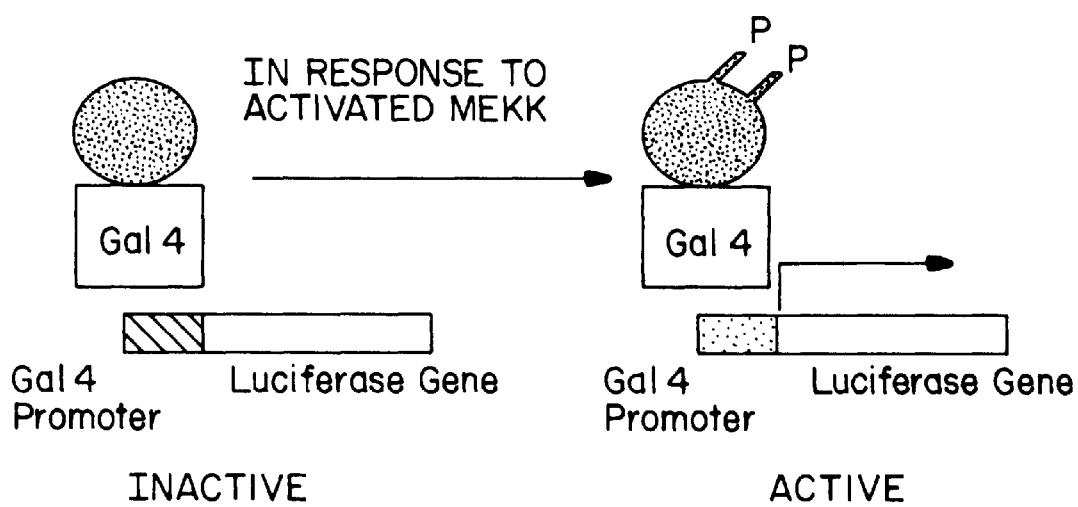

The transfected cells were incubated overnight and then lysed using methods standard in the art. The luciferase activity of each cell lysate was measure on a luminometer. The results shown in FIG. 21 indicate that MEKK is selectively capable of stimulating the phosphorylation of c-Myc transactivation domain in such a manner that the c-Myc domain is activated and induces transcription of the transfected luciferase gene. In addition, the results indicate that MEKK does not stimulate CREB activation. Also, activated Raf is unable to stimulate Myc activation. A schematic representation of the activation mechanism of c-Myc protein by MEKK is shown in FIG. 22.

Example 18

This Example describes the phosphorylation of p38 MAPK protein by MEKK3 protein and not MEKK1 protein.

Figure 23A:
FIG. 23 shows induction of p38 MAPK phosphorylation by MEKK3.
Figure 23B:
Figure 23C:
Figures 24A, 24B:
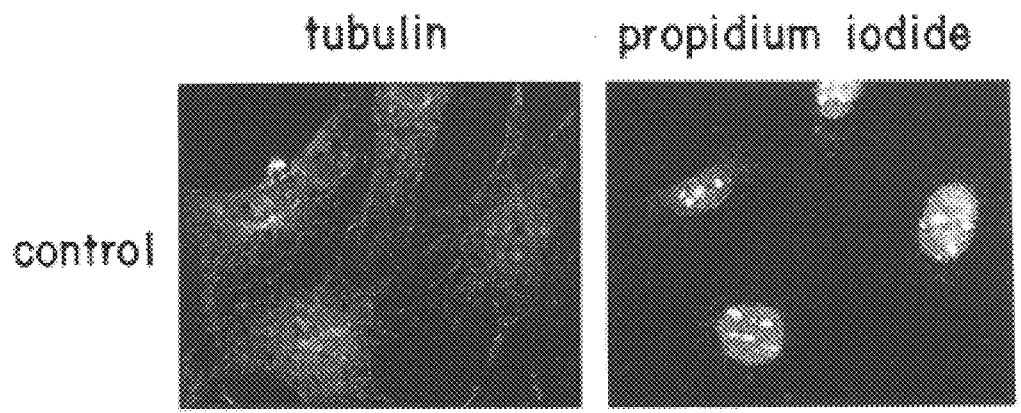
FIG. 24 shows induction of cellular apoptosis in Swiss 3T3 and REF52 cells by beauvericin.
Figures 24C, 24D:
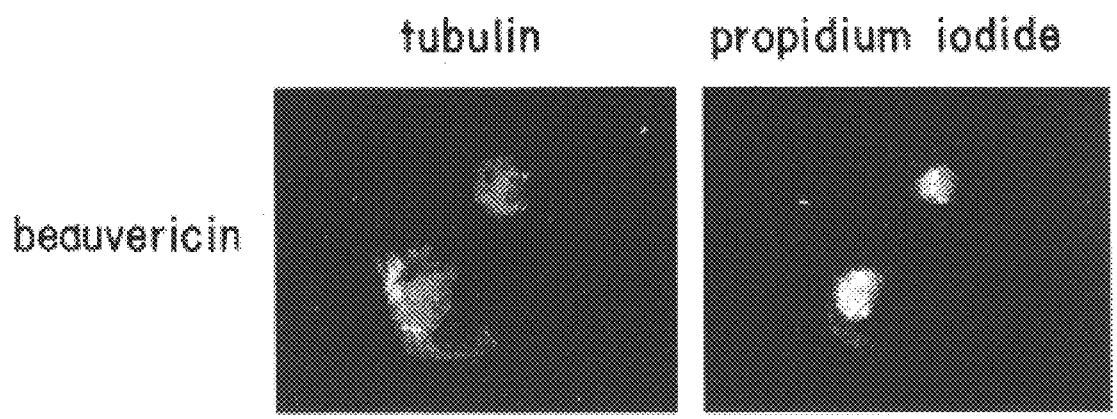
Figures 24E, 24F:
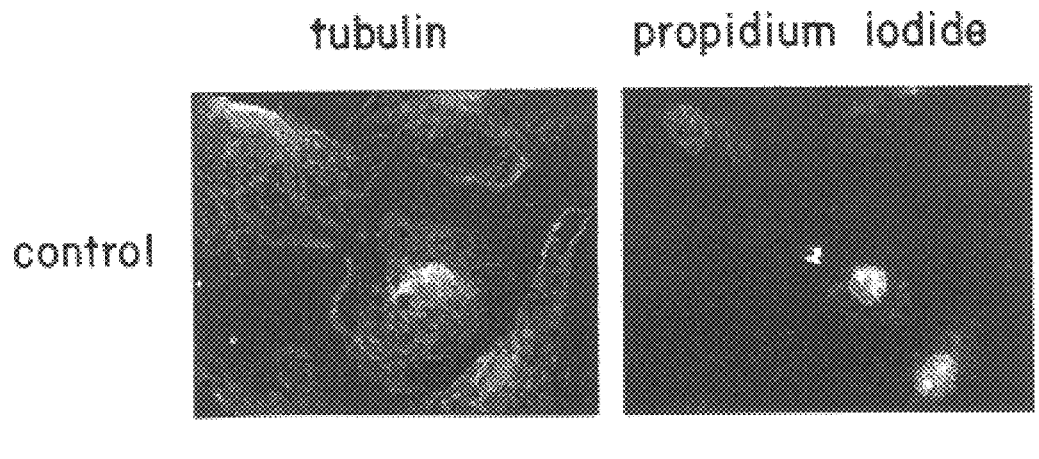
Figures 24G, 24H:
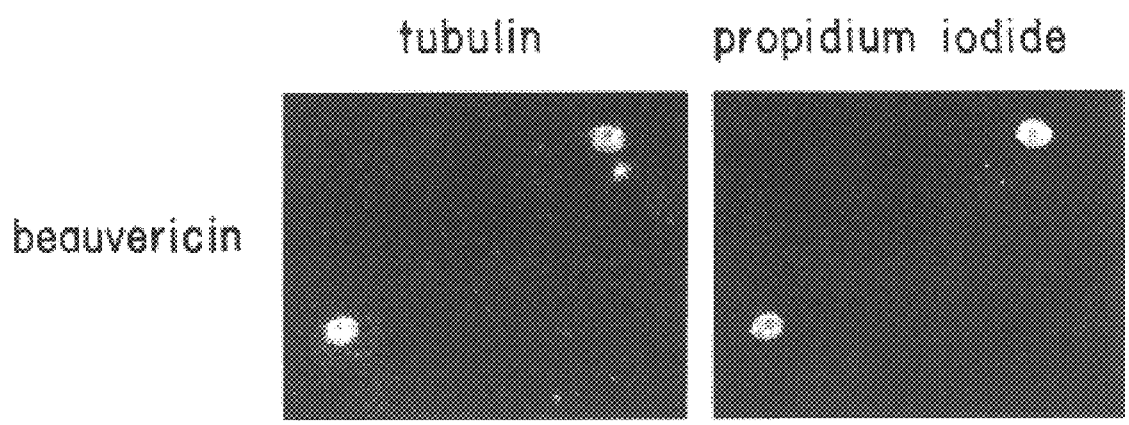
Figure 25A:
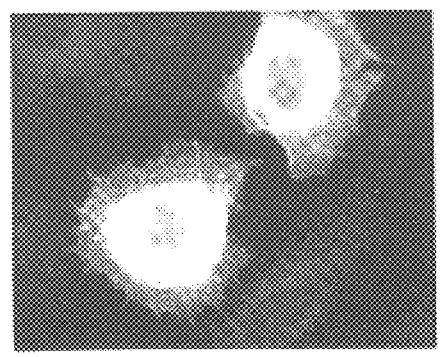
FIG. 25 shows induction of cellular apoptosis in REF52 cells by MEKK.
Figure 25B:
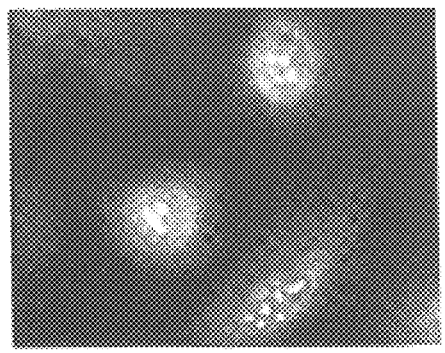
Figure 25C:
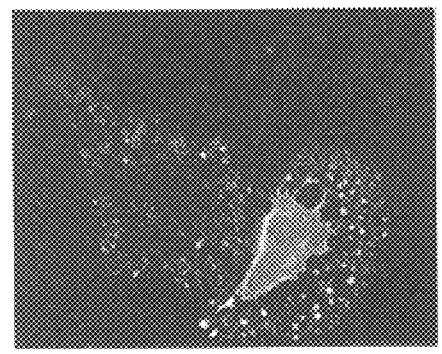
Figure 25D:
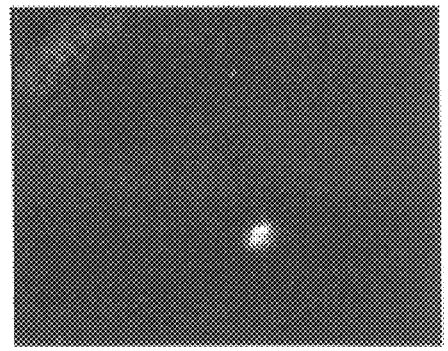
Figure 25E:
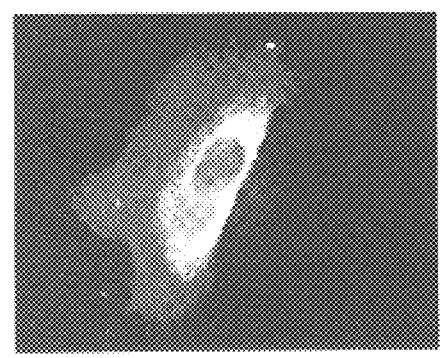
Figure 25F:
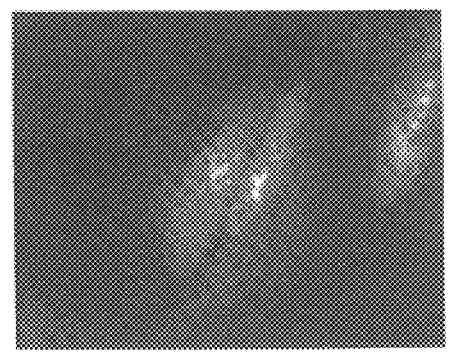
Figures 26A, 26B:
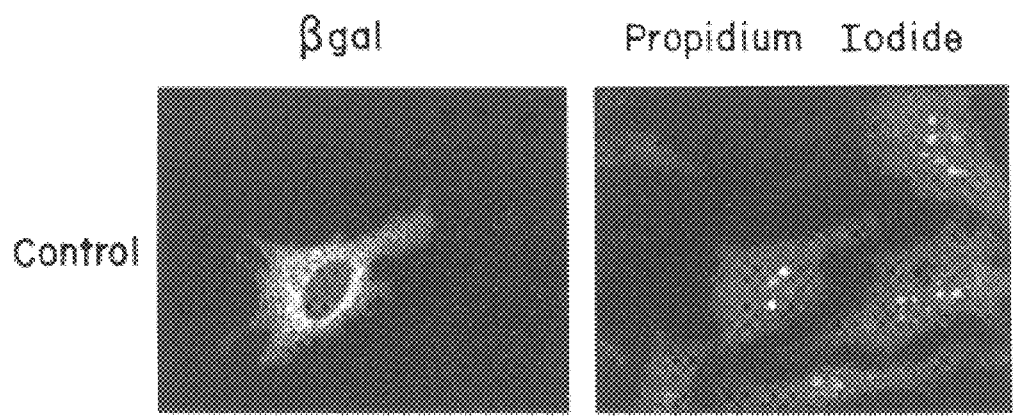
FIG. 26 shows induction of cellular apoptosis in Swiss 3T3 cells by MEKK.
Figures 26C, 26D:
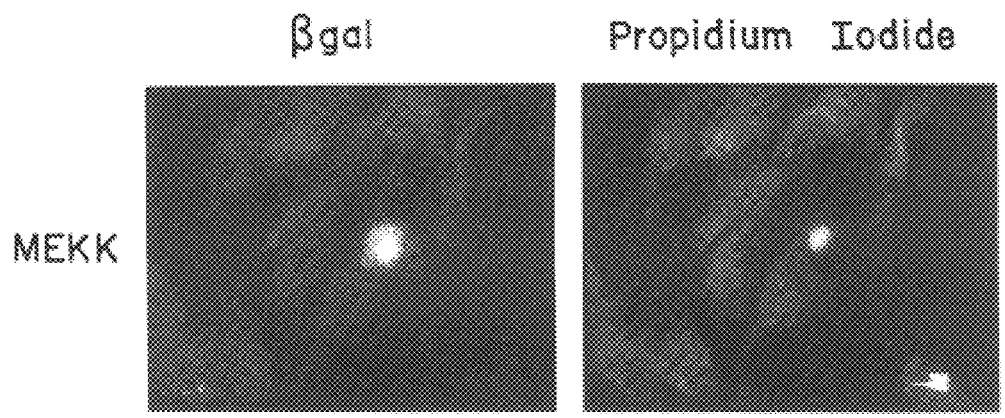
Figures 26E, 26F:
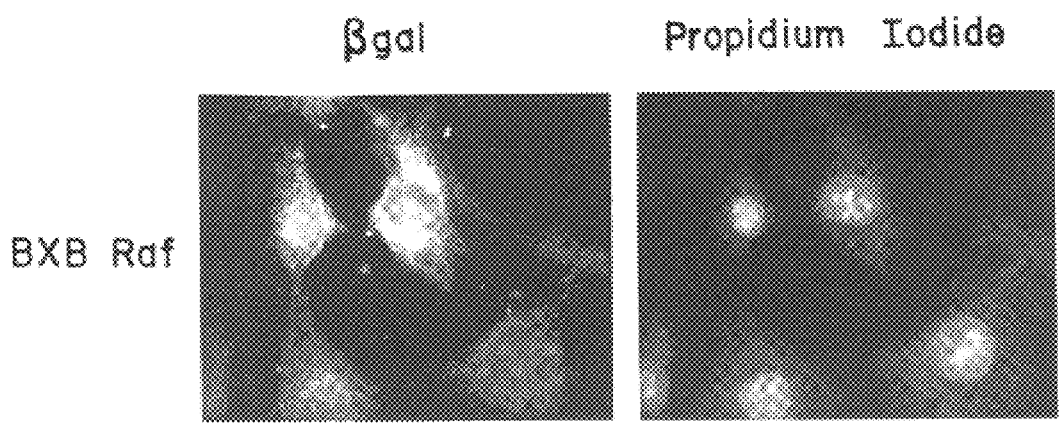

COS cells were transfected with the expression plasmid pCVM5 ligated to cDNA clones encoding either MEKK 1 or MEKK 3 protein, or a control pCVM5 plasmid lacking MEKK cDNA inserts. Forty-eight hours after transfection, the COS cells were lysed and the lysate fractionated on a Mono Q FPLC column using conditions described in Example 4. The fractions were analyzed for tyrosine phosphorylation of MAP kinase-like enzymes using the kinase assay described in Example 4. Referring to FIG. 23, expression of MEKK 3 induces tyrosine phosphorylation of p38 MAPK and the p42 and p44 forms of MAPK. MEKK 1, however, only induces weak phosphorylation of p38 MAPK but does induce phosphorylation of p42 and p44 MAPK.

Example 19

This example describes MEKK-induced apoptosis.

Cells were prepared for the apoptosis studies as follows. Swiss 3T3 cells and REF52 cells were transfected with an expression plasmid encoding β-Galactoctosidase (β-Gal). One set of β-Gal transfected cells were then microinjected with an expression vector encoding $MEKK_{370-672}$ protein. Another set of β-Gal transfected cells were then microinjected with an expression vector encoding truncated BXB-Raf protein.

A. Beauvericin-induced apoptosis

A first group of transfected Swiss 3T3 cells and REF52 cells were treated with 50 μM beauvericin for 6 hours at 37° C. Beauvericin is a compound known to induce apoptosis in mammalian cells. A second group of cells were treated with a control buffer lacking beauvericin. The treated cells were then fixed in paraformaldehyde and permeabilized with saponin using protocols standard in the art. The permeabilized cells were then labelled by incubating the cells with a fluorescein-labelled anti-tubulin antibody (1:500; obtained from GIBCO, Gaithersburg, Md.) to detect cytoplasmic shrinkage or 10 μM propidium iodide (obtained from Sigma, St. Louis, Mo.) to stain DNA to detect nuclear condensation. The labelled cells were then viewed by differential fluorescent imaging using a Nikon Diaphot fluorescent microscope. FIG. 24 shows two fields of Swiss 3T3 cells and REF52 cells, one field representing cells treated with the control buffer and a second field representing cells treated with beauvericin. The cells treated with beauvericin demonstrated cytoplasmic shrinkage (monitored by the anti-tubulin antibodies) and nuclear condensation (monitored by the propidium iodide) characteristic of apoptosis.

B. MEKK-induced apoptosis

Swiss 3T3 cells and REF52 cells microinjected with a β-galatoctosidase expression plasmid, and an MEKK encoding plasmid or a BXB-Raf encoding plasmid, were treated and viewed using the method described above in Section A. An anti-β-Gal antibody (1:500, obtained from GIBCO, Gaithersburg Md.) was used to detect injected cells. Referring to FIG. 25, microscopic analysis of REF52 cells indicated that the cells expressing MEKK protein underwent cytoplasmic shrinkage and nuclear condensation leading to apoptotic death. In contrast, cells expressing BXB-Raf protein displayed normal morphology and did not undergo apoptosis. Similarly, referring to FIG. 26, microscopic analysis of Swiss 3T3 cells indicated that the cells expressing MEKK protein underwent cytoplasmic shrinkage and nuclear condensation leading to apoptotic death. In contrast, cells expressing BXB-Raf protein displayed normal morphology and did not undergo apoptosis.

FIG. 27 shows 3 representative fields of RFE52 cells expressing MEKK protein which have undergone substantial cytoplasmic shrinkage and nuclear condensation compared with a control cell not expressing MEKK. Similarly, FIG. 28 shows 3 representative fields of Swiss 3T3 cells expressing MEKK protein which have undergone substantial cytoplasmic shrinkage and nuclear condensation compared with a control cell not expressing MEKK. Thus, MEKK and not Raf protein can induce apoptotic programmed cell death.

Example 20

This Example describes regulation of MAPK activity by both MEKK and Raf protein.

COS cells were prepared using the method described in Example 3. In addition, COS cells were transfected with the pCVMV5 Raf construct (1 μg: Raf). FPLC MONO Q ion-exchange column fractions were prepared as described in Example 3 and assayed for MAPK activity according to the method described in Heasley et al., ibid.

Figure 29:
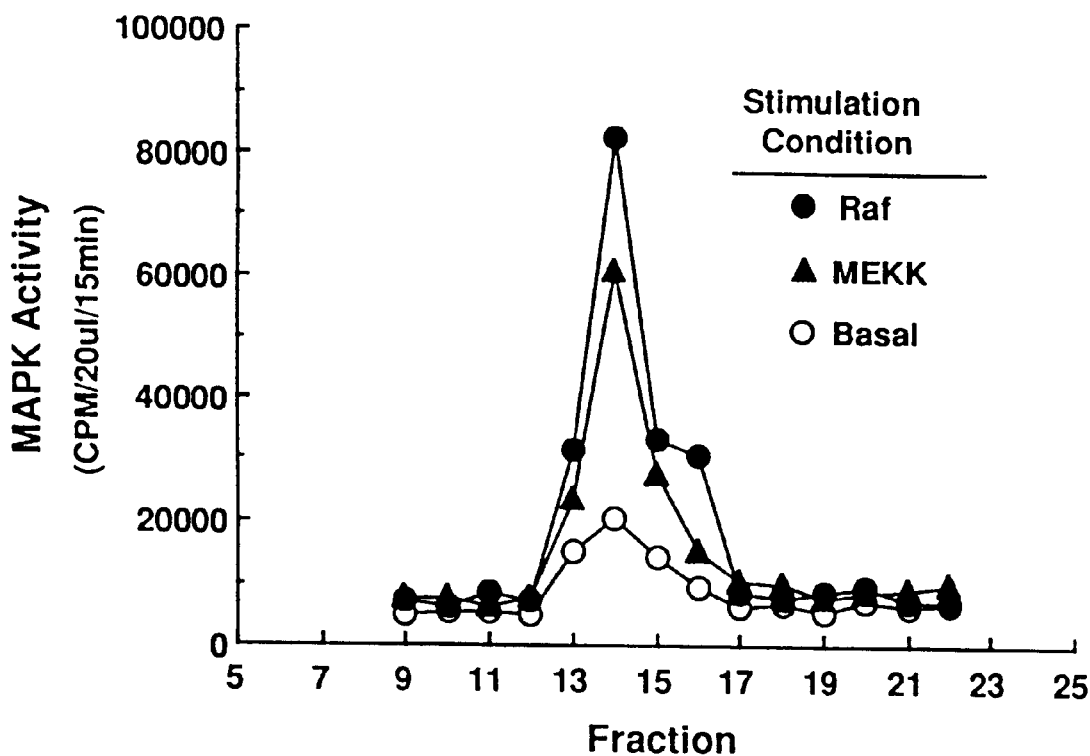
FIG. 29 shows similar stimulation of MAPK activity by MEKK protein and Raf protein.

Referring to FIG. 29, both MEKK and Raf overexpression in COS 1 cells resulted in similar levels of stimulation of MAPK activity over basal levels.

Example 21

This example demonstrates the ability of COS cell-expressed MEKK1 proteins to bind to GST-$Ras^{V12}$.

COS cells were transiently transfected by the DEAE-dextran protocol as generally described in Example 3. Cos cells were transfected with: (1) p-MEKK1 containing a nucleic acid molecule encoding MEKK1 as described in Lange-Carter et al. (*Science* 260:315–319, 1994); (2) p-$MEKK_{NH2}$ containing a nucleic acid molecule that encodes a 858 base pair Pvull(682)-Ncol(1541) restriction digest fragment of the amino terminus of MEKK1 ligated into pCMV5; (3) p-$MEKK_{COOH}$ containing a nucleic acid molecule that encodes a 1435 base pair Ncol(1541)-Sspl (2976) restriction digest fragment that includes the entire kinase domain of MEKK1 ligated into pCMV5; (4) pCMV5 without insert; or (5) p-C4Raf containing a nucleic acid molecule that encodes the amino terminus of Raf-1 ligated into pCMV5. COS cells expressing the various MEKK1 proteins were selected by the method described in Example 3.

COS cells expressing the various MEKK1 proteins were lysed in EB (1% Triton X-100, 10 mM Tris HCl [pH 7.4], 5 mM EDTA, 50 mM NaCl, 50 mM NaF, 0.1% bovine serum albumin, 0.2 U/ml aprotinin, 1 mM phenylmethylsulfonyl fluoride and 2 mM $Na_3$ $VO_4$). The lysates were separated into two equal parts for separate binding reactions. Half of the lysate was incubated with GST agarose (1.5 μg) while half of the lysate was incubated with GST-$Ras^{V12}$ agarose (1.5μg) (purchased from UBI) for 1 hr at 4° C. The GST-$Ras^{V12}$ was preincubated at 30° C. for 30 min with 1 mM nucleotide (GDP or GTPγS). The nucleotide binding reaction was stopped by adding $MgCl_2$ to a final concentration of 20 mM. After the 1 hr binding reaction the agarose beads were pelleted at 2000 rpm for 2 min and washed 3 times with PBS+1.0% Triton X-100. The washed agarose beads were boiled in Laemmli SDS sample buffer and the proteins resolved by SDS polyacrylamide gel electrophoresis. Proteins were transferred onto nitrocellulose for immunoblotting with antibodies specific for an $NH_2$ terminal fusion protein (described in Example 1) or a COOH terminal peptide (described in Example 1). C4Raf binding was detected using an antibody specific for Raf described in Example 8.

Initial immunoblotting results using anti-Raf antibodies demonstrated that C4Raf bound to GST-$Ras^{V12}$(GTPγS) agarose but not to the GST agarose control. Additionally, no Raf immunoreactive proteins were detected bound to Ras from COS cells transfected with pCMV5. These results indicated that the Ras binding assay was functional.

Figure 30:
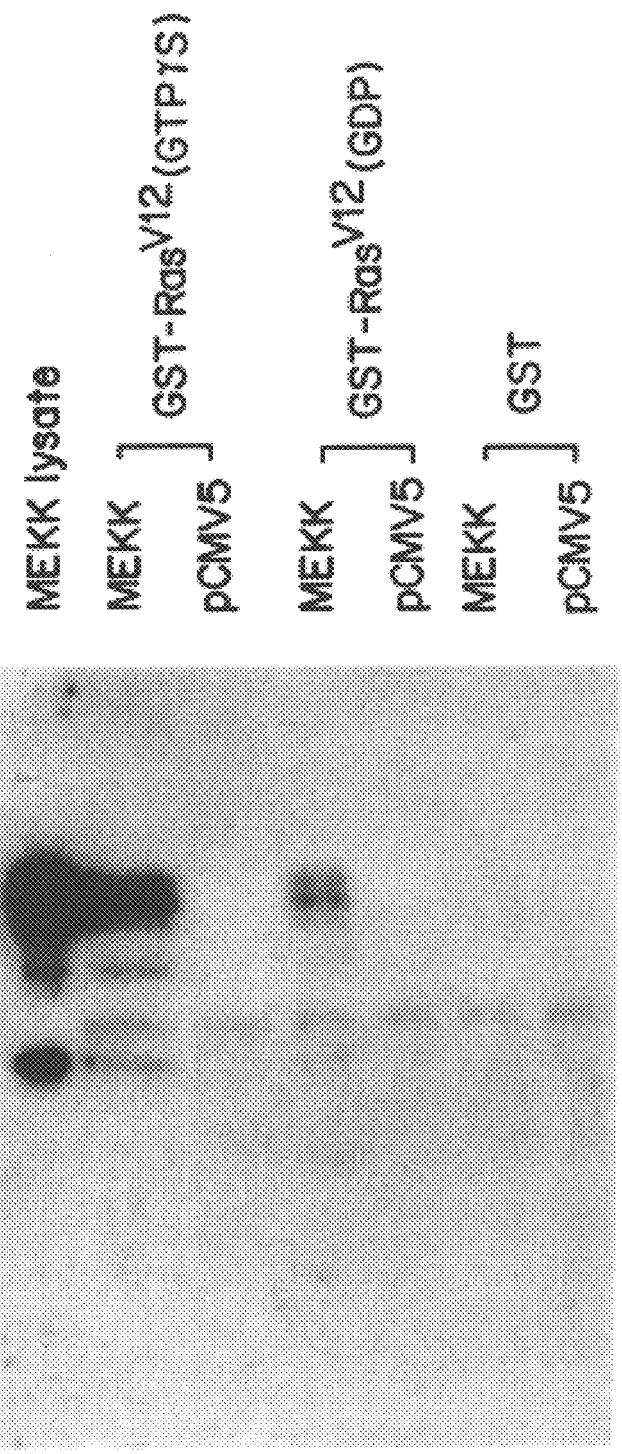
FIG. 30 shows the binding of MEKK1 protein from COS cell lysates to GST-$Ras^{V12}$(GTPγS) agarose.

Referring to FIG. 30, immunoblotting results using anti-MEKK antibodies indicate that protein encoded by p-MEKK1 (MEKK1) transiently expressed in COS cells was capable of binding GST-$Ras^{V12}$ in a GTP dependent manner. MEKK1 from COS cell lysates bound to GST-$Ras^{V12}$(GTPγS), while little binding to GST-$Ras^{V12}$(GDP) was detectable. With the conditions used, MEKK1 binding to GST-$Ras^{V12}$(GTPγS) was at least 5-fold greater than the binding to GST-$Ras^{V12}$(GDP). No detectable MEKK1 was bound to GST.

Figure 31:
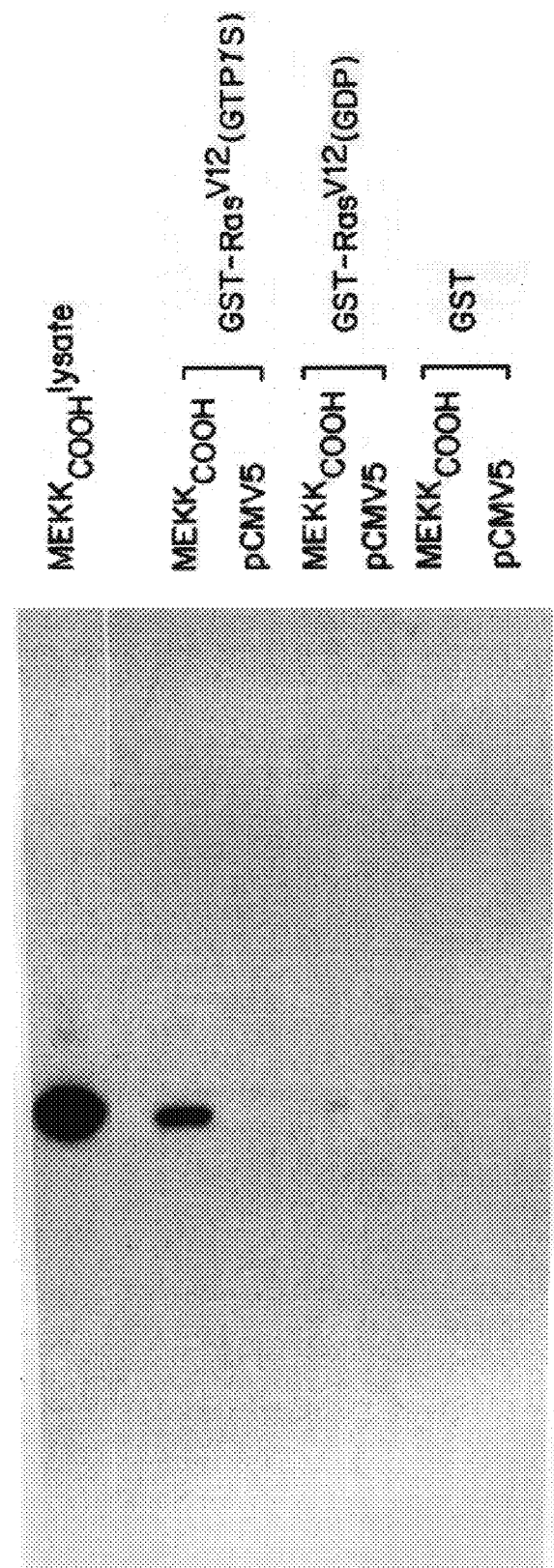
FIG. 31 shows the binding of $MEKK_{COOH}$ protein from COS cell lysates to GST-$Ras^{V12}$(GTPγS) agarose.
Figure 32:
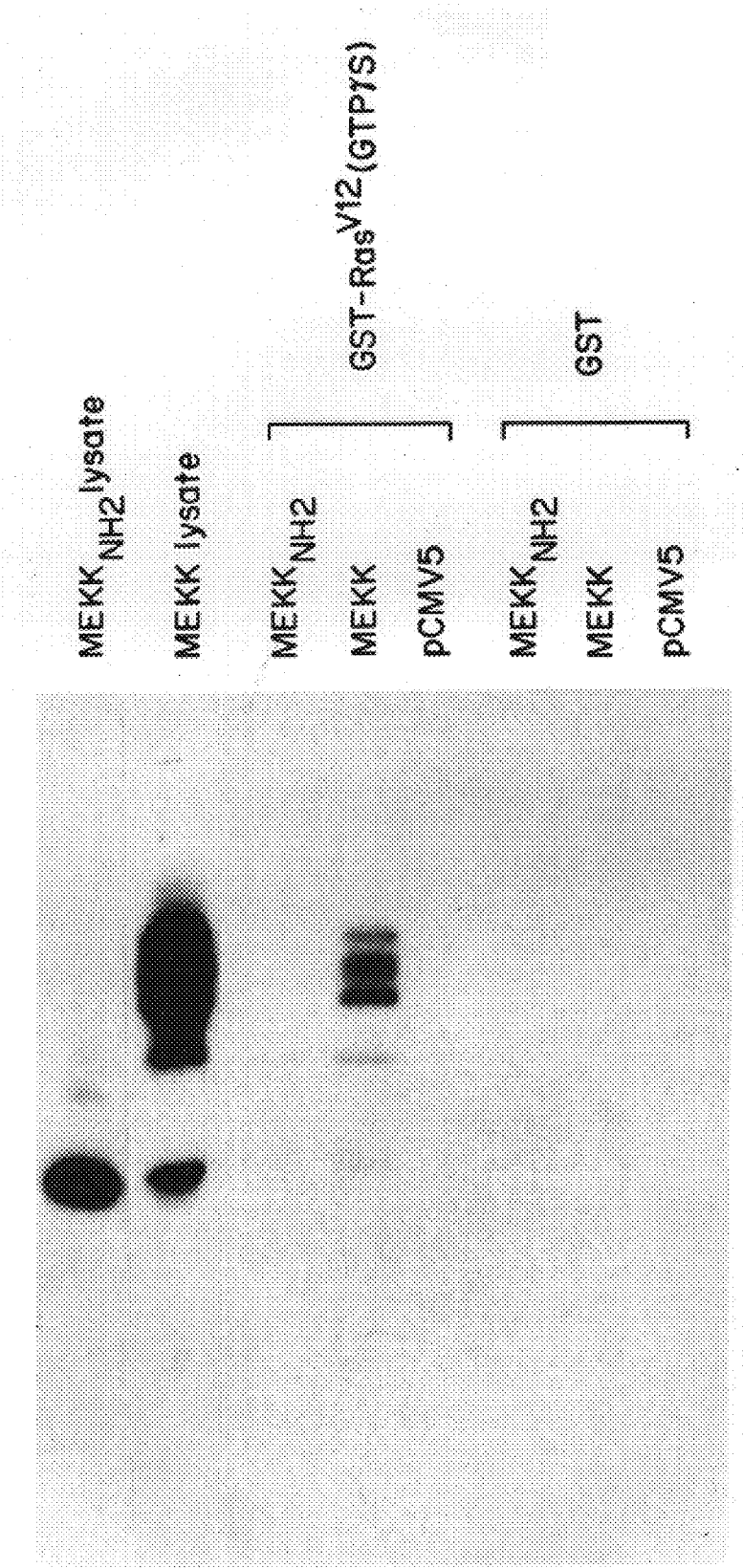
FIG. 32 shows the lack of binding of $MEKK_{NH2}$ protein from COS cell lysates to GST-$Ras^{V12}$(GTPγS) agarose.

The domain critical for the binding of MEKK1 to Ras was identified based on the results shown in FIG. 31. The protein encoded by p-MEKK$_{COOH}$ (MEKK$_{COOH}$) bound to GST-Ras$^{V12}$ in a GTP dependent manner. Little MEKK$_{COOH}$ bound to GST-Ras$^{V12}$(GDP). No detectable MEKK$_{COOH}$ was bound to GST. In addition, when protein encoded by P-MEKK$_{NH2}$ (MEKK$_{NH2}$) was expressed in COS cells, no binding to Ras was detected. FIG. 32 shows that in contrast to the ability of Raf-1 to bind to Ras through its amino terminus, MEKK$_{NH2}$ failed to bind GST-Ras$^{V12}$(GTPγS) even though the protein was expressed to similar levels as MEKK1 in the same experiment. Thus, GST-Ras$^{V12}$ binds to MEKK1 at a site located within the COOH-terminal catalytic domain of MEKK1.

Example 22

This example demonstrates the ability of purified recombinant MEKK1 proteins to bind directly to GST-Ras$^{V12}$.

A construct encoding the kinase domain of a Rat MEKK1 cDNA (95% identical to mouse MEKK1) with a N-terminal hexahistidine tag (referred to herein as MEKK$_{COOH}$-His; provided by Dr. Melanie Cobb, Department of Pharmacology, University of Texas Southwestern Medical School, Dallas, Tex.) was expressed in bacteria and soluble active enzyme was purified on Ni$_2$+-NTA agarose according to the method generally described in Gardner et al. (*Methods of Enzymology* 238:258–270, 1994) Purified recombinant MEKK$_{COOH}$-His was incubated with either GST or GST-Ras$^{V12}$ in PAN buffer(10 PIPES [pH 7.0], 100 nM NaCl, 0.2 U/ml aprotinin) for 1 hr at 4° C. The agarose beads were pelleted and washed 3 times in PAN buffer. The washed agarose beads were then incubated in kinase buffer (20 mM PIPES [pH 7.0], 10 mM MnCl$_2$, 40 μCi[γ$^{32}$P]ATP, 20 μg/ml aprotinin) containing 100 ng recombinant kinase inactive MEK1 as substrate in a final volume of 150 μl, at 30° C. for 20 min. To test the direct interaction of MEKK1 with the effector domain of Ras, samples were prepared by pre-incubating the agarose beads with either 100 μM of Ras peptide consisting of residues 17–42 of H-Ras or 100 μM of Ras control peptide ([D-Arg$^1$,D-Phe$^5$,DTrp$^{7,9}$Leu$^{11}$] substance P peptide for 1 hr at 4° C. prior to addition of the MEK1 substrate. A control reaction containing wild-type MEKK1 which autophosphorylates, served as a marker for the MEKK1 substrate. Reactions were terminated by addition of 5×Laemmlei SDS sample buffer, boiled and resolved by SDS-PAGE.

Referring to FIG. 32, the results indicate that there was direct binding of Ras-GTPγS to purified MEKK$_{COOH}$-His as measured by the increased phosphorylation of KM MEK1 using GST-Ras$^{V12}$(GTPγS) beads incubated with recombinant MEKK$_{COOH}$-His. The interaction between Ras and MEKK$_{COOH}$-His was GTP dependent because essentially no KM MEK1 phosphorylation could be detected with GST-Ras$^{V12}$(GDP) beads incubated with recombinant MEKK$_{COOH}$.

Referring to FIG. 33, the results indicate that the presence of Ras effector peptide prevented the binding of GST-Ras$^{V12}$ (GTPγS) agarose to MEKK$_{COOH}$-His, thereby preventing the phosphorylation of KM MEK1 substrate present in the sample. MEKK$_{COOH}$-His was able to bind to GST-Ras$^{V12}$ (GTPγS) in the presence of buffer alone or in the presence of a control peptide ([DArg$^1$,D-Phe$^5$,D-Trp$^{7,9}$,Leu$^{11}$] substance P peptide), resulting in the phosphorylation of KM MEK1 substrate.

Taken together, the results described in Examples 21 and 22 demonstrate that MEKK1 is a Ras effector and selectively binds to Ras in a GTP dependent manner. In addition, the binding of MEKK1 to Ras in vitro is direct and occurs via the COOH terminal region of MEKK1 that encodes the catalytic kinase domain.

SEQUENCE LISTING

The following Sequence Listing is submitted pursuant to 37 CFR §1.821. A copy in computer readable form is also submitted herewith.

Applicant asserts pursuant to 37 CFR §1.821(f) that the content of the paper and computer readable copies of SEQ ID NO:1 and SEQ ID NO:2 submitted herewith are the same.

What is claimed:

1. A method for regulating mitogen ERK kinase kinase (MEKK) protein activity in a cell comprising transforming or transfecting the cell with a nucleic acid molecule encoding an MEKK protein such that MEKK protein activity in the cell is regulated, wherein said nucleic acid molecule is capable of hybridizing under stringent conditions with a nucleic acid molecule comprising a nucleotide sequence selected from the group consisting of SEQ ID NO:1, SEQ ID NO:3, SEQ ID NO:5, SEQ ID NO:7, SEQ ID NO:9, and SEQ ID NO:11.

2. A method for regulating mitogen ERK kinase kinase (MEKK) protein activity in a cell comprising transforming or transfecting the cell with a nucleic acid molecule encoding an MEKK protein such that MEKK protein activity in the cell is regulated, wherein said nucleic acid molecule encodes an MEKK protein comprising an amino acid sequence selected from the group consisting of SEQ ID NO:2, SEQ ID NO:4, SEQ ID NO:6, SEQ ID NO:8, SEQ ID NO:10, and SEQ ID NO:12.

3. The method of claim 1 or 2, wherein said cell is a fungal cell.

* * * * *

UNITED STATES PATENT AND TRADEMARK OFFICE
CERTIFICATE OF CORRECTION

PATENT NO. : 5,981,265
DATED : Nov. 9, 1999
INVENTOR(S) : Gary L. Johnson

It is certified that error appears in the above-identified patent and that said Letters Patent is hereby corrected as shown below:

Title page,
Item [63], line 6, after "Oct. 14, 1994," please insert --

Pat. No. 5,854,043, which is a continuation-in-part of application No. 08/049,254, Apr. 15, 1993, Pat. No. 5,405,941, --.
Title page, Item [63], line 7, please delete "Pat. No. 5,405,941" and insert -- which is a continuation-in-part of application No. 08/049,254, Apr. 15, 1993, Pat. No. 5,405,941 --.

Signed and Sealed this

Fourth Day of July, 2000

Attest:

Q. TODD DICKINSON

*Attesting Officer*       *Director of Patents and Trademarks*